US011739388B2

(12) United States Patent
Clokie et al.

(10) Patent No.: US 11,739,388 B2
(45) Date of Patent: Aug. 29, 2023

(54) PHAGE-BASED DETECTION OF BORRELIOSIS AND MEANS THEREFOR

(71) Applicants: UNIVERSITY OF LEICESTER, Leicester (GB); PHELIX RESEARCH AND DEVELOPMENT LIMITED, London (GB)

(72) Inventors: Martha Rebecca Jane Clokie, Leicestershire (GB); Jinyu Shan, Leicestershire (GB); Louis Charles Teulieres, London (GB)

(73) Assignees: UNIVERSITY OF LEICESTER, Leicester (GB); PHELIX RESEARCH AND DEVELOPMENT LIMITED, London (GB)

( * ) Notice: Subject to any disclaimer, the term of this patent is extended or adjusted under 35 U.S.C. 154(b) by 21 days.

(21) Appl. No.: 16/346,178

(22) PCT Filed: Nov. 3, 2017

(86) PCT No.: PCT/GB2017/053323
§ 371 (c)(1),
(2) Date: Apr. 30, 2019

(87) PCT Pub. No.: WO2018/083491
PCT Pub. Date: May 11, 2018

(65) Prior Publication Data

US 2019/0276877 A1 Sep. 12, 2019

(30) Foreign Application Priority Data

Nov. 3, 2016 (GB) ...................................... 1618565

(51) Int. Cl.

| | |
|---|---|
| ***C12Q 1/689*** | (2018.01) |
| ***C12Q 1/6811*** | (2018.01) |
| ***C12Q 1/6888*** | (2018.01) |
| ***G01N 33/569*** | (2006.01) |

(52) U.S. Cl.
CPC ............ *C12Q 1/689* (2013.01); *C12Q 1/6811* (2013.01); *C12Q 1/6888* (2013.01); *G01N 33/56911* (2013.01); *G01N 33/56983* (2013.01); *C12Q 2600/112* (2013.01); *G01N 2333/005* (2013.01); *G01N 2333/20* (2013.01); *G01N 2800/26* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 2003/0138868 A1 | 7/2003 | Jungblut et al. | |
| 2012/0184710 A1 | 7/2012 | Lundberg et al. | |

FOREIGN PATENT DOCUMENTS

| | | | | |
|---|---|---|---|---|
| EP | 1394254 A1 | 3/2004 | | |
| WO | 98/58943 A1 | 12/1998 | | |
| WO | WO-9858943 A1 * | 12/1998 | ............ | C07K 14/20 |
| WO | 03/033724 A2 | 4/2003 | | |

OTHER PUBLICATIONS

Eggers, Christian H., "Identification and characterization of a bacteriophage of Borrelia burgdorferi" (2000). Graduate Student Theses, Dissertations, & Professional Papers. (Year: 2000).*
Chomczynski and Sacchi, Nature Protocols, 2006, 1(2):581-585. (Year: 2006).*
International Search Report dated Dec. 22, 2017 in corresponding PCT/GB2017/053323.
Babb, Kelly et al., "Borrelia burgdorferi EbfC, a Novel, Chromosomally Encoded Protein, Binds Specific DNA Sequences Adjacent to erp Loci on the Spirochete's Resident cp32 Prophages," Journal of Bacteriology, Jun. 2006, vol. 188, No. 12, pp. 4331-4339.
Miller, Jennifer C. et al., "Expression of Borrelia burgdorferi erp genes during infection of non-human primates," Microbial Pathogenesis, vol. 39, 2005, pp. 27-33.
Miller, Jennifer C. et al., "Borrelia burgdorferi erp genes are expressed at different levels within tissues of chronically infected mammalian hosts," International Journal of Medical Microbiology, vol. 296 S1, 2006, pp. 185-194.
Search Report under Section 17 dated Aug. 20, 2017 for corresponding GB Application No. GB1618565.4.
Christian H. Eggers, et al., Molecular Evidence for a New Bacteriophage of Borrelia burgdorferi, Journal of Bacteriology (Dec. 1999) vol. 181, No. 23, p. 7308-7313.
Jonathan T. Skare, et al., Cloning and Molecular Characterization of Plasmid-Encoded Antigens of Borrelia burgdorferi Infection and Immunity (Sep. 1999) vol. 67, No. 9, p. 4407-4417.
Thad B. Stanton, et al., Detection of bacteriophage VSH-1 svp38 gene in Brachyspira spirochetes, FEMS Microbiology Letters (2003) 224 p. 225-229.
Office Action dated Oct. 24, 2022 in corresponding Chinese Application No. 201780082195.0.

* cited by examiner

*Primary Examiner* — Nicole Kinsey White
(74) *Attorney, Agent, or Firm* — Duane Morris LLP; Deborah L. Lu

(57) ABSTRACT

This invention relates to methods of detecting *Borrelia burgdorferi* sensu lato or for detecting *Borrelia* associated with Relapsing Fever (RF), kits for carrying out such methods, and methods of treating *Borrelia burgdorferi* sensu lato or RF infections in a subject. Uses of phage specific for *Borrelia* are also provided.

18 Claims, 11 Drawing Sheets

Specification includes a Sequence Listing.

FIG. 2
Lyme disease
Relapsing fever
B. afzelii
B. spielmanii
B. valaisiana
B. garinii
B. finlandensis
B. burgdorferi
B. bissettii
B. parkeri
B. coriaceae
B. duttonii
B. hispanica
Lambda
87
99
81
99
0.2

SEQUENCE LISTING

```
<160> NUMBER OF SEQ ID NOS: 119

<210> SEQ ID NO 1
<211> LENGTH: 1353
<212> TYPE: DNA
<213> ORGANISM: Phage from Borrelia burgdorferi

<400> SEQUENCE: 1

gtgaacttat atcaaacaaa actttttaca acactacaaa aggaatacaa aaataaatat      60

ggagttgata tatcacaatt tgtaaagcta acaaattctt caattaattt tgataagttt     120

gaagaagaac agttaacttt aaaacaaaaa aatgtgataa aaagcattaa aaagaataat     180

gaaaagaaga ttatactcag cggaggcata gctagtggca aaacgtatct tgcatgttat     240

ctttttctaa aaagtttaat tgaaattaaa aagttatact ctagtgatac taataatttc     300

attataggga attcacaacg ttcagttgaa gttaatgttt tggggcaatt tgaaaagcta     360

tgtaaacttc ttaaaattcc ttatattcca agacatacaa ataattcata tattctgatt     420

gattcactac gtattaatct atatggagga gataaggcaa gtgattttga aagatttagg     480
```

-continued

```
ggaagtaatt cggcacttat ttttgttaat gaggctacaa ctttacacaa gcaaacttta    540

gaggaagtct taaaaagact aagatgcggg caagaaacta ttatttttga tactaatcct    600

gatcatccag aacactattt taaaaccgat tatattgata atatagcgac ctttaagaca    660

tataagttta caacttatga taatgtgcta cttagtaaag gatttgtcga aacacaagaa    720

aagctatata aagatatacc atcatataaa gcaagagttt tgttaggtga gtggatagca    780

agcactgatt caatttttac acaaataaat attactgatg attatgtatt tactagcccg    840

atagcatatt tagacccagc atttagtgtt ggcggggata acactgcatt atgtgttatg    900

gagcgagttg atgataagta ttatgctttt gtatttcaag accaaagacc agctaatgat    960

ccttatatta tgaatatggt aaagactgtt atagaaaatt tcaatgtgca tacactgtat   1020

ttagaggata gagataatac aaaaggtgct ggtggattga cccgtgaata catcttgcta   1080

agaagtaata taagccaata ttttagaatt gttccagtta agccaaagtc taataaattt   1140

agcagaataa caacgttaat tacgccgttt acttacaaaa aactttatat tacaaagtac   1200

agtagttctt ccgtatttaa tgatatttat tcgtataagg gggataataa aacccatgat   1260

gacgctcttg atgcaatatc tgcagcatat ttgatgttgt ctttaggata tagagagcga   1320

agtgttcact ttggcaatca aagatttttg taa                                1353


<210> SEQ ID NO 2
<211> LENGTH: 1353
<212> TYPE: DNA
<213> ORGANISM: Phage from Borrelia burgdorferi

<400> SEQUENCE: 2

gtgaacttat atcaaacaaa actttttaca acactacaaa aggaatacaa aaataaatat     60

ggagttgata tatcacaatt tgtaaagcta acaaattctt caattaattt tgataagttt    120

gaagaaaaac agttaacttt aaaacaaaaa aatgtgataa aaagtattaa aaagaataat    180

gaaaaaaaga ttatattcag cggcggcata gctagcggca aaacgtatct tgcatgctat    240

ctttttctca aaagtttaat tgaaaataaa aagttatatt ctagcgatac gaataatttt    300

attattggga attcacaacg ctcagttgaa gttaatgttt tgggacaatt tgaaaagcta    360

tgtaaacttc ttaaaattcc ttatattcca agacatacaa ataattcata tattctgatt    420

gattcactac gtattaatct atatggtgga gataaggcaa gtgattttga aagatttagg    480

ggaagtaatt cggcacttat ttttgttaat gaggctacaa ctttacacaa gcaaacttta    540

gaggaggtcc taaaaagact aagatgcggg caagaaacta ttatttttga tactaatcct    600

gatcatccag aacactattt taaaaccgat tatattgata atatagcgac atttaagaca    660

tataatttta caacttatga taatgttcta cttagtaaag gatttatcga aacacaagaa    720

aaactctata aagatatacc atcatataaa gcaagagttt tgctaggtga gtggatagca    780

agcactgatt caatttttac acaaataaat attactgatg attatgtatt tactagtcca    840

atagcatatt tagacccagc atttagtgtt ggaggagata acactgcatt atgtgttatg    900

gagcgagttg atgataagta ttatgctttt gtatttcaag accaacgacc agccaatgat    960

ccttatatta tgaatatggt aaagaccgtt atagaaaatt tcaatgtgca tacactgtat   1020

ttagaggata gagataatac aaaaggtgct ggtggattga cccgcgaata catcttacta   1080

agaaataata taagccaata ttttagaatt gttccagtta agccaaagtc taataaattt   1140

agcagaataa caacgttaat tacgccgttt acttataaga aactttacat tacaaagtac   1200

agtagttctt ctgtatttaa tgatatttat tcgtataagg gggatagcaa aacccatgat   1260
```

gatgctcttg atgcaatgtc tgcagcatat ttgatgttgt ctttaggata tagagagcga 1320
agtgttcact ttggcaatca aagatttttg taa 1353

<210> SEQ ID NO 3
<211> LENGTH: 1353
<212> TYPE: DNA
<213> ORGANISM: Phage from Borrelia burgdorferi

<400> SEQUENCE: 3
gtgaacttat atcaaacaaa actttttaca acactacaaa aggaatacaa aaataaatat 60
ggagttgaca tatcacaatt tgtaaagcta acaaattctt caattaattt tgataagttt 120
gaaaaagaac agttaaccat aaaacaaaaa aatgttataa aaagtattca aaaaaataat 180
gaaaagaaga ttatactcag cggcggcata gctagcggca aaacgtatct tgcatgttat 240
ctttttctca aaagtttaat tgaaaataaa aagttatact ctggtgatat taataatttt 300
attattggga attcacaacg ctcagttgaa gttaatgttt tgggacaatt tgaaaagcta 360
tgtaaacttc ttaaaattcc ttatatccca agacatacaa ataattcata tatattaatt 420
gattcacttc gtattaatct atatggagga gataaggcaa gtgattttga aagatttaga 480
ggcagtaatt cggcacttat ttttgttaat gaggctacta ctttacacaa gcaaacttta 540
gaggaggtct taaaaagact taggtgcgga caagaaacta ttatttttga tactaatcct 600
gatcatccag aacactattt taaaaccgat tatattgata atatagcgac atttaagaca 660
tataatttta caacttatga taatgtgcta cttagtaaag gatttatcga aacacaagaa 720
aaactctata aagatatacc atcatataaa gcaagagttt tgctaggtga gtggatagca 780
agcaccgatt caatttttac acaaataaat attactaatg attatgtatt tactagcccg 840
atagcatatt tagacccagc atttagtgtt ggaggggata acactgcatt atgtgttatg 900
gagcgagttg atgataagta ttatgctttt gtatttcaag accaacgacc agccaatgat 960
ccttatatta tgaatatggt aaagaccgtt atagaaaatt tcaatgtgca tacactgtat 1020
ttagaggata gagataatac aaaaggtgct ggtggattga cccgcgaata catcttgcta 1080
agaaataata taagccaata ttttagaatt gttccagtta agccaaagtc taataaattt 1140
agcagaataa caacggtaat tacgccgttt acttataaga aactttacat tacaaagtac 1200
agtagttctt ctgtatttaa tgatatttat tcgtataagg gggatagcaa aacccatgat 1260
gatgctcttg atgcaatgtc tgcagcatat ttgatgttgt ctttaggata tagagagcga 1320
agtgttcact ttggcaatca aagatttttg taa 1353

<210> SEQ ID NO 4
<211> LENGTH: 1353
<212> TYPE: DNA
<213> ORGANISM: Phage from Borrelia burgdorferi

<400> SEQUENCE: 4
gtgaacttat atcaaacaaa actttttaca acactacaaa aggaatacaa aaataaatat 60
ggagttgata tatcacaatt tgtaaagcta acaaattctt caattaattt tgataagttt 120
gaagaaaaac agttaacttt aaaacaaaaa aatgtgataa aaagtattaa aaagaataat 180
gaaaaaaaga ttatactcag cggcggcata gctagcggca aaacgtatct tgcatgctat 240
ctttttctca aaagtttaat tgaaaataaa aagttatatt ctagcgatac gaataatttt 300
attattggga attcacaacg ctcagttgaa gttaatgttt tgggacaatt tgaaaagcta 360

-continued

```
tgtaaacttc ttaaaattcc ttatattcca agacatacaa ataattcata tattctgatt    420

gattcactac gtattaatct atatggtgga gataaggcaa gtgattttga aagatttagg    480

ggaagtaatt cggcacttat ttttgttaat gaggctacaa ctttacacaa gcaaacttta    540

gaggaggtct taaaaagact aagatgcggg caagaaacta ttatttttga tactaatccc    600

gatcatccag aacactattt taaaaccgat tatattgata atatagcgac ctttaagaca    660

tataatttta caacttatga taatgtgcta cttagtaaag gatttgtcga aacacaagaa    720

aagctatata aagatatacc atcatataaa gcaagagttt tgctaggtga gtggatagca    780

agcactgatt caatttttac acaaataaat attactgatg attatgtatt tactagcccg    840

atagcatatt tagacccagc atttagtgtt ggcggggata acactgcatt atgtgttatg    900

gagcgagttg atgataagta ttatgctttt gtatttcaag accaaagacc agctaatgat    960

ccttatatta tgaatatggt aaagactgtt atagaaaatt tcaatgtgca tacactgtat   1020

ttagaggata gagataatac aaaaggtgct ggtggattga cccgtgaata catcttgcta   1080

agaagtaata taagccaata ttttagaatt gttccagtta agccaaagtc taataaattt   1140

agcagaataa caacgttaat tacgccgttt acttacaaaa aactttacat tacaaagtac   1200

agtagttctt ctgtatttaa tgatatttat tcgtataagg gggatagcaa aacccatgat   1260

gatgctcttg atgcaatgtc tgcagcatat ttgatgttgt ctttaggata tagagagcga   1320

agtgttcact ttggcaatca aagatttttg taa                                1353
```

<210> SEQ ID NO 5
<211> LENGTH: 1353
<212> TYPE: DNA
<213> ORGANISM: Phage from Borrelia burgdorferi

<400> SEQUENCE: 5

```
gtgaacttat atcaaacaaa actttttaca acactacaaa aggaatacaa aaataaatat     60

ggagttgata tatcgcaatt tataaagcta acaaattctt caattaattt tgataagttt    120

gaagaagaac agctaacttt aaaacaaaaa aatgtgataa aaagcattaa aaagaataat    180

gaaaagaaga ttatactcag tggaggtata gctagcggca aaacgtatct tgcatgttat    240

ctttttctca aaagtttaat tgaaaataaa aagctatatt ctagcgatac gaataatttc    300

attataggga attcacaacg ttcagttgaa gttaatgttt tgggacaatt tgaaaagcta    360

tgtaaacttc ttaaaattcc ttatattcca agacatacaa ataattcata tattttgatt    420

gattcactac gtattaatct atatggtgga gataaggcaa gtgattttga aagatttagg    480

ggaagtaatt cagcacttat ttttgtgaat gaggctacaa ctttacacaa gcaaacttta    540

gaggaagtct taaaaagact aaggtgtggg caagaaacta ttatttttga tactaacccc    600

gatcatccgg aacactattt taaaaccgat tatattgata atatagcaac ttttaagaca    660

tataatttta caacttatga taatgttcta cttagcaaag gatttatcga aactcaagaa    720

aagctatata aagatatacc atcatataaa gcaagagttt tgctaggtga atggatagca    780

agcaccgatt caatttttac acaaataaat attactaatg attatgtatt tactagcccg    840

atagcatatt tagacccagc atttagtgtt ggaggggata acactgcatt atgtgttatg    900

gagcgagttg atgataagta ttatgctttt gtatttcaag accaaagacc agccaatgac    960

ccgtatatta tgaatatggt taagaccgtt ttagagaatt ttaatgtaca tacactttat   1020

ttagaagata gagacaatac aaaaggtgct ggtggattga ctcgtgaata catgttgcta   1080

agaaataata tgggtcaata ttttagaatt gttccagtta agccaaagtc taataaattt   1140
```

```
agcagaataa caacgttaat tacgccgttt acttataaga aactttacat tacaaagtac   1200

agcagttctt ctgtatttaa tgatatttat tcgtataaag gagataacaa aacccatgat   1260

gatgctcttg atgcaatatc tgcagcatat ttgatgttgt ctttagggta tagagagaga   1320

agtgttcact ttggcaatca aagatttttg taa                                1353
```

<210> SEQ ID NO 6
<211> LENGTH: 1352
<212> TYPE: DNA
<213> ORGANISM: Phage from Borrelia burgdorferi

<400> SEQUENCE: 6

```
gtgaacttat atcaaacaaa actttttaca acactacaaa aggaatacaa aaataaatat     60

ggagttgata tatcacaatt tgtaaagcta acaaattctt caattaattt tgataagttt    120

gaagaagaac agttaacttt aaaacaaaaa aatgtgataa aaagcattaa aaagaataat    180

gaaaagaaga ttatactcag cggaggcata gctagtggca aaacgtatct tgcatgttat    240

ctttttctaa aaagtttaat tgaaaataaa aagttatact ctagtgatac taataatttc    300

attataggga attcacaacg ttcagttgaa gttaatgttt tggggcaatt tgaaaagcta    360

tgtaaacttc ttaaaattcc ttatattcca agacatacaa ataattcata tattctgatt    420

gattcactac gtattaatct atatggagga gataaggcaa gtgattttga aagatttagg    480

ggaagtaatt cggcacttat ttttgttaat gaggctacaa ctttacacaa gcaaacttta    540

gaggaagtct taaaaagact aagatgcggg caagaaacta ttatttttga tactaatcct    600

gatcatccag aacactattt taaaaccgat tatattgata atatagcgac ctttaagaca    660

tataatttac aacttatgat aatgtgctac ttagtaaagg atttgtcgaa acacaagaaa    720

agctatataa agatatacca tcatataaag caagagtttt gttaggtgag tggatagcaa    780

gcactgattc aatttttaca caaataaata ttactgatga ttatgtattt actagcccga    840

tagcatattt agacccagca tttagtgttg gaggggataa cactgcatta tgtgttatgg    900

agcgagttga tgataagtat tatgcttttg tatttcaaga ccaaagacca gctaatgatc    960

cttatattat gaatatggta aagactgtta tagaaaattt caatgtgcat acactgtatt   1020

tagaggatag agataataca aaaggtgctg gtggattgac ccgtgaatac atcttgctaa   1080

gaagtaatat aagccaatat tttagaattg ttccagttaa gccaaagtct aataaattta   1140

gcagaataac aacgttaatt acgccgttta cttacaaaaa actttatatt acaaagtaca   1200

gtagttcttc cgtatttaat gatatttatt cgtataaggg ggataataaa acccatgatg   1260

acgctcttga tgcaatatct gcagcatatt tgatgttgtc tttaggatat agagagcgaa   1320

gtgttcactt tggcaatcaa agatttttgt aa                                 1352
```

<210> SEQ ID NO 7
<211> LENGTH: 1353
<212> TYPE: DNA
<213> ORGANISM: Phage from Borrelia burgdorferi

<400> SEQUENCE: 7

```
gtgaacttat atcaaacaaa actttttaca acactacaaa aggaatacaa aaataaatat     60

ggagttgaca tatcacaatt tgtaaagcta gcaaattctt caattaattt tgataagttt    120

gaagaaaaac agttaacttt aaaacaaaaa aatgtgataa aaagtattaa aaagaataat    180

gaaaaaaaga ttatactcag cggaggcata gctagtggca aaacgtatct tgcatgttat    240
```

-continued

```
cttttctaa aaagtttaat tgaaaataaa aagttatact ctagtgatac taataatttc    300
attattggga attcacaacg ctcagttgaa gttaatgttt taggacaatt tgaaaagcta    360
tgtaaacttc ttaaaattcc ttatatccca agacatacaa ataattcata tattctgatt    420
gattcactac gtattaatct atatggtgga gataaggcaa gtgattttga aagatttagg    480
ggaagtaatt cagcacttat ttttgttaat gaggctacaa ctttacacaa gcaaacttta    540
gaggaggtct taaaaagact aagatgcggg caagaaacta ttatttttga tactaatcct    600
gatcatccag aacactattt taaaaccgat tatattgata atatagcgac atttaagata    660
tataatttta caacttatga taatgtgcta cttagtaaag gatttatcga aacacaagaa    720
aaactctata aagatatacc atcatataaa gcaagagttt tgctaggtga gtggatagca    780
agcactgatt caatttttac acaaataaat attactgatg attatatatt tactagcccg    840
atagcatatt tagacccagc atttagtgtt ggaggggata acactgcatt atgtgttatg    900
gagcgagttg atgataagta ttatgctttt gtatttcaag accaacgacc agccaatgat    960
ccttatatta tgaatatggt aaagaccgtt atagaaaatt tcaatgtgca tacactgtat   1020
ttagaggata gagataatac aaaaggtgct ggtggattga cccgcgaata catcttgcta   1080
agaaataata taagccaata ttttagaatt gttccagtta agccaaagtc taataaattt   1140
agcagaataa caatgttaat tacgccgttt acttacaaaa aactttatat tacaaagtac   1200
agtagttctt ctgtatttaa tgatatttat tcgtataagg gggatagcaa aacccatgat   1260
gatgctcttg atgcaatatc tgcagcatat ttgatgttgt ctttaggata tagagagcga   1320
agtgttcact ttggcaatca aagatttttg taa                                1353
```

<210> SEQ ID NO 8
<211> LENGTH: 1353
<212> TYPE: DNA
<213> ORGANISM: Phage from Borrelia burgdorferi

<400> SEQUENCE: 8

```
gtgaacttat atcaaacaaa actttttaca atactacaaa aggaatacaa aaataaatat     60
ggagttgata tatcacaatt tgtaaagcta acaaattctt caattaattt tgataagttt    120
gaagaagagc agctaacttt aaaacaaaaa aatgtgataa aaagcattaa aaagaataat    180
gaaaaaaaga ttatactcag cggcggcata gctagcggca aaacgtatct tgcatgttat    240
ctttttataa aaagtttaat tgaaaataaa aagctatatt ctagcgatac gaataatttc    300
attataggga attcacaacg ctcagttgaa gttaatgttt tggggcaatt tgaaaagcta    360
tgcaaactgc ttaaaattcc ttatattcca agacatacaa ataattcata tattctgatt    420
gattcactgc gaattaatct acatggtgga gataaggcaa gtgattttga aagatttagg    480
ggaagtaatt cagcacttat ttttgttaat gaggctacaa ctttacacaa gcaaacttta    540
gaggaagtct taaaaagatt aagatgcggg caagaaacta ttatttttga tactaatcct    600
gatcatccag aacactattt taaaaccgat tatattgata atatagcgac ctttaagaca    660
tataatttta caacttatga taatgttcta cttagtaaag gatttatcga aacacaagaa    720
aagctctata aagatatacc atcatataaa gcaagagttt tgctagggga gtggatagca    780
agcaccgatt caatttttac acaaataaat attactaatg attatgtatt tactagcccg    840
atagcatatt tagacccagc atttagtgtt ggcggggata acactgcatt atgtgttatg    900
gagcgggttg atgataagta ttatgctttt gtatttcaag accaacgacc agccaatgac    960
ccgtatatta tgaatatggt taagaccgtt ttagaaaatt ttaatgtaca tacattttat   1020
```

-continued

```
ttagaagata gagacaatac aaaaggtgct ggtggattga cccgcgaata catcttgcta   1080

agaaataata tgggtcaata ttttagaatt gttccagtta agccaaagtc taataaattt   1140

agcagaataa cagcgttaat tacgccgttt atttataaga aactgtacat tacgaagtac   1200

agcagttctt ctgtatttaa tgatatttat tcgtataaag gagataacaa aacccatgat   1260

gatgctcttg atgcaatatc tgcagcatat ttgatgttgt ctttagggta tagagagaga   1320

agtgttcact ttggcaatca aagatttttg taa                                1353
```

<210> SEQ ID NO 9
<211> LENGTH: 1353
<212> TYPE: DNA
<213> ORGANISM: Phage from Borrelia burgdorferi

<400> SEQUENCE: 9

```
ttgaaattct taagatcatt agcgtttctc aatcttcaga aaaagtttaa aaataagttt     60

aatattaaca ttttggatta tattaagcca aaaccaacca aaatttgttt taaagatttt    120

gaaaataaat acttaactgc taagcaaaag gaagttcttt ttgacataga aagtaacaat    180

tattcaaaag taatatttag cggtgggatt gcaagtggta agacgttttt agcttcatat    240

ttgcttgtta aaaagcttat tgaaaacaaa tctttttatg agcaagatac caataatttt    300

attataggca actcaattgg tttgttgatg acaaatactg taaagcaaat agagaaaatt    360

tgcagcttgc tgggaattga ttacgagaaa aagaaaagcg ggcagtcttt ttgtaagata    420

gcaggtctta agcttaatat ttacgggggt aaaaacagag atgctttttc caagattcgt    480

gggggcaata gtgcaataat ttatgtaaat gaagcaacag taattcacag agaaacttta    540

cttgaagtaa taaaaaggct tagaaagggt aaagaaatta ttatttttga tacaaatccg    600

gaaagccctg cgcattattt taaaaccgat tatattgaaa atacagatgt ttttaagaca    660

tataatttta caacttatga caatccttta aattcagcag attttattca aactcaggaa    720

aaactttaca ggcgttttcc cgcctatagg gctcgtgtgc tttacgggga gtggatttta    780

aatgaatcta cgctatttaa tgagatgatt ttcaatcaag attatgaatt taaaagccca    840

ataatgtaca ttgatcctgc attctcagtg ggtggagaca atacagctat ttgtgtttta    900

gagcgcactt ttgagaagtt ttatgcatat atttatcaag accaaaaacc agtaagtgat    960

agtttaatgc ttgcttccat tcaagtttta atagaaaatt tcaatgtaaa taccgtttac   1020

attgaggaga gagacagtac caagggggat ggaattttaa ctaaaacaat tcttttcttg   1080

agaaacaaaa gcagtcacta ttttaaagtt gcaccaataa aaccttttaag caataaattt   1140

aaaagaatat gcgcgcttat tcctttgttt gaaagccgca aaatagaatt tttaaaaata   1200

ataagtaaaa atgtaatatc tgatatttac agctacaaag gagatggcaa aacaaaagac   1260

gatgcgcttg attctcttgc aaatgcgtat cttcttttaa cgctaaatta taaagaaaaa   1320

ttatttcatt tcggcaggtt taaatattta taa                                1353
```

<210> SEQ ID NO 10
<211> LENGTH: 1191
<212> TYPE: DNA
<213> ORGANISM: Phage from Borrelia burgdorferi

<400> SEQUENCE: 10

```
atgagactaa ggcgacttcc agtatatgtt gatgcctaca aagaaaagcc caatgctgaa     60

attttcatat actactcaag taggggaact ggtaaaacct acgacattgc aactgttaat    120
```

-continued

```
ttagaaagaa aatttagtgc tgatggcgga gataccccttg caattagaaa aaagaaaaac    180
aaaacaacac aatcaataca caaagaaatt ttagaacttt taagcatata caacttaaga    240
aaatttttca atataagcaa agcaaaaatt gaaagtaaga gtttgatttt tgggaaaaaa    300
cgtgcttttg tttttgaagg ggggcatgat acaagagatt taaaatctta tgcgcatttt    360
aaggacttat ggctggaaga agccaatcag tttagcgctg atgatataga aatgcttgtc    420
cctacaatga gagaacaagg cggcagaatc tatatgtcaa gcaatccggt gcctaaatca    480
cattggctat acaaaaggta cttatcaaat caagacaatc ctgctgtgtg tataatcaaa    540
agcacttacc gtgacaaccc atttttaaat ggtggagacg tacaagcttg gcttgaaaaa    600
caaagacttg catatcatgg caatgacatt ggttttagaa ttgaggtttt aggagaagag    660
tttgattttg gtacagcaag gctaattaaa aaatttaatg tgtgtggtcc cgaaattctt    720
tccagagcta atggaagcta ttatacagga atacacgtta aaggcaacag aatttgtttt    780
ttagaaattc ttgttggaag aatttcctat cttccagttg taattattac aaacgcatgt    840
agtaaagttt tactatcaaa aactgattac caatccgaaa ttaataaatt taaaggggtt    900
tttgtattgc caacagcaag agaagaactc aaatatgtat tttctcgttt tggtagaggt    960
actttgcttg caaaaaaacg aaacttgtat tcactctcag actatttgat tccgtctaat   1020
cttaatgtgg taaacaaacc cgaaaccact gatgtaattt cagagttcaa cgaaactgaa   1080
tattattatg atgaatctag tgcagaagat agcgaagtta caaattttgt tatgcaaaaa   1140
gatttggtat acatcccggc atttctcaat gccatatcgg tttttagcta a            1191
```

<210> SEQ ID NO 11
<211> LENGTH: 1224
<212> TYPE: DNA
<213> ORGANISM: Phage from Borrelia burgdorferi

<400> SEQUENCE: 11

```
gtgtgtgatt taagaaaaac aaaactaata gataaaataa gttcactaga actatacaaa     60
tactcaatat tttttagaaa ttacattgaa aatgtagcag aagattgtct caagaacgga    120
cttattcttg agagtgctgc ccacaatgtt agtgaggttg aacttgctag gttaaaggta    180
cagcttaaga atgctctgct taattgtatt ataagctacc gttttcatgg gattggctat    240
gttttagtaa aaaccaaaga taccctaata gatctcgaac aacccgttaa tatagaatta    300
cctattggtt ttgaatacct tgattatgaa tatgtaagag atttgggagt tgattttgat    360
catataacct ataaagtaaa atccaacaat aagaacaatt ctttagacgc agttaaaata    420
cataaaagtc gacttatcat atatgaaaac tttgattata tcttaaaaag atatgttccg    480
tgttataccg aaagcttttt actagatatt tatttatttg aaaagatata cgtagaaata    540
gaaagacgta ttgaaaacca caatttcttg ttttataaag atgaatcttt agtacaacta    600
caagacgcac tctctagtgc aacaacttct ttaagtgcac ttactcagag caataatgat    660
aggggaagtg gcattttatc ttcttttttg agaaaacaaa attcaaacaa tcatagtaaa    720
gatatttcta atttaagaaa ccttaatgac tcattatcac aggagcttgc taggctaaaa    780
agcaatctaa ataatgaggg aatgttttat acggccaccc ctagtgctag tttagaggtt    840
attaaatacg atcttagcta cttaaaggag gctttagcat taattaaggc aaaaaattggt    900
gcagatacta aagagccctt aaccagaagt tttaatgagc aggctaaagg actaggaaat    960
gatggtaaag gtgataggag taattattac gattttctca aaggtgtaca agaacaagtt   1020
gagaactctt gtaatttaaa acttacaaag tattttgggc ttgatatgaa gtttaattct   1080
```

ctgattatgt taagtgaaga acaaaaagtg gaaagagata taaagctaat tgagctttac 1140
agtaaatata accagcttat acaaagtagc tcatttaata atgaggagct agcgatgtta 1200
aaagagaaat tattctcatt ttga 1224

<210> SEQ ID NO 12
<211> LENGTH: 1224
<212> TYPE: DNA
<213> ORGANISM: Phage from Borrelia burgdorferi

<400> SEQUENCE: 12
gtgtgtgatt taagaaaaac aaaactaata gataaaataa gttcactaga actatacaaa 60
tactcaatat tttttagaaa ttacattgaa aatgtagcag aagattgtct caagaacgga 120
cttattcttg agagtgctgc ccacaatgtt agtgaggttg aacttgctag gttaaaggta 180
cagcttaaga atgctctgct taattgtatt ataagctacc gttttcatgg gattggctat 240
gttttagtaa aaaccaaaga taccctaata gatctcgaac aacccgttaa tatagaatta 300
cctattggtt ttgaatacct tgattatgaa tatgtaagag atttgggagt tgattttgat 360
catataacct ataaagtaaa atccaacaat aagaacaatt ctttagatgc agttaaaata 420
cataaaagtc gacttatcat atatgaaaac tttgattata tcttaaaaag atatgttccg 480
tgctataccg aaagcttttt actagatatt tatttatttg aaaagatata cgtagaaata 540
gaaagacgta ttgaaaacca caattttttg ttttacaaag atgaatcttt agtacaacta 600
caagacgcac tttctagtgc aacaacttct ttaagtgcac ttactcagag caataatgat 660
aggggaagtg gcattttatc ttcttttttg agaaaacaaa attcaaacaa tcatagtaaa 720
gatatttcta atttaagaaa ccttaatgac tcattgtcac aggagcttgc caggctaaaa 780
agcaatctaa ataatgaggg aatgttttat acagctactc ctagtgctag tttagaggtt 840
attaaatacg atcttagtta cttaaaggag gctttagcat taattaaggc aaaaaattggt 900 gcagatacta aagagccctt aaccagaagt tttaatgaac aggctaaagg actgggaaat 960
gatggtaaag gtgataggag taattattac gattttctca aaggtgtaca agaacaagtt 1020
gagaactctt gtaatttaaa acttacaaag tattttggac ttgatatgaa gtttaattcg 1080
ctgattatgt taagtgaaga acaaaaagta gaaagagata taaagctaat tgagctttac 1140
agtaaatata accagcttat acaaagtagc tcatttaata atgaggagct agcgatgtta 1200
aaagagaaat tattctcatt ttga 1224

<210> SEQ ID NO 13
<211> LENGTH: 1224
<212> TYPE: DNA
<213> ORGANISM: Phage from Borrelia burgdorferi

<400> SEQUENCE: 13
gtgtgtgatt taagaaaaac aaaactaata gataaaataa gttcactaga actatacaaa 60
tactcaatat tttttagaaa ttacattgaa aatgtagcag aagattgtct caagaacgga 120
cttattcttg agagtgctgc tcacaatgtt agtgaggttg aacttgctag gttaaaggta 180
cagcttaaga atgctctgct taattgtatt ataagctacc gttttcatgg gattggctat 240
gttttagtaa aaaccaaaga taccctaata gatctcgaac aacccgttaa tatagaatta 300
cctattggtt ttgaatacct tgattatgaa tatgtaagag atttgggagt tgattttgat 360
catataacct ataaagtaaa atccaacaat aagaacaatt ctttagacgc agttaaaata 420

-continued

```
cataaaagtc gacttatcat atatgaaaac tttgattata tcttaaaaag atatgttccg    480
tgttataccg aaagcttttt actagatatt tatttatttg aaaagatata cgtagaaata    540
gaaagacgta ttgaaaacca caattttttg ttttacaaag atgaatcttt agtacaacta    600
caagacgcac tttctagtgc aacaacttct ttaagtgcac ttactcagag caataatgat    660
aggggaagtg gcattttatc ttcttttttg agaaaacaaa attcaaacaa tcatagtaaa    720
gatatttcta atttaagaaa ccttaatgac tcattatcac aggagcttgc taggctaaaa    780
agcaatctaa ataatgaggg aatgttttat acggccaccc ctagtgctag tttagaggtt    840
attaaatacg atcttagcta cttaaaggag gctttagcat taattaaggc aaaaattggt    900
gcagatacta aagagccctt aaccagaagt tttaatgagc aggctaaagg gctaggaaat    960
gatggtaaag gtgataggag taattattac gattttctca aaggtgtaca agaacaagtt   1020
gagaactctt gtaatttaaa acttacaaag tattttgggc ttgatatgaa gtttaattcg   1080
ctgattatgt taagtgaaga acaaaaagta gagagagata taaagctaat tgagctttac   1140
agtaaatata accagcttat acaaagtagc tcatttaata atgaggagct agcgatgtta   1200
aaagagaaat tattctcatt ttga                                          1224
```

```
<210> SEQ ID NO 14
<211> LENGTH: 1224
<212> TYPE: DNA
<213> ORGANISM: Phage from Borrelia burgdorferi

<400> SEQUENCE: 14

gtgtgtgatt taagaaaaac aaaactaata gataaaataa gttcactaga actatacaaa     60
tactcaatat tttttagaaa ttacattgaa aatgtagcag aagattgtct caagaacgga    120
cttattcttg agagtgctgc ccacaatgtt agtgaggttg aacttgctag gttaaaggta    180
cagcttaaga atgctctgct taattgtatt ataagctacc gttttcatgg gattggctat    240
gttttagtaa aaaccaaaga taccctaata gatctcgaac aacccgttaa tatagaatta    300
cctattggtt ttgaatacct tgattatgaa tatgtaagag atttgggagt tgattttgat    360
catataacct ataaagtaaa atccaacaat aagaacaatt ctttagacgc agttaaaata    420
cataaaagtc gacttatcat atatgaaaac tttgattata tcttaaaaag atatgttccg    480
tgttataccg aaagcttttt actagatatt tatttatttg aaaagatata cgtagaaata    540
gaaagacgta ttgaaaacca caatttcttg ttttataaag atgaatcttt agtacaacta    600
caagacgcac tctctagtgc aacaacttct ttaagtgcac ttactcagag caataatgat    660
aggggaagtg gcattttatc ttcttttttg agaaaacaaa attcaaacaa tcatagtaaa    720
gatatttcta atttaagaaa ccttaatgac tcattatcac aggagcttgc taggctaaaa    780
agcaatctaa ataatgaggg aatgttttat acggccaccc ctagtgctag tttagaggtt    840
attaaatacg atcttagcta cttaaaggag gctttagcat taattaaggc aaaaattggt    900
gcagatacta aagagccctt aaccagaagt tttaatgagc aggctaaagg actaggaaat    960
gatggtaaag gtgataggag taattattac gattttctca aaggtgtaca agaacaagtt   1020
gagaactctt gtaatttaaa acttacaaag tattttgggc ttgatatgaa gtttaattct   1080
ctgattatgt taagtgaaga acaaaaagtg gaaagagata taaagctaat tgagctttac   1140
agtaaatata accagcttat acaaagtagc tcatttaata atgaggagct agcgatgtta   1200
aaagagaaat tattctcatt ttga                                          1224
```

<210> SEQ ID NO 15
<211> LENGTH: 1227
<212> TYPE: DNA
<213> ORGANISM: Phage from Borrelia burgdorferi

<400> SEQUENCE: 15
atgattaacg aatttaaaat ggaaataaaa aacaataaat ccaaaatcaa tcctattgat 60
gtttacagat attcaatttt ttttagaaac tacatagaaa gtaccgcaga agatgcactt 120
aagaatggaa ttaatttaag cctgcttgaa aagtcttgct tgaaagaaag cagcaagtct 180
cttttggggt taaaggttca gttaaaagaa gctcttcttg aagcaatgat aagctacaga 240
tttaatggag caggttatat tttggtaaaa cccaaaagtg aagatgaaga tttaagcaaa 300
aaggttaaca gcgaattacc cacaggtttt aaatatttgg attttcaaaa aattattaac 360
aaaagagatt ctagttacgt ggagtacctt tctaactcaa aagacccgga tgattttgag 420
agagcaagag ttgtaaaaat agataaaagc agagtaataa tttatgaaaa ttatgattat 480
gttttaggcg agcaagaacc tgcttacacg caaagtttgc tgcttaacat ttgtctttta 540
gaacaaattt atttagaaat agaaaaaaga ataagaaatt ataatttttt gttttacaaa 600
gacgaacatt tggtgggact tgttgaatct ttagagattg caaaagaaga aattaatgtt 660
ttggcaaaca gcaaaggcaa aatattttct accttttta aagctcaaga gccaaacaaa 720
agttttcaag cattaagtag cgtctctgac gagcttagca gagagcttag caagattaaa 780
aacactctaa acaatgatgg aattttttac acagcatcag agaatgcacg cctagaagta 840
ataaaatatg atttagagtt tttaaaagac gcatttgaac ttgttaaagc aaaaattggc 900
gctgatacca aagagccttt aaccagaagc tttaatgagc aagtcaaagg gcttggcagc 960
agcggcaagg gagataaaag caattattat gattatttaa aaggcgttca agaatctgtt 1020
gctaatgcgt gcaatctcaa gcttaacaaa tattacagat taaatatgaa gtttaatgag 1080
cttgaagctt taagctatga gcaaagactt caaaaagaca atttgcttct tgatgtttat 1140
tttaaatatt tagagctaat taaaaatgaa aatctaagcg acaaggcaaa agaaaattta 1200
aaagaacaat taagtttggt tatttaa 1227

<210> SEQ ID NO 16
<211> LENGTH: 777
<212> TYPE: DNA
<213> ORGANISM: Phage from Borrelia burgdorferi

<400> SEQUENCE: 16
atgaacacta ataattattt taatttaaat aatttcaaca tggattttat gctcaaacta 60
tttcaagatt atcaaaatgt gctaaatgaa aataaaattc ttaaaaattc actaaaaatt 120
tcttctaagc ctactaaaaa agcttcaaaa ccaactccta agttttattt gaccccaaaa 180
gctatcaaaa taattgaaaa atgcgttaaa atattaaaaa aaattgaccc tatttctggt 240
tggtttctac atctactcgc aataagtggg tgtagggggg ccgaaattca aaaagtaaaa 300
atgcaagata ttactcctct attaaacaaa actggagaaa ctttttacaa tataaaagtt 360
aatatagcta aaaaaagaaa tgtcacttgt attagagaaa ttgtcatcaa atctgaagaa 420
tttgaggcta ttcaaaaagc tcacgaaaat tattttaacg aaaaaaatct tgactcacgg 480
cgtacttatc ttttccaaaa aaccaaacat aaatttaaag ataaccaaat tgatattatc 540
aatatttcta gaaaatttaa aaatcttctc aaaaaatcag gatttcgtgc caataaatct 600
ctccatttat ttagaaattt gtttatttca tatttaaaat ctaatggtta taattctttc 660

-continued caaattaaag aacttatgaa atatcattca acttccgaaa ttgataatat ctacggcctc 720
tctgctgcta ataaaattca cgcttataaa tgcatgaaaa ataaccttaa actttag 777

<210> SEQ ID NO 17
<211> LENGTH: 204
<212> TYPE: DNA
<213> ORGANISM: Phage from Borrelia burgdorferi

<400> SEQUENCE: 17
atggatacta ttaaattaac cgaacttctt atcaatttaa acgaaattaa acttatagcg 60
gtaatgattt ttgtaacagt gctggtttta ggagtattaa ttcttctcaa gcctttacta 120
aaagacatat tgactattgt aataggcaag atttttaaga atggtaatgg taatggcaaa 180
aatcacatta aaaaaagaga ttaa 204

<210> SEQ ID NO 18
<211> LENGTH: 204
<212> TYPE: DNA
<213> ORGANISM: Phage from Borrelia burgdorferi

<400> SEQUENCE: 18
atggatacta ttaaattaac cgaacttctt atcaatttaa acgaaattaa acttatagcg 60
gtaatgattt ttgtaacagt gctggtttta ggagtattaa ttcttctcaa gcctttacta 120
aaagacatat tgactattgt aataggcaag atttttaaga atggtaatgg taatggcaaa 180
aatcacatta aaaaaagaga ttaa 204

<210> SEQ ID NO 19
<211> LENGTH: 204
<212> TYPE: DNA
<213> ORGANISM: Phage from Borrelia burgdorferi

<400> SEQUENCE: 19
atggatacta ttaaattaac agaacttctt atcaatttaa acgaaattaa acttatagcc 60
gtaatgattt ttgtaacagt gttggtttta ggagtattaa ttcttctcaa gcctttacta 120
aaagacatat tgactattgt aataggcaag atttttaaga atggtaatgg taatggcaaa 180
aatcacatta aaaaaagaga ttaa 204

<210> SEQ ID NO 20
<211> LENGTH: 204
<212> TYPE: DNA
<213> ORGANISM: Phage from Borrelia burgdorferi

<400> SEQUENCE: 20
atggatacta ttaaattaac cgaacttctt atcaatttaa acgaaattaa acttatagcg 60
gtaatgattt ttgtaacagt gctggtttta ggagtattaa ttcttctcaa gcctttacta 120
aaagacatat tgactattgt aataggcaag atttttaaga atggtaatgg taatggcaaa 180
aatcacatta aaaaaagaga ttaa 204

<210> SEQ ID NO 21
<211> LENGTH: 204
<212> TYPE: DNA
<213> ORGANISM: Phage from Borrelia burgdorferi

<400> SEQUENCE: 21
atggatacta ttaaattaac cgaacttctt atcaatttaa acgaaattaa acttatagcg 60
gtaatgattt ttgtaacagt gctggtttta ggagtattaa ttcttctcaa gcctttacta 120
aaagacatat tgactattgt aataggcaag atttttaaga atggtaatgg taatggcaaa 180
aatcacatta aaaaaagaga ttaa 204

<210> SEQ ID NO 22
<211> LENGTH: 204
<212> TYPE: DNA
<213> ORGANISM: Phage from Borrelia burgdorferi

<400> SEQUENCE: 22
atggatacta ttaaattaac cgaacttctt atcaatttaa acgaaattaa acttatagcg 60
gtaatgattt ttgtaacagt gctggtttta ggagtattaa ttcttctcaa gcctttacta 120
aaagacatat tgactattgt aataggcaag atttttaaga atggtaatgg taatggcaaa 180
aatcacatta aaaaaagaga ttaa 204

<210> SEQ ID NO 23
<211> LENGTH: 204
<212> TYPE: DNA
<213> ORGANISM: Phage from Borrelia burgdorferi

<400> SEQUENCE: 23
atggatacta ttaaattaac agaacttctt atcaatttaa atgaaattaa acttatagcc 60
gtaatgattt ttgtaacagt attggtttta ggagtgttaa ttcttctcaa gcctttatta 120
aaagacatat tgactattgt aataggcaag atttttaaga atggcaatgg taatggcaaa 180
aatcacatta aaaaaagaga ttaa 204

<210> SEQ ID NO 24
<211> LENGTH: 204
<212> TYPE: DNA
<213> ORGANISM: Phage from Borrelia burgdorferi

<400> SEQUENCE: 24
atggatacta ttaaattaac agaacttctt atcaatttaa acgaaattaa acttatagcc 60
gtaatgattt ttgtaacagt gttggtttta ggagtattaa ttcttctcaa gcctttacta 120
aaagacatat tgactattgt aataggcaag atttttaaga atggtaatgg taatggcaaa 180
aatcacatta aaaaaagaga ttaa 204

<210> SEQ ID NO 25
<211> LENGTH: 180
<212> TYPE: DNA
<213> ORGANISM: Phage from Borrelia burgdorferi

<400> SEQUENCE: 25
atggatacaa tacttatttt tttgtcaaca attgacaata caaaactaat tatcttagga 60
ggatttattg tgctggtaat aatgccgatg attttggcaa taaaaccaca gtttagagaa 120
aatttaattt tgcttattca aaaactctta aaaaatataa ataaaaagga aaaaaaatga 180

<210> SEQ ID NO 26
<211> LENGTH: 348
<212> TYPE: DNA
<213> ORGANISM: Phage from Borrelia burgdorferi

<400> SEQUENCE: 26
atgaaattat ccaaagataa tgttgagctt ggacttacgt ctttatcaac ccttattgat 60
atattttcta aatttgaaga tgaatttgat gaaattgcac ataaaggatt ctttttggtt 120

-continued

```
tatgagctgt attctcatta taaattaatc tatacagcaa atatggaaag acttgagagt    180

gcattaaccc cagcaataaa taaagcactc gctccattaa atgaaaaaat caatcaatgc    240

attgacttag ttaattctga tgaaaaaaat ctcaaaatat ctaatgatct gaaattcaat    300

caggaaggaa aacctatcta taaggaaaga acaaataatg caaaataa                  348


<210> SEQ ID NO 27
<211> LENGTH: 348
<212> TYPE: DNA
<213> ORGANISM: Phage from Borrelia burgdorferi

<400> SEQUENCE: 27

atgaaattat ccaaagataa tgttgagctt ggacttacgt ctttatcaac ccttattgat     60

atattttcta aatttgaaga tgaatttgat gaaattgcac ataaaggatt ctttttggtt    120

tatgagctgt attctcatta taaattaatc tatacagcaa atatggaaag acttgagagt    180

gcattaaccc cagcaataaa taaagcactc gctccattaa atgaaaaaat caatcaatgc    240

attgacttag ttaattctga tgaaaaaaat ctcaaaatat ctaatgatct gaaattcaat    300

caggaaggaa aacctatcta taaggaaaga acaaataatg caaaataa                  348


<210> SEQ ID NO 28
<211> LENGTH: 348
<212> TYPE: DNA
<213> ORGANISM: Phage from Borrelia burgdorferi

<400> SEQUENCE: 28

atgaaattat ccaaagataa tgttgagctt ggacttacgt ctttatcaac ccttattgat     60

atattttcta aatttgaaga tgaatttgat gaaattgcac ataaaggatt ctttttggtt    120

tatgagctgt attctcatta taaattaatc tatacagcaa atatggaaag acttgagagt    180

gcattaaccc cagcaataaa taaagcactc gctccattaa atgaaaaaat caatcaatgc    240

attgacttag ttaattctga tgaaaaaaat ctcaaaatat ctaatgatct gaaattcaat    300

caggaaggaa aacctatcta taaggaaaga acaaataatg caaaataa                  348


<210> SEQ ID NO 29
<211> LENGTH: 348
<212> TYPE: DNA
<213> ORGANISM: Phage from Borrelia burgdorferi

<400> SEQUENCE: 29

atgaaattat ccaaagataa tgttgagctt ggacttacgt ctttatcaac ccttattgat     60

atattttcta aatttgaaga tgaatttgat gaaattgcac ataaaggatt ctttttggtt    120

tatgatctgt attctcatta caaattaatc tatacagcaa atatggaaag acttgagagt    180

gcattaaccc cagcaataaa tgcggcactc gctccattaa atgaaaaaat caatcaatgc    240

attgacttag ttaattctga tgaaaaaaat ctcaaaatat ctaatgatct gaaattcaat    300

caggaaggaa aacctatcta taaggaaaga ataaataatg caaaataa                  348


<210> SEQ ID NO 30
<211> LENGTH: 357
<212> TYPE: DNA
<213> ORGANISM: Phage from Borrelia burgdorferi

<400> SEQUENCE: 30

atgaaattat ccaaagataa tgttgagctt ggacttacgt ctttatcaac ccttattgat     60

atattttcta aatttgaaga tgaatttgat gaaattgcac ataaaggatt ctttttggtt    120
```

```
tatgagctgt attctcatta taaattaatc tatacagcaa atatggaaag acttgagagt    180

gcattaaccc cagcaataaa tgcggcactc gctcctttaa atgcaaaaat caatacggtt    240

attgatttgg ttaattctaa tgataaaaat ctaaaaatat ccaatgatct aaaattcaat    300

aaagacggaa aacctatcta caaagagaga gcaaataatg caaaagaaca ctattga       357
```

<210> SEQ ID NO 31
<211> LENGTH: 348
<212> TYPE: DNA
<213> ORGANISM: Phage from Borrelia burgdorferi

<400> SEQUENCE: 31

```
atgaaattat ccaaagataa tgttgagctt ggacttacgt ctttatcaac ccttattgat     60

atattttcta aatttgaaga tgaatttgat gaaattgcac ataaaggatt ctttttggtt    120

tatgagctgt attctcatta taaattaatc tatacagcaa atatggaaag acttgagagt    180

gcattaaccc cagcaataaa tgcggcactc gctccattaa atgaaaaaat caatcaatgc    240

attgacttag ttaattctga tgaaaaaaat ctcaaaatat ctaatgatct gaaattcaat    300

caggaaggaa aacctatcta taaggaaaga acaaataatg caaaataa                 348
```

<210> SEQ ID NO 32
<211> LENGTH: 348
<212> TYPE: DNA
<213> ORGANISM: Phage from Borrelia burgdorferi

<400> SEQUENCE: 32

```
atgaaattat ccaaagataa tgttgagctt ggacttacgt ctttatcaac ccttattgat     60

atattttcta aatttgaaga tgaatttgat gaaattgcac ataaaggatt ctttttggtt    120

tatgagctgt attctcatta taaattaatc tatacagcaa atatggaaag acttgagagt    180

gcattaaccc cagcaataaa tgcggcactc gctccattaa atgaaaaaat caatcaatgc    240

attgacttag ttaattctga tgaaaaaaat ctcaaaatat ctaatgatct gaaattcaat    300

caggaaggaa aacctatcta taaggaaaga acaaataatg caaaataa                 348
```

<210> SEQ ID NO 33
<211> LENGTH: 348
<212> TYPE: DNA
<213> ORGANISM: Phage from Borrelia burgdorferi

<400> SEQUENCE: 33

```
atgaaattat ccaaagataa tgttgagctt ggacttacgt ctttatcaac ccttattgat     60

atattttcta aatttgaaga tgaatttgat gaaattgcac ataaaggatt ctttttggtt    120

tatgagctgt attctcatta taaattaatc tatacagcaa atatggaaag acttgagagt    180

gcattaaccc cagcaataaa taaagcacta gctccattaa atgaaaaaat caatcaatgc    240

attgacttag ttaattctga tgaaaaaaat ctcaaaatat ctaatgatct gaaattcaat    300

caggaaggaa aacctatcta taaggaaaga acaaataatg caaaataa                 348
```

<210> SEQ ID NO 34
<211> LENGTH: 426
<212> TYPE: DNA
<213> ORGANISM: Phage from Borrelia burgdorferi

<400> SEQUENCE: 34

```
atgaacaata aaatgaatat caactctggc attgacgctt taaataattt atatgatttt     60
```

-continued

```
ctaaaaagta gcgattctcc aacagaagtc aaagtagaaa agggtatata tttggggctt    120

aatctttaca atctaataat gagcatctac aaagacaaaa tcacaaccct tgagaaagaa    180

gaatcattaa aaatattaaa tgaaattaaa aatgttaata ataagattac tcaacttata    240

tcaagcatta atgatgagag agatgcaagc atcattgaac atttaagaga agagagaaat    300

gaactaatgt caatcaaaac tcaagcactc caagaacaaa taaaagagtt tccagaaaat    360

acaagcactg ctaacagcaa agcccaaaac ttaaaagaaa ataaaggaga taaaattgca    420

aattaa                                                               426


<210> SEQ ID NO 35
<211> LENGTH: 147
<212> TYPE: DNA
<213> ORGANISM: Phage from Borrelia burgdorferi

<400> SEQUENCE: 35

gagtggatag caagcactga ttcaattttt acacaaataa atattactga tgattatgta     60

tttactagcc cgatagcata tttagaccca gcatttagtg ttggcgggga taacactgca    120

ttatgtgtta tggagcgagt tgatgat                                        147


<210> SEQ ID NO 36
<211> LENGTH: 450
<212> TYPE: PRT
<213> ORGANISM: Phage from Borrelia burgdorferi

<400> SEQUENCE: 36

Met Asn Leu Tyr Gln Thr Lys Leu Phe Thr Thr Leu Gln Lys Glu Tyr
1               5                   10                  15

Lys Asn Lys Tyr Gly Val Asp Ile Ser Gln Phe Val Lys Leu Thr Asn
            20                  25                  30

Ser Ser Ile Asn Phe Asp Lys Phe Glu Glu Glu Gln Leu Thr Leu Lys
        35                  40                  45

Gln Lys Asn Val Ile Lys Ser Ile Lys Lys Asn Asn Glu Lys Lys Ile
    50                  55                  60

Ile Leu Ser Gly Gly Ile Ala Ser Gly Lys Thr Tyr Leu Ala Cys Tyr
65                  70                  75                  80

Leu Phe Leu Lys Ser Leu Ile Glu Ile Lys Lys Leu Tyr Ser Ser Asp
                85                  90                  95

Thr Asn Asn Phe Ile Ile Gly Asn Ser Gln Arg Ser Val Glu Val Asn
            100                 105                 110

Val Leu Gly Gln Phe Glu Lys Leu Cys Lys Leu Leu Lys Ile Pro Tyr
        115                 120                 125

Ile Pro Arg His Thr Asn Asn Ser Tyr Ile Leu Ile Asp Ser Leu Arg
    130                 135                 140

Ile Asn Leu Tyr Gly Gly Asp Lys Ala Ser Asp Phe Glu Arg Phe Arg
145                 150                 155                 160

Gly Ser Asn Ser Ala Leu Ile Phe Val Asn Glu Ala Thr Thr Leu His
                165                 170                 175

Lys Gln Thr Leu Glu Glu Val Leu Lys Arg Leu Arg Cys Gly Gln Glu
            180                 185                 190

Thr Ile Ile Phe Asp Thr Asn Pro Asp His Pro Glu His Tyr Phe Lys
        195                 200                 205

Thr Asp Tyr Ile Asp Asn Ile Ala Thr Phe Lys Thr Tyr Lys Phe Thr
    210                 215                 220

Thr Tyr Asp Asn Val Leu Leu Ser Lys Gly Phe Val Glu Thr Gln Glu
```

```
225                 230                 235                 240

Lys Leu Tyr Lys Asp Ile Pro Ser Tyr Lys Ala Arg Val Leu Leu Gly
                245                 250                 255

Glu Trp Ile Ala Ser Thr Asp Ser Ile Phe Thr Gln Ile Asn Ile Thr
            260                 265                 270

Asp Asp Tyr Val Phe Thr Ser Pro Ile Ala Tyr Leu Asp Pro Ala Phe
        275                 280                 285

Ser Val Gly Gly Asp Asn Thr Ala Leu Cys Val Met Glu Arg Val Asp
    290                 295                 300

Asp Lys Tyr Tyr Ala Phe Val Phe Gln Asp Gln Arg Pro Ala Asn Asp
305                 310                 315                 320

Pro Tyr Ile Met Asn Met Val Lys Thr Val Ile Glu Asn Phe Asn Val
                325                 330                 335

His Thr Leu Tyr Leu Glu Asp Arg Asp Asn Thr Lys Gly Ala Gly Gly
            340                 345                 350

Leu Thr Arg Glu Tyr Ile Leu Leu Arg Ser Asn Ile Ser Gln Tyr Phe
        355                 360                 365

Arg Ile Val Pro Val Lys Pro Lys Ser Asn Lys Phe Ser Arg Ile Thr
    370                 375                 380

Thr Leu Ile Thr Pro Phe Thr Tyr Lys Lys Leu Tyr Ile Thr Lys Tyr
385                 390                 395                 400

Ser Ser Ser Ser Val Phe Asn Asp Ile Tyr Ser Tyr Lys Gly Asp Asn
                405                 410                 415

Lys Thr His Asp Asp Ala Leu Asp Ala Ile Ser Ala Ala Tyr Leu Met
            420                 425                 430

Leu Ser Leu Gly Tyr Arg Glu Arg Ser Val His Phe Gly Asn Gln Arg
        435                 440                 445

Phe Leu
    450


<210> SEQ ID NO 37
<211> LENGTH: 450
<212> TYPE: PRT
<213> ORGANISM: Phage from Borrelia burgdorferi

<400> SEQUENCE: 37

Met Asn Leu Tyr Gln Thr Lys Leu Phe Thr Thr Leu Gln Lys Glu Tyr
1               5                   10                  15

Lys Asn Lys Tyr Gly Val Asp Ile Ser Gln Phe Val Lys Leu Thr Asn
            20                  25                  30

Ser Ser Ile Asn Phe Asp Lys Phe Glu Glu Lys Gln Leu Thr Leu Lys
        35                  40                  45

Gln Lys Asn Val Ile Lys Ser Ile Lys Lys Asn Asn Glu Lys Lys Ile
    50                  55                  60

Ile Phe Ser Gly Gly Ile Ala Ser Gly Lys Thr Tyr Leu Ala Cys Tyr
65                  70                  75                  80

Leu Phe Leu Lys Ser Leu Ile Glu Asn Lys Lys Leu Tyr Ser Ser Asp
                85                  90                  95

Thr Asn Asn Phe Ile Ile Gly Asn Ser Gln Arg Ser Val Glu Val Asn
            100                 105                 110

Val Leu Gly Gln Phe Glu Lys Leu Cys Lys Leu Leu Lys Ile Pro Tyr
        115                 120                 125

Ile Pro Arg His Thr Asn Asn Ser Tyr Ile Leu Ile Asp Ser Leu Arg
    130                 135                 140
```

-continued

Ile Asn Leu Tyr Gly Gly Asp Lys Ala Ser Asp Phe Glu Arg Phe Arg
145 150 155 160

Gly Ser Asn Ser Ala Leu Ile Phe Val Asn Glu Ala Thr Thr Leu His
165 170 175

Lys Gln Thr Leu Glu Glu Val Leu Lys Arg Leu Arg Cys Gly Gln Glu
180 185 190

Thr Ile Ile Phe Asp Thr Asn Pro Asp His Pro Glu His Tyr Phe Lys
195 200 205

Thr Asp Tyr Ile Asp Asn Ile Ala Thr Phe Lys Thr Tyr Asn Phe Thr
210 215 220

Thr Tyr Asp Asn Val Leu Leu Ser Lys Gly Phe Ile Glu Thr Gln Glu
225 230 235 240

Lys Leu Tyr Lys Asp Ile Pro Ser Tyr Lys Ala Arg Val Leu Leu Gly
245 250 255

Glu Trp Ile Ala Ser Thr Asp Ser Ile Phe Thr Gln Ile Asn Ile Thr
260 265 270

Asp Asp Tyr Val Phe Thr Ser Pro Ile Ala Tyr Leu Asp Pro Ala Phe
275 280 285

Ser Val Gly Gly Asp Asn Thr Ala Leu Cys Val Met Glu Arg Val Asp
290 295 300

Asp Lys Tyr Tyr Ala Phe Val Phe Gln Asp Gln Arg Pro Ala Asn Asp
305 310 315 320

Pro Tyr Ile Met Asn Met Val Lys Thr Val Ile Glu Asn Phe Asn Val
325 330 335

His Thr Leu Tyr Leu Glu Asp Arg Asp Asn Thr Lys Gly Ala Gly Gly
340 345 350

Leu Thr Arg Glu Tyr Ile Leu Leu Arg Asn Asn Ile Ser Gln Tyr Phe
355 360 365

Arg Ile Val Pro Val Lys Pro Lys Ser Asn Lys Phe Ser Arg Ile Thr
370 375 380

Thr Leu Ile Thr Pro Phe Thr Tyr Lys Lys Leu Tyr Ile Thr Lys Tyr
385 390 395 400

Ser Ser Ser Ser Val Phe Asn Asp Ile Tyr Ser Tyr Lys Gly Asp Ser
405 410 415

Lys Thr His Asp Asp Ala Leu Asp Ala Met Ser Ala Ala Tyr Leu Met
420 425 430

Leu Ser Leu Gly Tyr Arg Glu Arg Ser Val His Phe Gly Asn Gln Arg
435 440 445

Phe Leu
450

<210> SEQ ID NO 38
<211> LENGTH: 450
<212> TYPE: PRT
<213> ORGANISM: Phage from Borrelia burgdorferi

<400> SEQUENCE: 38

Met Asn Leu Tyr Gln Thr Lys Leu Phe Thr Thr Leu Gln Lys Glu Tyr
1 5 10 15

Lys Asn Lys Tyr Gly Val Asp Ile Ser Gln Phe Val Lys Leu Thr Asn
20 25 30

Ser Ser Ile Asn Phe Asp Lys Phe Glu Lys Glu Gln Leu Thr Ile Lys
35 40 45

Gln Lys Asn Val Ile Lys Ser Ile Gln Lys Asn Asn Glu Lys Lys Ile
50 55 60

Ile Leu Ser Gly Gly Ile Ala Ser Gly Lys Thr Tyr Leu Ala Cys Tyr
65 70 75 80

Leu Phe Leu Lys Ser Leu Ile Glu Asn Lys Lys Leu Tyr Ser Gly Asp
85 90 95

Ile Asn Asn Phe Ile Ile Gly Asn Ser Gln Arg Ser Val Glu Val Asn
100 105 110

Val Leu Gly Gln Phe Glu Lys Leu Cys Lys Leu Leu Lys Ile Pro Tyr
115 120 125

Ile Pro Arg His Thr Asn Asn Ser Tyr Ile Leu Ile Asp Ser Leu Arg
130 135 140

Ile Asn Leu Tyr Gly Gly Asp Lys Ala Ser Asp Phe Glu Arg Phe Arg
145 150 155 160

Gly Ser Asn Ser Ala Leu Ile Phe Val Asn Glu Ala Thr Thr Leu His
165 170 175

Lys Gln Thr Leu Glu Glu Val Leu Lys Arg Leu Arg Cys Gly Gln Glu
180 185 190

Thr Ile Ile Phe Asp Thr Asn Pro Asp His Pro Glu His Tyr Phe Lys
195 200 205

Thr Asp Tyr Ile Asp Asn Ile Ala Thr Phe Lys Thr Tyr Asn Phe Thr
210 215 220

Thr Tyr Asp Asn Val Leu Leu Ser Lys Gly Phe Ile Glu Thr Gln Glu
225 230 235 240

Lys Leu Tyr Lys Asp Ile Pro Ser Tyr Lys Ala Arg Val Leu Leu Gly
245 250 255

Glu Trp Ile Ala Ser Thr Asp Ser Ile Phe Thr Gln Ile Asn Ile Thr
260 265 270

Asn Asp Tyr Val Phe Thr Ser Pro Ile Ala Tyr Leu Asp Pro Ala Phe
275 280 285

Ser Val Gly Gly Asp Asn Thr Ala Leu Cys Val Met Glu Arg Val Asp
290 295 300

Asp Lys Tyr Tyr Ala Phe Val Phe Gln Asp Gln Arg Pro Ala Asn Asp
305 310 315 320

Pro Tyr Ile Met Asn Met Val Lys Thr Val Ile Glu Asn Phe Asn Val
325 330 335

His Thr Leu Tyr Leu Glu Asp Arg Asp Asn Thr Lys Gly Ala Gly Gly
340 345 350

Leu Thr Arg Glu Tyr Ile Leu Leu Arg Asn Asn Ile Ser Gln Tyr Phe
355 360 365

Arg Ile Val Pro Val Lys Pro Lys Ser Asn Lys Phe Ser Arg Ile Thr
370 375 380

Thr Val Ile Thr Pro Phe Thr Tyr Lys Lys Leu Tyr Ile Thr Lys Tyr
385 390 395 400

Ser Ser Ser Ser Val Phe Asn Asp Ile Tyr Ser Tyr Lys Gly Asp Ser
405 410 415

Lys Thr His Asp Asp Ala Leu Asp Ala Met Ser Ala Ala Tyr Leu Met
420 425 430

Leu Ser Leu Gly Tyr Arg Glu Arg Ser Val His Phe Gly Asn Gln Arg
435 440 445

Phe Leu
450

<210> SEQ ID NO 39
<211> LENGTH: 450

<212> TYPE: PRT
<213> ORGANISM: Phage from Borrelia burgdorferi

<400> SEQUENCE: 39

```
Met Asn Leu Tyr Gln Thr Lys Leu Phe Thr Thr Leu Gln Lys Glu Tyr
1               5                   10                  15

Lys Asn Lys Tyr Gly Val Asp Ile Ser Gln Phe Val Lys Leu Thr Asn
            20                  25                  30

Ser Ser Ile Asn Phe Asp Lys Phe Glu Glu Lys Gln Leu Thr Leu Lys
        35                  40                  45

Gln Lys Asn Val Ile Lys Ser Ile Lys Lys Asn Asn Glu Lys Lys Ile
    50                  55                  60

Ile Leu Ser Gly Gly Ile Ala Ser Gly Lys Thr Tyr Leu Ala Cys Tyr
65                  70                  75                  80

Leu Phe Leu Lys Ser Leu Ile Glu Asn Lys Lys Leu Tyr Ser Ser Asp
                85                  90                  95

Thr Asn Asn Phe Ile Ile Gly Asn Ser Gln Arg Ser Val Glu Val Asn
            100                 105                 110

Val Leu Gly Gln Phe Glu Lys Leu Cys Lys Leu Leu Lys Ile Pro Tyr
        115                 120                 125

Ile Pro Arg His Thr Asn Asn Ser Tyr Ile Leu Ile Asp Ser Leu Arg
    130                 135                 140

Ile Asn Leu Tyr Gly Gly Asp Lys Ala Ser Asp Phe Glu Arg Phe Arg
145                 150                 155                 160

Gly Ser Asn Ser Ala Leu Ile Phe Val Asn Glu Ala Thr Thr Leu His
                165                 170                 175

Lys Gln Thr Leu Glu Glu Val Leu Lys Arg Leu Arg Cys Gly Gln Glu
            180                 185                 190

Thr Ile Ile Phe Asp Thr Asn Pro Asp His Pro Glu His Tyr Phe Lys
        195                 200                 205

Thr Asp Tyr Ile Asp Asn Ile Ala Thr Phe Lys Thr Tyr Asn Phe Thr
    210                 215                 220

Thr Tyr Asp Asn Val Leu Leu Ser Lys Gly Phe Val Glu Thr Gln Glu
225                 230                 235                 240

Lys Leu Tyr Lys Asp Ile Pro Ser Tyr Lys Ala Arg Val Leu Leu Gly
                245                 250                 255

Glu Trp Ile Ala Ser Thr Asp Ser Ile Phe Thr Gln Ile Asn Ile Thr
            260                 265                 270

Asp Asp Tyr Val Phe Thr Ser Pro Ile Ala Tyr Leu Asp Pro Ala Phe
        275                 280                 285

Ser Val Gly Gly Asp Asn Thr Ala Leu Cys Val Met Glu Arg Val Asp
    290                 295                 300

Asp Lys Tyr Tyr Ala Phe Val Phe Gln Asp Gln Arg Pro Ala Asn Asp
305                 310                 315                 320

Pro Tyr Ile Met Asn Met Val Lys Thr Val Ile Glu Asn Phe Asn Val
                325                 330                 335

His Thr Leu Tyr Leu Glu Asp Arg Asp Asn Thr Lys Gly Ala Gly Gly
            340                 345                 350

Leu Thr Arg Glu Tyr Ile Leu Leu Arg Ser Asn Ile Ser Gln Tyr Phe
        355                 360                 365

Arg Ile Val Pro Val Lys Pro Lys Ser Asn Lys Phe Ser Arg Ile Thr
    370                 375                 380

Thr Leu Ile Thr Pro Phe Thr Tyr Lys Lys Leu Tyr Ile Thr Lys Tyr
385                 390                 395                 400
```

-continued

```
Ser Ser Ser Ser Val Phe Asn Asp Ile Tyr Ser Tyr Lys Gly Asp Ser
                405                 410                 415

Lys Thr His Asp Asp Ala Leu Asp Ala Met Ser Ala Ala Tyr Leu Met
            420                 425                 430

Leu Ser Leu Gly Tyr Arg Glu Arg Ser Val His Phe Gly Asn Gln Arg
        435                 440                 445

Phe Leu
    450


<210> SEQ ID NO 40
<211> LENGTH: 450
<212> TYPE: PRT
<213> ORGANISM: Phage from Borrelia burgdorferi

<400> SEQUENCE: 40

Met Asn Leu Tyr Gln Thr Lys Leu Phe Thr Thr Leu Gln Lys Glu Tyr
1               5                   10                  15

Lys Asn Lys Tyr Gly Val Asp Ile Ser Gln Phe Ile Lys Leu Thr Asn
            20                  25                  30

Ser Ser Ile Asn Phe Asp Lys Phe Glu Glu Glu Gln Leu Thr Leu Lys
        35                  40                  45

Gln Lys Asn Val Ile Lys Ser Ile Lys Lys Asn Asn Glu Lys Lys Ile
    50                  55                  60

Ile Leu Ser Gly Gly Ile Ala Ser Gly Lys Thr Tyr Leu Ala Cys Tyr
65                  70                  75                  80

Leu Phe Leu Lys Ser Leu Ile Glu Asn Lys Lys Leu Tyr Ser Ser Asp
                85                  90                  95

Thr Asn Asn Phe Ile Ile Gly Asn Ser Gln Arg Ser Val Glu Val Asn
            100                 105                 110

Val Leu Gly Gln Phe Glu Lys Leu Cys Lys Leu Leu Lys Ile Pro Tyr
        115                 120                 125

Ile Pro Arg His Thr Asn Asn Ser Tyr Ile Leu Ile Asp Ser Leu Arg
    130                 135                 140

Ile Asn Leu Tyr Gly Gly Asp Lys Ala Ser Asp Phe Glu Arg Phe Arg
145                 150                 155                 160

Gly Ser Asn Ser Ala Leu Ile Phe Val Asn Glu Ala Thr Thr Leu His
                165                 170                 175

Lys Gln Thr Leu Glu Glu Val Leu Lys Arg Leu Arg Cys Gly Gln Glu
            180                 185                 190

Thr Ile Ile Phe Asp Thr Asn Pro Asp His Pro Glu His Tyr Phe Lys
        195                 200                 205

Thr Asp Tyr Ile Asp Asn Ile Ala Thr Phe Lys Thr Tyr Asn Phe Thr
    210                 215                 220

Thr Tyr Asp Asn Val Leu Leu Ser Lys Gly Phe Ile Glu Thr Gln Glu
225                 230                 235                 240

Lys Leu Tyr Lys Asp Ile Pro Ser Tyr Lys Ala Arg Val Leu Leu Gly
                245                 250                 255

Glu Trp Ile Ala Ser Thr Asp Ser Ile Phe Thr Gln Ile Asn Ile Thr
            260                 265                 270

Asn Asp Tyr Val Phe Thr Ser Pro Ile Ala Tyr Leu Asp Pro Ala Phe
        275                 280                 285

Ser Val Gly Gly Asp Asn Thr Ala Leu Cys Val Met Glu Arg Val Asp
    290                 295                 300

Asp Lys Tyr Tyr Ala Phe Val Phe Gln Asp Gln Arg Pro Ala Asn Asp
```

-continued 305 310 315 320

Pro Tyr Ile Met Asn Met Val Lys Thr Val Leu Glu Asn Phe Asn Val
325 330 335

His Thr Leu Tyr Leu Glu Asp Arg Asp Asn Thr Lys Gly Ala Gly Gly
340 345 350

Leu Thr Arg Glu Tyr Met Leu Leu Arg Asn Asn Met Gly Gln Tyr Phe
355 360 365

Arg Ile Val Pro Val Lys Pro Lys Ser Asn Lys Phe Ser Arg Ile Thr
370 375 380

Thr Leu Ile Thr Pro Phe Thr Tyr Lys Lys Leu Tyr Ile Thr Lys Tyr
385 390 395 400

Ser Ser Ser Ser Val Phe Asn Asp Ile Tyr Ser Tyr Lys Gly Asp Asn
405 410 415

Lys Thr His Asp Asp Ala Leu Asp Ala Ile Ser Ala Ala Tyr Leu Met
420 425 430

Leu Ser Leu Gly Tyr Arg Glu Arg Ser Val His Phe Gly Asn Gln Arg
435 440 445

Phe Leu
450

<210> SEQ ID NO 41
<211> LENGTH: 450
<212> TYPE: PRT
<213> ORGANISM: Phage from Borrelia burgdorferi

<400> SEQUENCE: 41

Met Asn Leu Tyr Gln Thr Lys Leu Phe Thr Thr Leu Gln Lys Glu Tyr
1 5 10 15

Lys Asn Lys Tyr Gly Val Asp Ile Ser Gln Phe Val Lys Leu Thr Asn
20 25 30

Ser Ser Ile Asn Phe Asp Lys Phe Glu Glu Glu Gln Leu Thr Leu Lys
35 40 45

Gln Lys Asn Val Ile Lys Ser Ile Lys Lys Asn Asn Glu Lys Lys Ile
50 55 60

Ile Leu Ser Gly Gly Ile Ala Ser Gly Lys Thr Tyr Leu Ala Cys Tyr
65 70 75 80

Leu Phe Leu Lys Ser Leu Ile Glu Asn Lys Lys Leu Tyr Ser Ser Asp
85 90 95

Thr Asn Asn Phe Ile Ile Gly Asn Ser Gln Arg Ser Val Glu Val Asn
100 105 110

Val Leu Gly Gln Phe Glu Lys Leu Cys Lys Leu Leu Lys Ile Pro Tyr
115 120 125

Ile Pro Arg His Thr Asn Asn Ser Tyr Ile Leu Ile Asp Ser Leu Arg
130 135 140

Ile Asn Leu Tyr Gly Gly Asp Lys Ala Ser Asp Phe Glu Arg Phe Arg
145 150 155 160

Gly Ser Asn Ser Ala Leu Ile Phe Val Asn Glu Ala Thr Thr Leu His
165 170 175

Lys Gln Thr Leu Glu Glu Val Leu Lys Arg Leu Arg Cys Gly Gln Glu
180 185 190

Thr Ile Ile Phe Asp Thr Asn Pro Asp His Pro Glu His Tyr Phe Lys
195 200 205

Thr Asp Tyr Ile Asp Asn Ile Ala Thr Phe Lys Thr Tyr Lys Phe Thr
210 215 220

-continued

Thr Tyr Asp Asn Val Leu Leu Ser Lys Gly Phe Val Glu Thr Gln Glu
225 230 235 240

Lys Leu Tyr Lys Asp Ile Pro Ser Tyr Lys Ala Arg Val Leu Leu Gly
245 250 255

Glu Trp Ile Ala Ser Thr Asp Ser Ile Phe Thr Gln Ile Asn Ile Thr
260 265 270

Asp Asp Tyr Val Phe Thr Ser Pro Ile Ala Tyr Leu Asp Pro Ala Phe
275 280 285

Ser Val Gly Gly Asp Asn Thr Ala Leu Cys Val Met Glu Arg Val Asp
290 295 300

Asp Lys Tyr Tyr Ala Phe Val Phe Gln Asp Gln Arg Pro Ala Asn Asp
305 310 315 320

Pro Tyr Ile Met Asn Met Val Lys Thr Val Ile Glu Asn Phe Asn Val
325 330 335

His Thr Leu Tyr Leu Glu Asp Arg Asp Asn Thr Lys Gly Ala Gly Gly
340 345 350

Leu Thr Arg Glu Tyr Ile Leu Leu Arg Ser Asn Ile Ser Gln Tyr Phe
355 360 365

Arg Ile Val Pro Val Lys Pro Lys Ser Asn Lys Phe Ser Arg Ile Thr
370 375 380

Thr Leu Ile Thr Pro Phe Thr Tyr Lys Lys Leu Tyr Ile Thr Lys Tyr
385 390 395 400

Ser Ser Ser Ser Val Phe Asn Asp Ile Tyr Ser Tyr Lys Gly Asp Asn
405 410 415

Lys Thr His Asp Asp Ala Leu Asp Ala Ile Ser Ala Ala Tyr Leu Met
420 425 430

Leu Ser Leu Gly Tyr Arg Glu Arg Ser Val His Phe Gly Asn Gln Arg
435 440 445

Phe Leu
450

<210> SEQ ID NO 42
<211> LENGTH: 450
<212> TYPE: PRT
<213> ORGANISM: Phage from Borrelia burgdorferi

<400> SEQUENCE: 42

Met Asn Leu Tyr Gln Thr Lys Leu Phe Thr Thr Leu Gln Lys Glu Tyr
1 5 10 15

Lys Asn Lys Tyr Gly Val Asp Ile Ser Gln Phe Val Lys Leu Ala Asn
20 25 30

Ser Ser Ile Asn Phe Asp Lys Phe Glu Glu Lys Gln Leu Thr Leu Lys
35 40 45

Gln Lys Asn Val Ile Lys Ser Ile Lys Lys Asn Asn Glu Lys Lys Ile
50 55 60

Ile Leu Ser Gly Gly Ile Ala Ser Gly Lys Thr Tyr Leu Ala Cys Tyr
65 70 75 80

Leu Phe Leu Lys Ser Leu Ile Glu Asn Lys Lys Leu Tyr Ser Ser Asp
85 90 95

Thr Asn Asn Phe Ile Ile Gly Asn Ser Gln Arg Ser Val Glu Val Asn
100 105 110

Val Leu Gly Gln Phe Glu Lys Leu Cys Lys Leu Leu Lys Ile Pro Tyr
115 120 125

Ile Pro Arg His Thr Asn Asn Ser Tyr Ile Leu Ile Asp Ser Leu Arg
130 135 140

Ile Asn Leu Tyr Gly Gly Asp Lys Ala Ser Asp Phe Glu Arg Phe Arg
145 150 155 160

Gly Ser Asn Ser Ala Leu Ile Phe Val Asn Glu Ala Thr Thr Leu His
165 170 175

Lys Gln Thr Leu Glu Glu Val Leu Lys Arg Leu Arg Cys Gly Gln Glu
180 185 190

Thr Ile Ile Phe Asp Thr Asn Pro Asp His Pro Glu His Tyr Phe Lys
195 200 205

Thr Asp Tyr Ile Asp Asn Ile Ala Thr Phe Lys Ile Tyr Asn Phe Thr
210 215 220

Thr Tyr Asp Asn Val Leu Leu Ser Lys Gly Phe Ile Glu Thr Gln Glu
225 230 235 240

Lys Leu Tyr Lys Asp Ile Pro Ser Tyr Lys Ala Arg Val Leu Leu Gly
245 250 255

Glu Trp Ile Ala Ser Thr Asp Ser Ile Phe Thr Gln Ile Asn Ile Thr
260 265 270

Asp Asp Tyr Ile Phe Thr Ser Pro Ile Ala Tyr Leu Asp Pro Ala Phe
275 280 285

Ser Val Gly Gly Asp Asn Thr Ala Leu Cys Val Met Glu Arg Val Asp
290 295 300

Asp Lys Tyr Tyr Ala Phe Val Phe Gln Asp Gln Arg Pro Ala Asn Asp
305 310 315 320

Pro Tyr Ile Met Asn Met Val Lys Thr Val Ile Glu Asn Phe Asn Val
325 330 335

His Thr Leu Tyr Leu Glu Asp Arg Asp Asn Thr Lys Gly Ala Gly Gly
340 345 350

Leu Thr Arg Glu Tyr Ile Leu Leu Arg Asn Asn Ile Ser Gln Tyr Phe
355 360 365

Arg Ile Val Pro Val Lys Pro Lys Ser Asn Lys Phe Ser Arg Ile Thr
370 375 380

Met Leu Ile Thr Pro Phe Thr Tyr Lys Lys Leu Tyr Ile Thr Lys Tyr
385 390 395 400

Ser Ser Ser Ser Val Phe Asn Asp Ile Tyr Ser Tyr Lys Gly Asp Ser
405 410 415

Lys Thr His Asp Asp Ala Leu Asp Ala Ile Ser Ala Ala Tyr Leu Met
420 425 430

Leu Ser Leu Gly Tyr Arg Glu Arg Ser Val His Phe Gly Asn Gln Arg
435 440 445

Phe Leu
450

<210> SEQ ID NO 43
<211> LENGTH: 450
<212> TYPE: PRT
<213> ORGANISM: Phage from Borrelia burgdorferi

<400> SEQUENCE: 43

Met Asn Leu Tyr Gln Thr Lys Leu Phe Thr Ile Leu Gln Lys Glu Tyr
1 5 10 15

Lys Asn Lys Tyr Gly Val Asp Ile Ser Gln Phe Val Lys Leu Thr Asn
20 25 30

Ser Ser Ile Asn Phe Asp Lys Phe Glu Glu Glu Gln Leu Thr Leu Lys
35 40 45

Gln Lys Asn Val Ile Lys Ser Ile Lys Lys Asn Asn Glu Lys Lys Ile

```
    50                  55                  60

Ile Leu Ser Gly Gly Ile Ala Ser Gly Lys Thr Tyr Leu Ala Cys Tyr
65                  70                  75                  80

Leu Phe Ile Lys Ser Leu Ile Glu Asn Lys Lys Leu Tyr Ser Ser Asp
                85                  90                  95

Thr Asn Asn Phe Ile Ile Gly Asn Ser Gln Arg Ser Val Glu Val Asn
            100                 105                 110

Val Leu Gly Gln Phe Glu Lys Leu Cys Lys Leu Leu Lys Ile Pro Tyr
        115                 120                 125

Ile Pro Arg His Thr Asn Asn Ser Tyr Ile Leu Ile Asp Ser Leu Arg
    130                 135                 140

Ile Asn Leu His Gly Gly Asp Lys Ala Ser Asp Phe Glu Arg Phe Arg
145                 150                 155                 160

Gly Ser Asn Ser Ala Leu Ile Phe Val Asn Glu Ala Thr Thr Leu His
                165                 170                 175

Lys Gln Thr Leu Glu Glu Val Leu Lys Arg Leu Arg Cys Gly Gln Glu
            180                 185                 190

Thr Ile Ile Phe Asp Thr Asn Pro Asp His Pro Glu His Tyr Phe Lys
        195                 200                 205

Thr Asp Tyr Ile Asp Asn Ile Ala Thr Phe Lys Thr Tyr Asn Phe Thr
    210                 215                 220

Thr Tyr Asp Asn Val Leu Leu Ser Lys Gly Phe Ile Glu Thr Gln Glu
225                 230                 235                 240

Lys Leu Tyr Lys Asp Ile Pro Ser Tyr Lys Ala Arg Val Leu Leu Gly
                245                 250                 255

Glu Trp Ile Ala Ser Thr Asp Ser Ile Phe Thr Gln Ile Asn Ile Thr
            260                 265                 270

Asn Asp Tyr Val Phe Thr Ser Pro Ile Ala Tyr Leu Asp Pro Ala Phe
        275                 280                 285

Ser Val Gly Gly Asp Asn Thr Ala Leu Cys Val Met Glu Arg Val Asp
    290                 295                 300

Asp Lys Tyr Tyr Ala Phe Val Phe Gln Asp Gln Arg Pro Ala Asn Asp
305                 310                 315                 320

Pro Tyr Ile Met Asn Met Val Lys Thr Val Leu Glu Asn Phe Asn Val
                325                 330                 335

His Thr Phe Tyr Leu Glu Asp Arg Asp Asn Thr Lys Gly Ala Gly Gly
            340                 345                 350

Leu Thr Arg Glu Tyr Ile Leu Leu Arg Asn Asn Met Gly Gln Tyr Phe
        355                 360                 365

Arg Ile Val Pro Val Lys Pro Lys Ser Asn Lys Phe Ser Arg Ile Thr
    370                 375                 380

Ala Leu Ile Thr Pro Phe Ile Tyr Lys Lys Leu Tyr Ile Thr Lys Tyr
385                 390                 395                 400

Ser Ser Ser Ser Val Phe Asn Asp Ile Tyr Ser Tyr Lys Gly Asp Asn
                405                 410                 415

Lys Thr His Asp Asp Ala Leu Asp Ala Ile Ser Ala Ala Tyr Leu Met
            420                 425                 430

Leu Ser Leu Gly Tyr Arg Glu Arg Ser Val His Phe Gly Asn Gln Arg
        435                 440                 445

Phe Leu
    450
```

<210> SEQ ID NO 44

<211> LENGTH: 450
<212> TYPE: PRT
<213> ORGANISM: Phage from Borrelia burgdorferi

<400> SEQUENCE: 44

```
Met Lys Phe Leu Arg Ser Leu Ala Phe Leu Asn Leu Gln Lys Lys Phe
1               5                   10                  15

Lys Asn Lys Phe Asn Ile Asn Ile Leu Asp Tyr Ile Lys Pro Lys Pro
            20                  25                  30

Thr Lys Ile Cys Phe Lys Asp Phe Glu Asn Lys Tyr Leu Thr Ala Lys
        35                  40                  45

Gln Lys Glu Val Leu Phe Asp Ile Glu Ser Asn Asn Tyr Ser Lys Val
    50                  55                  60

Ile Phe Ser Gly Gly Ile Ala Ser Gly Lys Thr Phe Leu Ala Ser Tyr
65                  70                  75                  80

Leu Leu Val Lys Lys Leu Ile Glu Asn Lys Ser Phe Tyr Glu Gln Asp
                85                  90                  95

Thr Asn Asn Phe Ile Ile Gly Asn Ser Ile Gly Leu Leu Met Thr Asn
            100                 105                 110

Thr Val Lys Gln Ile Glu Lys Ile Cys Ser Leu Leu Gly Ile Asp Tyr
        115                 120                 125

Glu Lys Lys Lys Ser Gly Gln Ser Phe Cys Lys Ile Ala Gly Leu Lys
    130                 135                 140

Leu Asn Ile Tyr Gly Gly Lys Asn Arg Asp Ala Phe Ser Lys Ile Arg
145                 150                 155                 160

Gly Gly Asn Ser Ala Ile Ile Tyr Val Asn Glu Ala Thr Val Ile His
                165                 170                 175

Arg Glu Thr Leu Leu Glu Val Ile Lys Arg Leu Arg Lys Gly Lys Glu
            180                 185                 190

Ile Ile Ile Phe Asp Thr Asn Pro Glu Ser Pro Ala His Tyr Phe Lys
        195                 200                 205

Thr Asp Tyr Ile Glu Asn Thr Asp Val Phe Lys Thr Tyr Asn Phe Thr
    210                 215                 220

Thr Tyr Asp Asn Pro Leu Asn Ser Ala Asp Phe Ile Gln Thr Gln Glu
225                 230                 235                 240

Lys Leu Tyr Arg Arg Phe Pro Ala Tyr Arg Ala Arg Val Leu Tyr Gly
                245                 250                 255

Glu Trp Ile Leu Asn Glu Ser Thr Leu Phe Asn Glu Met Ile Phe Asn
            260                 265                 270

Gln Asp Tyr Glu Phe Lys Ser Pro Ile Met Tyr Ile Asp Pro Ala Phe
        275                 280                 285

Ser Val Gly Gly Asp Asn Thr Ala Ile Cys Val Leu Glu Arg Thr Phe
    290                 295                 300

Glu Lys Phe Tyr Ala Tyr Ile Tyr Gln Asp Gln Lys Pro Val Ser Asp
305                 310                 315                 320

Ser Leu Met Leu Ala Ser Ile Gln Val Leu Ile Glu Asn Phe Asn Val
                325                 330                 335

Asn Thr Val Tyr Ile Glu Glu Arg Asp Ser Thr Lys Gly Asp Gly Ile
            340                 345                 350

Leu Thr Lys Thr Ile Leu Phe Leu Arg Asn Lys Ser Ser His Tyr Phe
        355                 360                 365

Lys Val Ala Pro Ile Lys Pro Leu Ser Asn Lys Phe Lys Arg Ile Cys
    370                 375                 380

Ala Leu Ile Pro Leu Phe Glu Ser Arg Lys Ile Glu Phe Leu Lys Ile
```

-continued

```
385                 390                 395                 400

Ile Ser Lys Asn Val Ile Ser Asp Ile Tyr Ser Tyr Lys Gly Asp Gly
                405                 410                 415

Lys Thr Lys Asp Asp Ala Leu Asp Ser Leu Ala Asn Ala Tyr Leu Leu
            420                 425                 430

Leu Thr Leu Asn Tyr Lys Glu Lys Leu Phe His Phe Gly Arg Phe Lys
        435                 440                 445

Tyr Leu
    450


<210> SEQ ID NO 45
<211> LENGTH: 396
<212> TYPE: PRT
<213> ORGANISM: Phage from Borrelia burgdorferi

<400> SEQUENCE: 45

Met Arg Leu Arg Arg Leu Pro Val Tyr Val Asp Ala Tyr Lys Glu Lys
1               5                   10                  15

Pro Asn Ala Glu Ile Phe Ile Tyr Tyr Ser Ser Arg Gly Thr Gly Lys
            20                  25                  30

Thr Tyr Asp Ile Ala Thr Val Asn Leu Glu Arg Lys Phe Ser Ala Asp
        35                  40                  45

Gly Gly Asp Thr Leu Ala Ile Arg Lys Lys Lys Asn Lys Thr Thr Gln
    50                  55                  60

Ser Ile His Lys Glu Ile Leu Glu Leu Leu Ser Ile Tyr Asn Leu Arg
65                  70                  75                  80

Lys Phe Phe Asn Ile Ser Lys Ala Lys Ile Glu Ser Lys Ser Leu Ile
                85                  90                  95

Phe Gly Lys Lys Arg Ala Phe Val Phe Glu Gly Gly His Asp Thr Arg
            100                 105                 110

Asp Leu Lys Ser Tyr Ala His Phe Lys Asp Leu Trp Leu Glu Glu Ala
        115                 120                 125

Asn Gln Phe Ser Ala Asp Asp Ile Glu Met Leu Val Pro Thr Met Arg
    130                 135                 140

Glu Gln Gly Gly Arg Ile Tyr Met Ser Ser Asn Pro Val Pro Lys Ser
145                 150                 155                 160

His Trp Leu Tyr Lys Arg Tyr Leu Ser Asn Gln Asp Asn Pro Ala Val
                165                 170                 175

Cys Ile Ile Lys Ser Thr Tyr Arg Asp Asn Pro Phe Leu Asn Gly Gly
            180                 185                 190

Asp Val Gln Ala Trp Leu Glu Lys Gln Arg Leu Ala Tyr His Gly Asn
        195                 200                 205

Asp Ile Gly Phe Arg Ile Glu Val Leu Gly Glu Glu Phe Asp Phe Gly
    210                 215                 220

Thr Ala Arg Leu Ile Lys Lys Phe Asn Val Cys Gly Pro Glu Ile Leu
225                 230                 235                 240

Ser Arg Ala Asn Gly Ser Tyr Tyr Thr Gly Ile His Val Lys Gly Asn
                245                 250                 255

Arg Ile Cys Phe Leu Glu Ile Leu Val Gly Arg Ile Ser Tyr Leu Pro
            260                 265                 270

Val Val Ile Ile Thr Asn Ala Cys Ser Lys Val Leu Leu Ser Lys Thr
        275                 280                 285

Asp Tyr Gln Ser Glu Ile Asn Lys Phe Lys Gly Val Phe Val Leu Pro
    290                 295                 300
```

-continued

Thr Ala Arg Glu Glu Leu Lys Tyr Val Phe Ser Arg Phe Gly Arg Gly
305 310 315 320

Thr Leu Leu Ala Lys Lys Arg Asn Leu Tyr Ser Leu Ser Asp Tyr Leu
325 330 335

Ile Pro Ser Asn Leu Asn Val Val Asn Lys Pro Glu Thr Thr Asp Val
340 345 350

Ile Ser Glu Phe Asn Glu Thr Glu Tyr Tyr Tyr Asp Glu Ser Ser Ala
355 360 365

Glu Asp Ser Glu Val Thr Asn Phe Val Met Gln Lys Asp Leu Val Tyr
370 375 380

Ile Pro Ala Phe Leu Asn Ala Ile Ser Val Phe Ser
385 390 395

<210> SEQ ID NO 46
<211> LENGTH: 1224
<212> TYPE: PRT
<213> ORGANISM: Phage from Borrelia burgdorferi

<400> SEQUENCE: 46

Gly Thr Gly Thr Gly Thr Gly Ala Thr Thr Thr Ala Ala Gly Ala Ala
1 5 10 15

Ala Ala Ala Cys Ala Ala Ala Ala Cys Thr Ala Ala Thr Ala Gly Ala
20 25 30

Thr Ala Ala Ala Ala Thr Ala Ala Gly Thr Thr Cys Ala Cys Thr Ala
35 40 45

Gly Ala Ala Cys Thr Ala Thr Ala Cys Ala Ala Ala Thr Ala Cys Thr
50 55 60

Cys Ala Ala Thr Ala Thr Thr Thr Thr Thr Thr Ala Gly Ala Ala Ala
65 70 75 80

Thr Thr Ala Cys Ala Thr Thr Gly Ala Ala Ala Ala Thr Gly Thr Ala
85 90 95

Gly Cys Ala Gly Ala Ala Gly Ala Thr Thr Gly Thr Cys Thr Cys Ala
100 105 110

Ala Gly Ala Ala Cys Gly Gly Ala Cys Thr Thr Ala Thr Thr Cys Thr
115 120 125

Thr Gly Ala Gly Ala Gly Thr Gly Cys Thr Gly Cys Cys Cys Ala Cys
130 135 140

Ala Ala Thr Gly Thr Thr Ala Gly Thr Gly Ala Gly Gly Thr Thr Gly
145 150 155 160

Ala Ala Cys Thr Thr Gly Cys Thr Ala Gly Gly Thr Thr Ala Ala Ala
165 170 175

Gly Gly Thr Ala Cys Ala Gly Cys Thr Thr Ala Ala Gly Ala Ala Thr
180 185 190

Gly Cys Thr Cys Thr Gly Cys Thr Thr Ala Ala Thr Thr Gly Thr Ala
195 200 205

Thr Thr Ala Thr Ala Ala Gly Cys Thr Ala Cys Cys Gly Thr Thr Thr
210 215 220

Thr Cys Ala Thr Gly Gly Ala Thr Thr Gly Gly Cys Thr Ala Thr
225 230 235 240

Gly Thr Thr Thr Thr Ala Gly Thr Ala Ala Ala Ala Ala Cys Cys Ala
245 250 255

Ala Ala Gly Ala Thr Ala Cys Cys Cys Thr Ala Ala Thr Ala Gly Ala
260 265 270

Thr Cys Thr Cys Gly Ala Ala Cys Ala Ala Cys Cys Cys Gly Thr Thr
275 280 285

Ala Ala Thr Ala Thr Ala Gly Ala Ala Thr Thr Ala Cys Cys Thr Ala
290 295 300

Thr Thr Gly Gly Thr Thr Thr Thr Gly Ala Ala Thr Ala Cys Cys Thr
305 310 315 320

Thr Gly Ala Thr Thr Ala Thr Gly Ala Ala Thr Ala Thr Gly Thr Ala
325 330 335

Ala Gly Ala Gly Ala Thr Thr Thr Gly Gly Gly Ala Gly Thr Thr Gly
340 345 350

Ala Thr Thr Thr Thr Gly Ala Thr Cys Ala Thr Ala Thr Ala Ala Cys
355 360 365

Cys Thr Ala Thr Ala Ala Ala Gly Thr Ala Ala Ala Ala Thr Cys Cys
370 375 380

Ala Ala Cys Ala Ala Thr Ala Ala Gly Ala Ala Cys Ala Ala Thr Thr
385 390 395 400

Cys Thr Thr Thr Ala Gly Ala Cys Gly Cys Ala Gly Thr Thr Ala Ala
405 410 415

Ala Ala Thr Ala Cys Ala Thr Ala Ala Ala Ala Gly Thr Cys Gly Ala
420 425 430

Cys Thr Thr Ala Thr Cys Ala Thr Ala Thr Ala Thr Gly Ala Ala Ala
435 440 445

Ala Cys Thr Thr Thr Gly Ala Thr Thr Ala Thr Ala Thr Cys Thr Thr
450 455 460

Ala Ala Ala Ala Ala Gly Ala Thr Ala Thr Gly Thr Thr Cys Cys Gly
465 470 475 480

Thr Gly Thr Thr Ala Thr Ala Cys Cys Gly Ala Ala Ala Gly Cys Thr
485 490 495

Thr Thr Thr Thr Ala Cys Thr Ala Gly Ala Thr Ala Thr Thr Thr Ala
500 505 510

Thr Thr Thr Ala Thr Thr Thr Gly Ala Ala Ala Ala Gly Ala Thr Ala
515 520 525

Thr Ala Cys Gly Thr Ala Gly Ala Ala Ala Thr Ala Gly Ala Ala Ala
530 535 540

Gly Ala Cys Gly Thr Ala Thr Thr Gly Ala Ala Ala Ala Cys Cys Ala
545 550 555 560

Cys Ala Ala Thr Thr Thr Cys Thr Thr Gly Thr Thr Thr Thr Ala Thr
565 570 575

Ala Ala Ala Gly Ala Thr Gly Ala Ala Thr Cys Thr Thr Thr Ala Gly
580 585 590

Thr Ala Cys Ala Ala Cys Thr Ala Cys Ala Ala Gly Ala Cys Gly Cys
595 600 605

Ala Cys Thr Cys Thr Cys Thr Ala Gly Thr Gly Cys Ala Ala Cys Ala
610 615 620

Ala Cys Thr Thr Cys Thr Thr Thr Ala Ala Gly Thr Gly Cys Ala Cys
625 630 635 640

Thr Thr Ala Cys Thr Cys Ala Gly Ala Gly Cys Ala Ala Thr Ala Ala
645 650 655

Thr Gly Ala Thr Ala Gly Gly Gly Gly Ala Ala Gly Thr Gly Gly Cys
660 665 670

Ala Thr Thr Thr Thr Ala Thr Cys Thr Thr Cys Thr Thr Thr Thr Thr
675 680 685

Thr Gly Ala Gly Ala Ala Ala Ala Cys Ala Ala Ala Ala Thr Thr Cys
690 695 700

-continued

```
Ala Ala Ala Cys Ala Ala Thr Cys Ala Thr Ala Gly Thr Ala Ala Ala
705                 710                 715                 720

Gly Ala Thr Ala Thr Thr Thr Cys Thr Ala Ala Thr Thr Thr Ala Ala
                725                 730                 735

Gly Ala Ala Ala Cys Cys Thr Thr Ala Ala Thr Gly Ala Cys Thr Cys
            740                 745                 750

Ala Thr Thr Ala Thr Cys Ala Cys Ala Gly Gly Ala Gly Cys Thr Thr
        755                 760                 765

Gly Cys Thr Ala Gly Gly Cys Thr Ala Ala Ala Ala Ala Gly Cys Ala
    770                 775                 780

Ala Thr Cys Thr Ala Ala Ala Thr Ala Ala Thr Gly Ala Gly Gly Gly
785                 790                 795                 800

Ala Ala Thr Gly Thr Thr Thr Thr Ala Thr Ala Cys Gly Gly Cys Cys
                805                 810                 815

Ala Cys Cys Cys Cys Thr Ala Gly Thr Gly Cys Thr Ala Gly Thr Thr
            820                 825                 830

Thr Ala Gly Ala Gly Gly Thr Thr Ala Thr Thr Ala Ala Ala Thr Ala
        835                 840                 845

Cys Gly Ala Thr Cys Thr Thr Ala Gly Cys Thr Ala Cys Thr Thr Ala
    850                 855                 860

Ala Ala Gly Gly Ala Gly Gly Cys Thr Thr Thr Ala Gly Cys Ala Thr
865                 870                 875                 880

Thr Ala Ala Thr Thr Ala Ala Gly Gly Cys Ala Ala Ala Ala Ala Thr
                885                 890                 895

Thr Gly Gly Thr Gly Cys Ala Gly Ala Thr Ala Cys Thr Ala Ala Ala
            900                 905                 910

Gly Ala Gly Cys Cys Cys Thr Thr Ala Ala Cys Cys Ala Gly Ala Ala
        915                 920                 925

Gly Thr Thr Thr Thr Ala Ala Thr Gly Ala Gly Cys Ala Gly Gly Cys
    930                 935                 940

Thr Ala Ala Ala Gly Gly Ala Cys Thr Ala Gly Gly Ala Ala Ala Thr
945                 950                 955                 960

Gly Ala Thr Gly Gly Thr Ala Ala Ala Gly Gly Thr Gly Ala Thr Ala
                965                 970                 975

Gly Gly Ala Gly Thr Ala Ala Thr Thr Ala Thr Thr Ala Cys Gly Ala
            980                 985                 990

Thr Thr Thr Thr Cys Thr Cys Ala  Ala Ala Gly Gly Thr  Gly Thr Ala
        995                 1000                1005

Cys Ala  Ala Gly Ala Ala Cys  Ala Ala Gly Thr Thr  Gly Ala Gly
    1010                 1015                 1020

Ala Ala  Cys Thr Cys Thr Thr  Gly Thr Ala Ala Thr  Thr Thr Ala
    1025                 1030                 1035

Ala Ala  Ala Cys Thr Thr Ala  Cys Ala Ala Ala Gly  Thr Ala Thr
    1040                 1045                 1050

Thr Thr  Thr Gly Gly Gly Cys  Thr Thr Gly Ala Thr  Ala Thr Gly
    1055                 1060                 1065

Ala Ala  Gly Thr Thr Thr Ala  Ala Thr Thr Cys Thr  Cys Thr Gly
    1070                 1075                 1080

Ala Thr  Thr Ala Thr Gly Thr  Thr Ala Ala Gly Thr  Gly Ala Ala
    1085                 1090                 1095

Gly Ala  Ala Cys Ala Ala Ala  Ala Ala Gly Thr Gly  Gly Ala Ala
    1100                 1105                 1110

Ala Gly  Ala Gly Ala Thr Ala  Thr Ala Ala Ala Gly  Cys Thr Ala
```

-continued

```
    1115                1120                1125

Ala Thr  Thr Gly Ala Gly Cys  Thr Thr Thr Ala Cys  Ala Gly Thr
    1130                1135                1140

Ala Ala  Ala Thr Ala Thr Ala  Ala Cys Cys Ala Gly  Cys Thr Thr
    1145                1150                1155

Ala Thr  Ala Cys Ala Ala Ala  Gly Thr Ala Gly Cys  Thr Cys Ala
    1160                1165                1170

Thr Thr  Thr Ala Ala Thr Ala  Ala Thr Gly Ala Gly  Gly Ala Gly
    1175                1180                1185

Cys Thr  Ala Gly Cys Gly Ala  Thr Gly Thr Thr Ala  Ala Ala Ala
    1190                1195                1200

Gly Ala  Gly Ala Ala Ala Thr  Thr Ala Thr Thr Cys  Thr Cys Ala
    1205                1210                1215

Thr Thr  Thr Thr Gly Ala
    1220


<210> SEQ ID NO 47
<211> LENGTH: 1224
<212> TYPE: PRT
<213> ORGANISM: Phage from Borrelia burgdorferi

<400> SEQUENCE: 47

Gly Thr Gly Thr Gly Thr Gly Ala Thr Thr Thr Ala Ala Gly Ala Ala
1               5                   10                  15

Ala Ala Ala Cys Ala Ala Ala Ala Cys Thr Ala Ala Thr Ala Gly Ala
            20                  25                  30

Thr Ala Ala Ala Ala Thr Ala Ala Gly Thr Thr Cys Ala Cys Thr Ala
        35                  40                  45

Gly Ala Ala Cys Thr Ala Thr Ala Cys Ala Ala Ala Thr Ala Cys Thr
    50                  55                  60

Cys Ala Ala Thr Ala Thr Thr Thr Thr Thr Thr Ala Gly Ala Ala Ala
65                  70                  75                  80

Thr Thr Ala Cys Ala Thr Thr Gly Ala Ala Ala Ala Thr Gly Thr Ala
                85                  90                  95

Gly Cys Ala Gly Ala Ala Gly Ala Thr Thr Gly Thr Cys Thr Cys Ala
            100                 105                 110

Ala Gly Ala Ala Cys Gly Gly Ala Cys Thr Thr Ala Thr Thr Cys Thr
        115                 120                 125

Thr Gly Ala Gly Ala Gly Thr Gly Cys Thr Gly Cys Cys Cys Ala Cys
    130                 135                 140

Ala Ala Thr Gly Thr Thr Ala Gly Thr Gly Ala Gly Gly Thr Thr Gly
145                 150                 155                 160

Ala Ala Cys Thr Thr Gly Cys Thr Ala Gly Gly Thr Thr Ala Ala Ala
                165                 170                 175

Gly Gly Thr Ala Cys Ala Gly Cys Thr Thr Ala Ala Gly Ala Ala Thr
            180                 185                 190

Gly Cys Thr Cys Thr Gly Cys Thr Thr Ala Ala Thr Thr Gly Thr Ala
        195                 200                 205

Thr Thr Ala Thr Ala Ala Gly Cys Thr Ala Cys Cys Gly Thr Thr Thr
    210                 215                 220

Thr Cys Ala Thr Gly Gly Gly Ala Thr Thr Gly Gly Cys Thr Ala Thr
225                 230                 235                 240

Gly Thr Thr Thr Thr Ala Gly Thr Ala Ala Ala Ala Ala Cys Cys Ala
                245                 250                 255
```

-continued

```
Ala Ala Gly Ala Thr Ala Cys Cys Cys Thr Ala Ala Thr Ala Gly Ala
            260                 265                 270

Thr Cys Thr Cys Gly Ala Ala Cys Ala Ala Cys Cys Cys Gly Thr Thr
        275                 280                 285

Ala Ala Thr Ala Thr Ala Gly Ala Ala Thr Thr Ala Cys Cys Thr Ala
    290                 295                 300

Thr Thr Gly Gly Thr Thr Thr Thr Gly Ala Ala Thr Ala Cys Cys Thr
305                 310                 315                 320

Thr Gly Ala Thr Thr Ala Thr Gly Ala Ala Thr Ala Thr Gly Thr Ala
                325                 330                 335

Ala Gly Ala Gly Ala Thr Thr Thr Gly Gly Gly Ala Gly Thr Thr Gly
            340                 345                 350

Ala Thr Thr Thr Thr Gly Ala Thr Cys Ala Thr Ala Thr Ala Ala Cys
        355                 360                 365

Cys Thr Ala Thr Ala Ala Ala Gly Thr Ala Ala Ala Ala Thr Cys Cys
    370                 375                 380

Ala Ala Cys Ala Ala Thr Ala Ala Gly Ala Ala Cys Ala Ala Thr Thr
385                 390                 395                 400

Cys Thr Thr Thr Ala Gly Ala Thr Gly Cys Ala Gly Thr Thr Ala Ala
                405                 410                 415

Ala Ala Thr Ala Cys Ala Thr Ala Ala Ala Ala Gly Thr Cys Gly Ala
            420                 425                 430

Cys Thr Thr Ala Thr Cys Ala Thr Ala Thr Ala Thr Gly Ala Ala Ala
        435                 440                 445

Ala Cys Thr Thr Thr Gly Ala Thr Thr Ala Thr Ala Thr Cys Thr Thr
    450                 455                 460

Ala Ala Ala Ala Ala Gly Ala Thr Ala Thr Gly Thr Thr Cys Cys Gly
465                 470                 475                 480

Thr Gly Cys Thr Ala Thr Ala Cys Cys Gly Ala Ala Ala Gly Cys Thr
                485                 490                 495

Thr Thr Thr Thr Ala Cys Thr Ala Gly Ala Thr Ala Thr Thr Thr Ala
            500                 505                 510

Thr Thr Thr Ala Thr Thr Thr Gly Ala Ala Ala Ala Gly Ala Thr Ala
        515                 520                 525

Thr Ala Cys Gly Thr Ala Gly Ala Ala Ala Thr Ala Gly Ala Ala Ala
    530                 535                 540

Gly Ala Cys Gly Thr Ala Thr Thr Gly Ala Ala Ala Ala Cys Cys Ala
545                 550                 555                 560

Cys Ala Ala Thr Thr Thr Thr Thr Thr Gly Thr Thr Thr Thr Ala Cys
                565                 570                 575

Ala Ala Ala Gly Ala Thr Gly Ala Ala Thr Cys Thr Thr Thr Ala Gly
            580                 585                 590

Thr Ala Cys Ala Ala Cys Thr Ala Cys Ala Ala Gly Ala Cys Gly Cys
        595                 600                 605

Ala Cys Thr Thr Thr Cys Thr Ala Gly Thr Gly Cys Ala Ala Cys Ala
    610                 615                 620

Ala Cys Thr Thr Cys Thr Thr Thr Ala Ala Gly Thr Gly Cys Ala Cys
625                 630                 635                 640

Thr Thr Ala Cys Thr Cys Ala Gly Ala Gly Cys Ala Ala Thr Ala Ala
                645                 650                 655

Thr Gly Ala Thr Ala Gly Gly Gly Gly Ala Ala Gly Thr Gly Gly Cys
            660                 665                 670

Ala Thr Thr Thr Thr Ala Thr Cys Thr Thr Cys Thr Thr Thr Thr Thr
```

```
        675                 680                 685

Thr Gly Ala Gly Ala Ala Ala Ala Cys Ala Ala Ala Ala Thr Thr Cys
    690                 695                 700

Ala Ala Ala Cys Ala Ala Thr Cys Ala Thr Ala Gly Thr Ala Ala Ala
705                 710                 715                 720

Gly Ala Thr Ala Thr Thr Thr Cys Thr Ala Ala Thr Thr Thr Ala Ala
                725                 730                 735

Gly Ala Ala Ala Cys Cys Thr Thr Ala Ala Thr Gly Ala Cys Thr Cys
            740                 745                 750

Ala Thr Thr Gly Thr Cys Ala Cys Ala Gly Gly Ala Gly Cys Thr Thr
        755                 760                 765

Gly Cys Cys Ala Gly Gly Cys Thr Ala Ala Ala Ala Ala Gly Cys Ala
    770                 775                 780

Ala Thr Cys Thr Ala Ala Ala Thr Ala Ala Thr Gly Ala Gly Gly Gly
785                 790                 795                 800

Ala Ala Thr Gly Thr Thr Thr Thr Ala Thr Ala Cys Ala Gly Cys Thr
                805                 810                 815

Ala Cys Thr Cys Cys Thr Ala Gly Thr Gly Cys Thr Ala Gly Thr Thr
            820                 825                 830

Thr Ala Gly Ala Gly Gly Thr Thr Ala Thr Thr Ala Ala Ala Thr Ala
        835                 840                 845

Cys Gly Ala Thr Cys Thr Thr Ala Gly Thr Thr Ala Cys Thr Thr Ala
    850                 855                 860

Ala Ala Gly Gly Ala Gly Gly Cys Thr Thr Thr Ala Gly Cys Ala Thr
865                 870                 875                 880

Thr Ala Ala Thr Thr Ala Ala Gly Gly Cys Ala Ala Ala Ala Ala Thr
                885                 890                 895

Thr Gly Gly Thr Gly Cys Ala Gly Ala Thr Ala Cys Thr Ala Ala Ala
            900                 905                 910

Gly Ala Gly Cys Cys Cys Thr Thr Ala Ala Cys Cys Ala Gly Ala Ala
        915                 920                 925

Gly Thr Thr Thr Thr Ala Ala Thr Gly Ala Ala Cys Ala Gly Gly Cys
    930                 935                 940

Thr Ala Ala Ala Gly Gly Ala Cys Thr Gly Gly Gly Ala Ala Ala Thr
945                 950                 955                 960

Gly Ala Thr Gly Gly Thr Ala Ala Ala Gly Gly Thr Gly Ala Thr Ala
                965                 970                 975

Gly Gly Ala Gly Thr Ala Ala Thr Thr Ala Thr Thr Ala Cys Gly Ala
            980                 985                 990

Thr Thr Thr Thr Cys Thr Cys Ala  Ala Ala Gly Gly Thr  Gly Thr Ala
        995                 1000                1005

Cys Ala  Ala Gly Ala Ala Cys  Ala Ala Gly Thr Thr  Gly Ala Gly
    1010                1015                1020

Ala Ala  Cys Thr Cys Thr Thr  Gly Thr Ala Ala Thr  Thr Thr Ala
    1025                1030                1035

Ala Ala  Ala Cys Thr Thr Ala  Cys Ala Ala Ala Gly  Thr Ala Thr
    1040                1045                1050

Thr Thr  Thr Gly Gly Ala Cys  Thr Thr Gly Ala Thr  Ala Thr Gly
    1055                1060                1065

Ala Ala  Gly Thr Thr Thr Ala  Ala Thr Thr Cys Gly  Cys Thr Gly
    1070                1075                1080

Ala Thr  Thr Ala Thr Gly Thr  Thr Ala Ala Gly Thr  Gly Ala Ala
    1085                1090                1095
```

Gly Ala Ala Cys Ala Ala Ala Ala Ala Gly Thr Ala Gly Ala Ala
1100 1105 1110

Ala Gly Ala Gly Ala Thr Ala Thr Ala Ala Ala Gly Cys Thr Ala
1115 1120 1125

Ala Thr Thr Gly Ala Gly Cys Thr Thr Thr Ala Cys Ala Gly Thr
1130 1135 1140

Ala Ala Ala Thr Ala Thr Ala Ala Cys Cys Ala Gly Cys Thr Thr
1145 1150 1155

Ala Thr Ala Cys Ala Ala Ala Gly Thr Ala Gly Cys Thr Cys Ala
1160 1165 1170

Thr Thr Thr Ala Ala Thr Ala Ala Thr Gly Ala Gly Gly Ala Gly
1175 1180 1185

Cys Thr Ala Gly Cys Gly Ala Thr Gly Thr Thr Ala Ala Ala Ala
1190 1195 1200

Gly Ala Gly Ala Ala Ala Thr Thr Ala Thr Thr Cys Thr Cys Ala
1205 1210 1215

Thr Thr Thr Thr Gly Ala
1220

<210> SEQ ID NO 48
<211> LENGTH: 1224
<212> TYPE: PRT
<213> ORGANISM: Phage from Borrelia burgdorferi

<400> SEQUENCE: 48

Gly Thr Gly Thr Gly Thr Gly Ala Thr Thr Thr Ala Ala Gly Ala Ala
1 5 10 15

Ala Ala Ala Cys Ala Ala Ala Ala Cys Thr Ala Ala Thr Ala Gly Ala
20 25 30

Thr Ala Ala Ala Ala Thr Ala Ala Gly Thr Thr Cys Ala Cys Thr Ala
35 40 45

Gly Ala Ala Cys Thr Ala Thr Ala Cys Ala Ala Ala Thr Ala Cys Thr
50 55 60

Cys Ala Ala Thr Ala Thr Thr Thr Thr Thr Thr Ala Gly Ala Ala Ala
65 70 75 80

Thr Thr Ala Cys Ala Thr Thr Gly Ala Ala Ala Ala Thr Gly Thr Ala
85 90 95

Gly Cys Ala Gly Ala Ala Gly Ala Thr Thr Gly Thr Cys Thr Cys Ala
100 105 110

Ala Gly Ala Ala Cys Gly Gly Ala Cys Thr Thr Ala Thr Thr Cys Thr
115 120 125

Thr Gly Ala Gly Ala Gly Thr Gly Cys Thr Gly Cys Thr Cys Ala Cys
130 135 140

Ala Ala Thr Gly Thr Thr Ala Gly Thr Gly Ala Gly Gly Thr Thr Gly
145 150 155 160

Ala Ala Cys Thr Thr Gly Cys Thr Ala Gly Gly Thr Thr Ala Ala Ala
165 170 175

Gly Gly Thr Ala Cys Ala Gly Cys Thr Thr Ala Ala Gly Ala Ala Thr
180 185 190

Gly Cys Thr Cys Thr Gly Cys Thr Thr Ala Ala Thr Thr Gly Thr Ala
195 200 205

Thr Thr Ala Thr Ala Ala Gly Cys Thr Ala Cys Cys Gly Thr Thr Thr
210 215 220

Thr Cys Ala Thr Gly Gly Gly Ala Thr Thr Gly Gly Cys Thr Ala Thr

-continued

```
225                 230                 235                 240

Gly Thr Thr Thr Thr Ala Gly Thr Ala Ala Ala Ala Ala Cys Cys Ala
                245                 250                 255

Ala Ala Gly Ala Thr Ala Cys Cys Cys Thr Ala Ala Thr Ala Gly Ala
            260                 265                 270

Thr Cys Thr Cys Gly Ala Ala Cys Ala Ala Cys Cys Cys Gly Thr Thr
        275                 280                 285

Ala Ala Thr Ala Thr Ala Gly Ala Ala Thr Thr Ala Cys Cys Thr Ala
    290                 295                 300

Thr Thr Gly Gly Thr Thr Thr Thr Gly Ala Ala Thr Ala Cys Cys Thr
305                 310                 315                 320

Thr Gly Ala Thr Thr Ala Thr Gly Ala Ala Thr Ala Thr Gly Thr Ala
                325                 330                 335

Ala Gly Ala Gly Ala Thr Thr Thr Gly Gly Gly Ala Gly Thr Thr Gly
            340                 345                 350

Ala Thr Thr Thr Thr Gly Ala Thr Cys Ala Thr Ala Thr Ala Ala Cys
        355                 360                 365

Cys Thr Ala Thr Ala Ala Ala Gly Thr Ala Ala Ala Ala Thr Cys Cys
    370                 375                 380

Ala Ala Cys Ala Ala Thr Ala Ala Gly Ala Ala Cys Ala Ala Thr Thr
385                 390                 395                 400

Cys Thr Thr Thr Ala Gly Ala Cys Gly Cys Ala Gly Thr Thr Ala Ala
                405                 410                 415

Ala Ala Thr Ala Cys Ala Thr Ala Ala Ala Ala Gly Thr Cys Gly Ala
            420                 425                 430

Cys Thr Thr Ala Thr Cys Ala Thr Ala Thr Ala Thr Gly Ala Ala Ala
        435                 440                 445

Ala Cys Thr Thr Thr Gly Ala Thr Thr Ala Thr Ala Thr Cys Thr Thr
    450                 455                 460

Ala Ala Ala Ala Ala Gly Ala Thr Ala Thr Gly Thr Thr Cys Cys Gly
465                 470                 475                 480

Thr Gly Thr Thr Ala Thr Ala Cys Cys Gly Ala Ala Ala Gly Cys Thr
                485                 490                 495

Thr Thr Thr Thr Ala Cys Thr Ala Gly Ala Thr Ala Thr Thr Thr Ala
            500                 505                 510

Thr Thr Thr Ala Thr Thr Thr Gly Ala Ala Ala Ala Gly Ala Thr Ala
        515                 520                 525

Thr Ala Cys Gly Thr Ala Gly Ala Ala Ala Thr Ala Gly Ala Ala Ala
    530                 535                 540

Gly Ala Cys Gly Thr Ala Thr Thr Gly Ala Ala Ala Ala Cys Cys Ala
545                 550                 555                 560

Cys Ala Ala Thr Thr Thr Thr Thr Thr Gly Thr Thr Thr Thr Ala Cys
                565                 570                 575

Ala Ala Ala Gly Ala Thr Gly Ala Ala Thr Cys Thr Thr Thr Ala Gly
            580                 585                 590

Thr Ala Cys Ala Ala Cys Thr Ala Cys Ala Ala Gly Ala Cys Gly Cys
        595                 600                 605

Ala Cys Thr Thr Thr Cys Thr Ala Gly Thr Gly Cys Ala Ala Cys Ala
    610                 615                 620

Ala Cys Thr Thr Cys Thr Thr Thr Ala Ala Gly Thr Gly Cys Ala Cys
625                 630                 635                 640

Thr Thr Ala Cys Thr Cys Ala Gly Ala Gly Cys Ala Ala Thr Ala Ala
                645                 650                 655
```

```
Thr Gly Ala Thr Ala Gly Gly Gly Gly Ala Ala Gly Thr Gly Gly Cys
            660                 665                 670

Ala Thr Thr Thr Thr Ala Thr Cys Thr Thr Cys Thr Thr Thr Thr Thr
        675                 680                 685

Thr Gly Ala Gly Ala Ala Ala Ala Cys Ala Ala Ala Ala Thr Thr Cys
    690                 695                 700

Ala Ala Ala Cys Ala Ala Thr Cys Ala Thr Ala Gly Thr Ala Ala Ala
705                 710                 715                 720

Gly Ala Thr Ala Thr Thr Thr Cys Thr Ala Ala Thr Thr Thr Ala Ala
                725                 730                 735

Gly Ala Ala Ala Cys Cys Thr Thr Ala Ala Thr Gly Ala Cys Thr Cys
            740                 745                 750

Ala Thr Thr Ala Thr Cys Ala Cys Ala Gly Gly Ala Gly Cys Thr Thr
        755                 760                 765

Gly Cys Thr Ala Gly Gly Cys Thr Ala Ala Ala Ala Ala Gly Cys Ala
    770                 775                 780

Ala Thr Cys Thr Ala Ala Ala Thr Ala Ala Thr Gly Ala Gly Gly Gly
785                 790                 795                 800

Ala Ala Thr Gly Thr Thr Thr Thr Ala Thr Ala Cys Gly Gly Cys Cys
                805                 810                 815

Ala Cys Cys Cys Cys Thr Ala Gly Thr Gly Cys Thr Ala Gly Thr Thr
            820                 825                 830

Thr Ala Gly Ala Gly Gly Thr Thr Ala Thr Thr Ala Ala Ala Thr Ala
        835                 840                 845

Cys Gly Ala Thr Cys Thr Thr Ala Gly Cys Thr Ala Cys Thr Thr Ala
    850                 855                 860

Ala Ala Gly Gly Ala Gly Gly Cys Thr Thr Thr Ala Gly Cys Ala Thr
865                 870                 875                 880

Thr Ala Ala Thr Thr Ala Ala Gly Gly Cys Ala Ala Ala Ala Ala Thr
                885                 890                 895

Thr Gly Gly Thr Gly Cys Ala Gly Ala Thr Ala Cys Thr Ala Ala Ala
            900                 905                 910

Gly Ala Gly Cys Cys Cys Thr Thr Ala Ala Cys Cys Ala Gly Ala Ala
        915                 920                 925

Gly Thr Thr Thr Thr Ala Ala Thr Gly Ala Gly Cys Ala Gly Gly Cys
    930                 935                 940

Thr Ala Ala Ala Gly Gly Gly Cys Thr Ala Gly Gly Ala Ala Ala Thr
945                 950                 955                 960

Gly Ala Thr Gly Gly Thr Ala Ala Ala Gly Gly Thr Gly Ala Thr Ala
                965                 970                 975

Gly Gly Ala Gly Thr Ala Ala Thr Thr Ala Thr Thr Ala Cys Gly Ala
            980                 985                 990

Thr Thr Thr Thr Cys Thr Cys Ala  Ala Ala Gly Gly Thr  Gly Thr Ala
        995                 1000                1005

Cys Ala  Ala Gly Ala Ala Cys  Ala Ala Gly Thr Thr  Gly Ala Gly
    1010                1015                1020

Ala Ala  Cys Thr Cys Thr Thr  Gly Thr Ala Ala Thr  Thr Thr Ala
    1025                1030                1035

Ala Ala  Ala Cys Thr Thr Ala  Cys Ala Ala Ala Gly  Thr Ala Thr
    1040                1045                1050

Thr Thr  Thr Gly Gly Gly Cys  Thr Thr Gly Ala Thr  Ala Thr Gly
    1055                1060                1065
```

Ala Ala Gly Thr Thr Thr Ala Ala Thr Thr Cys Gly Cys Thr Gly
1070 1075 1080

Ala Thr Thr Ala Thr Gly Thr Thr Ala Ala Gly Thr Gly Ala Ala
1085 1090 1095

Gly Ala Ala Cys Ala Ala Ala Ala Ala Gly Thr Ala Gly Ala Gly
1100 1105 1110

Ala Gly Ala Gly Ala Thr Ala Thr Ala Ala Ala Gly Cys Thr Ala
1115 1120 1125

Ala Thr Thr Gly Ala Gly Cys Thr Thr Thr Ala Cys Ala Gly Thr
1130 1135 1140

Ala Ala Ala Thr Ala Thr Ala Ala Cys Cys Ala Gly Cys Thr Thr
1145 1150 1155

Ala Thr Ala Cys Ala Ala Ala Gly Thr Ala Gly Cys Thr Cys Ala
1160 1165 1170

Thr Thr Thr Ala Ala Thr Ala Ala Thr Gly Ala Gly Gly Ala Gly
1175 1180 1185

Cys Thr Ala Gly Cys Gly Ala Thr Gly Thr Thr Ala Ala Ala Ala
1190 1195 1200

Gly Ala Gly Ala Ala Ala Thr Thr Ala Thr Thr Cys Thr Cys Ala
1205 1210 1215

Thr Thr Thr Thr Gly Ala
1220

<210> SEQ ID NO 49
<211> LENGTH: 1224
<212> TYPE: PRT
<213> ORGANISM: Phage from Borrelia burgdorferi

<400> SEQUENCE: 49

Gly Thr Gly Thr Gly Thr Gly Ala Thr Thr Thr Ala Ala Gly Ala Ala
1 5 10 15

Ala Ala Ala Cys Ala Ala Ala Ala Cys Thr Ala Ala Thr Ala Gly Ala
20 25 30

Thr Ala Ala Ala Ala Thr Ala Ala Gly Thr Thr Cys Ala Cys Thr Ala
35 40 45

Gly Ala Ala Cys Thr Ala Thr Ala Cys Ala Ala Ala Thr Ala Cys Thr
50 55 60

Cys Ala Ala Thr Ala Thr Thr Thr Thr Thr Thr Ala Gly Ala Ala Ala
65 70 75 80

Thr Thr Ala Cys Ala Thr Thr Gly Ala Ala Ala Ala Thr Gly Thr Ala
85 90 95

Gly Cys Ala Gly Ala Ala Gly Ala Thr Thr Gly Thr Cys Thr Cys Ala
100 105 110

Ala Gly Ala Ala Cys Gly Gly Ala Cys Thr Thr Ala Thr Thr Cys Thr
115 120 125

Thr Gly Ala Gly Ala Gly Thr Gly Cys Thr Gly Cys Cys Cys Ala Cys
130 135 140

Ala Ala Thr Gly Thr Thr Ala Gly Thr Gly Ala Gly Gly Thr Thr Gly
145 150 155 160

Ala Ala Cys Thr Thr Gly Cys Thr Ala Gly Gly Thr Thr Ala Ala Ala
165 170 175

Gly Gly Thr Ala Cys Ala Gly Cys Thr Thr Ala Ala Gly Ala Ala Thr
180 185 190

Gly Cys Thr Cys Thr Gly Cys Thr Thr Ala Ala Thr Thr Gly Thr Ala
195 200 205

```
Thr Thr Ala Thr Ala Ala Gly Cys Thr Ala Cys Cys Gly Thr Thr Thr
    210                 215                 220

Thr Cys Ala Thr Gly Gly Gly Ala Thr Thr Gly Gly Cys Thr Ala Thr
225                 230                 235                 240

Gly Thr Thr Thr Thr Ala Gly Thr Ala Ala Ala Ala Ala Cys Cys Ala
                245                 250                 255

Ala Ala Gly Ala Thr Ala Cys Cys Cys Thr Ala Ala Thr Ala Gly Ala
            260                 265                 270

Thr Cys Thr Cys Gly Ala Ala Cys Ala Ala Cys Cys Cys Gly Thr Thr
        275                 280                 285

Ala Ala Thr Ala Thr Ala Gly Ala Ala Thr Thr Ala Cys Cys Thr Ala
    290                 295                 300

Thr Thr Gly Gly Thr Thr Thr Thr Gly Ala Ala Thr Ala Cys Cys Thr
305                 310                 315                 320

Thr Gly Ala Thr Thr Ala Thr Gly Ala Ala Thr Ala Thr Gly Thr Ala
                325                 330                 335

Ala Gly Ala Gly Ala Thr Thr Thr Gly Gly Gly Ala Gly Thr Thr Gly
            340                 345                 350

Ala Thr Thr Thr Thr Gly Ala Thr Cys Ala Thr Ala Thr Ala Ala Cys
        355                 360                 365

Cys Thr Ala Thr Ala Ala Ala Gly Thr Ala Ala Ala Ala Thr Cys Cys
    370                 375                 380

Ala Ala Cys Ala Ala Thr Ala Ala Gly Ala Ala Cys Ala Ala Thr Thr
385                 390                 395                 400

Cys Thr Thr Thr Ala Gly Ala Cys Gly Cys Ala Gly Thr Thr Ala Ala
                405                 410                 415

Ala Ala Thr Ala Cys Ala Thr Ala Ala Ala Ala Gly Thr Cys Gly Ala
            420                 425                 430

Cys Thr Thr Ala Thr Cys Ala Thr Ala Thr Ala Thr Gly Ala Ala Ala
        435                 440                 445

Ala Cys Thr Thr Thr Gly Ala Thr Thr Ala Thr Ala Thr Cys Thr Thr
    450                 455                 460

Ala Ala Ala Ala Ala Gly Ala Thr Ala Thr Gly Thr Thr Cys Cys Gly
465                 470                 475                 480

Thr Gly Thr Thr Ala Thr Ala Cys Cys Gly Ala Ala Ala Gly Cys Thr
                485                 490                 495

Thr Thr Thr Thr Ala Cys Thr Ala Gly Ala Thr Ala Thr Thr Thr Ala
            500                 505                 510

Thr Thr Thr Ala Thr Thr Thr Gly Ala Ala Ala Ala Gly Ala Thr Ala
        515                 520                 525

Thr Ala Cys Gly Thr Ala Gly Ala Ala Ala Thr Ala Gly Ala Ala Ala
    530                 535                 540

Gly Ala Cys Gly Thr Ala Thr Thr Gly Ala Ala Ala Ala Cys Cys Ala
545                 550                 555                 560

Cys Ala Ala Thr Thr Thr Cys Thr Thr Gly Thr Thr Thr Thr Ala Thr
                565                 570                 575

Ala Ala Ala Gly Ala Thr Gly Ala Ala Thr Cys Thr Thr Thr Ala Gly
            580                 585                 590

Thr Ala Cys Ala Ala Cys Thr Ala Cys Ala Ala Gly Ala Cys Gly Cys
        595                 600                 605

Ala Cys Thr Cys Thr Cys Thr Ala Gly Thr Gly Cys Ala Ala Cys Ala
    610                 615                 620
```

-continued

```
Ala Cys Thr Thr Cys Thr Thr Thr Ala Ala Gly Thr Gly Cys Ala Cys
625                 630                 635                 640

Thr Thr Ala Cys Thr Cys Ala Gly Ala Gly Cys Ala Ala Thr Ala Ala
                645                 650                 655

Thr Gly Ala Thr Ala Gly Gly Gly Gly Ala Ala Gly Thr Gly Gly Cys
            660                 665                 670

Ala Thr Thr Thr Thr Ala Thr Cys Thr Thr Cys Thr Thr Thr Thr Thr
        675                 680                 685

Thr Gly Ala Gly Ala Ala Ala Ala Cys Ala Ala Ala Ala Thr Thr Cys
    690                 695                 700

Ala Ala Ala Cys Ala Ala Thr Cys Ala Thr Ala Gly Thr Ala Ala Ala
705                 710                 715                 720

Gly Ala Thr Ala Thr Thr Thr Cys Thr Ala Ala Thr Thr Thr Ala Ala
                725                 730                 735

Gly Ala Ala Ala Cys Cys Thr Thr Ala Ala Thr Gly Ala Cys Thr Cys
            740                 745                 750

Ala Thr Thr Ala Thr Cys Ala Cys Ala Gly Gly Ala Gly Cys Thr Thr
        755                 760                 765

Gly Cys Thr Ala Gly Gly Cys Thr Ala Ala Ala Ala Ala Gly Cys Ala
    770                 775                 780

Ala Thr Cys Thr Ala Ala Ala Thr Ala Ala Thr Gly Ala Gly Gly Gly
785                 790                 795                 800

Ala Ala Thr Gly Thr Thr Thr Thr Ala Thr Ala Cys Gly Gly Cys Cys
                805                 810                 815

Ala Cys Cys Cys Cys Thr Ala Gly Thr Gly Cys Thr Ala Gly Thr Thr
            820                 825                 830

Thr Ala Gly Ala Gly Gly Thr Thr Ala Thr Thr Ala Ala Ala Thr Ala
        835                 840                 845

Cys Gly Ala Thr Cys Thr Thr Ala Gly Cys Thr Ala Cys Thr Thr Ala
    850                 855                 860

Ala Ala Gly Gly Ala Gly Gly Cys Thr Thr Thr Ala Gly Cys Ala Thr
865                 870                 875                 880

Thr Ala Ala Thr Thr Ala Ala Gly Gly Cys Ala Ala Ala Ala Ala Thr
                885                 890                 895

Thr Gly Gly Thr Gly Cys Ala Gly Ala Thr Ala Cys Thr Ala Ala Ala
            900                 905                 910

Gly Ala Gly Cys Cys Cys Thr Thr Ala Ala Cys Cys Ala Gly Ala Ala
        915                 920                 925

Gly Thr Thr Thr Thr Ala Ala Thr Gly Ala Gly Cys Ala Gly Gly Cys
    930                 935                 940

Thr Ala Ala Ala Gly Gly Ala Cys Thr Ala Gly Gly Ala Ala Ala Thr
945                 950                 955                 960

Gly Ala Thr Gly Gly Thr Ala Ala Ala Gly Gly Thr Gly Ala Thr Ala
                965                 970                 975

Gly Gly Ala Gly Thr Ala Ala Thr Thr Ala Thr Thr Ala Cys Gly Ala
            980                 985                 990

Thr Thr Thr Thr Cys Thr Cys Ala  Ala Ala Gly Gly Thr  Gly Thr Ala
        995                 1000                1005

Cys Ala  Ala Gly Ala Ala Cys  Ala Ala Gly Thr Thr  Gly Ala Gly
    1010                1015                1020

Ala Ala  Cys Thr Cys Thr Thr  Gly Thr Ala Ala Thr  Thr Thr Ala
    1025                1030                1035

Ala Ala  Ala Cys Thr Thr Ala  Cys Ala Ala Ala Gly  Thr Ala Thr
```

1040 1045 1050

Thr Thr Thr Gly Gly Gly Cys Thr Thr Gly Ala Thr Ala Thr Gly
1055 1060 1065

Ala Ala Gly Thr Thr Thr Ala Ala Thr Thr Cys Thr Cys Thr Gly
1070 1075 1080

Ala Thr Thr Ala Thr Gly Thr Thr Ala Ala Gly Thr Gly Ala Ala
1085 1090 1095

Gly Ala Ala Cys Ala Ala Ala Ala Ala Gly Thr Gly Gly Ala Ala
1100 1105 1110

Ala Gly Ala Gly Ala Thr Ala Thr Ala Ala Ala Gly Cys Thr Ala
1115 1120 1125

Ala Thr Thr Gly Ala Gly Cys Thr Thr Thr Ala Cys Ala Gly Thr
1130 1135 1140

Ala Ala Ala Thr Ala Thr Ala Ala Cys Cys Ala Gly Cys Thr Thr
1145 1150 1155

Ala Thr Ala Cys Ala Ala Ala Gly Thr Ala Gly Cys Thr Cys Ala
1160 1165 1170

Thr Thr Thr Ala Ala Thr Ala Ala Thr Gly Ala Gly Gly Ala Gly
1175 1180 1185

Cys Thr Ala Gly Cys Gly Ala Thr Gly Thr Thr Ala Ala Ala Ala
1190 1195 1200

Gly Ala Gly Ala Ala Ala Thr Thr Ala Thr Thr Cys Thr Cys Ala
1205 1210 1215

Thr Thr Thr Thr Gly Ala
1220

<210> SEQ ID NO 50
<211> LENGTH: 1227
<212> TYPE: PRT
<213> ORGANISM: Phage from Borrelia burgdorferi

<400> SEQUENCE: 50

Ala Thr Gly Ala Thr Thr Ala Ala Cys Gly Ala Ala Thr Thr Thr Ala
1 5 10 15

Ala Ala Ala Thr Gly Gly Ala Ala Ala Thr Ala Ala Ala Ala Ala Ala
20 25 30

Cys Ala Ala Thr Ala Ala Ala Thr Cys Cys Ala Ala Ala Ala Thr Cys
35 40 45

Ala Ala Thr Cys Cys Thr Ala Thr Thr Gly Ala Thr Gly Thr Thr Thr
50 55 60

Ala Cys Ala Gly Ala Thr Ala Thr Thr Cys Ala Ala Thr Thr Thr Thr
65 70 75 80

Thr Thr Thr Thr Ala Gly Ala Ala Ala Cys Thr Ala Cys Ala Thr Ala
85 90 95

Gly Ala Ala Ala Gly Thr Ala Cys Cys Gly Cys Ala Gly Ala Ala Gly
100 105 110

Ala Thr Gly Cys Ala Cys Thr Thr Ala Ala Gly Ala Ala Thr Gly Gly
115 120 125

Ala Ala Thr Thr Ala Ala Thr Thr Thr Ala Ala Gly Cys Cys Thr Gly
130 135 140

Cys Thr Thr Gly Ala Ala Ala Ala Gly Thr Cys Thr Thr Gly Cys Thr
145 150 155 160

Thr Gly Ala Ala Ala Gly Ala Ala Ala Gly Cys Ala Gly Cys Ala Ala
165 170 175

-continued

```
Gly Thr Cys Thr Cys Thr Thr Thr Thr Gly Gly Gly Gly Thr Thr Ala
            180                 185                 190

Ala Ala Gly Gly Thr Thr Cys Ala Gly Thr Thr Ala Ala Ala Ala Gly
        195                 200                 205

Ala Ala Gly Cys Thr Cys Thr Thr Cys Thr Thr Gly Ala Ala Gly Cys
    210                 215                 220

Ala Ala Thr Gly Ala Thr Ala Ala Gly Cys Thr Ala Cys Ala Gly Ala
225                 230                 235                 240

Thr Thr Thr Ala Ala Thr Gly Gly Ala Gly Cys Ala Gly Gly Thr Thr
                245                 250                 255

Ala Thr Ala Thr Thr Thr Thr Gly Gly Thr Ala Ala Ala Ala Cys Cys
            260                 265                 270

Cys Ala Ala Ala Ala Gly Thr Gly Ala Ala Gly Ala Thr Gly Ala Ala
        275                 280                 285

Gly Ala Thr Thr Thr Ala Ala Gly Cys Ala Ala Ala Ala Ala Gly Gly
    290                 295                 300

Thr Thr Ala Ala Cys Ala Gly Cys Gly Ala Ala Thr Thr Ala Cys Cys
305                 310                 315                 320

Cys Ala Cys Ala Gly Gly Thr Thr Thr Thr Ala Ala Ala Thr Ala Thr
                325                 330                 335

Thr Thr Gly Gly Ala Thr Thr Thr Thr Cys Ala Ala Ala Ala Ala Ala
            340                 345                 350

Thr Thr Ala Thr Thr Ala Ala Cys Ala Ala Ala Ala Gly Ala Gly Ala
        355                 360                 365

Thr Thr Cys Thr Ala Gly Thr Thr Ala Cys Gly Thr Gly Gly Ala Gly
    370                 375                 380

Thr Ala Cys Cys Thr Thr Thr Cys Thr Ala Ala Cys Thr Cys Ala Ala
385                 390                 395                 400

Ala Ala Gly Ala Cys Cys Cys Gly Gly Ala Thr Gly Ala Thr Thr Thr
                405                 410                 415

Thr Gly Ala Gly Ala Gly Ala Gly Cys Ala Ala Gly Ala Gly Thr Thr
            420                 425                 430

Gly Thr Ala Ala Ala Ala Ala Thr Ala Gly Ala Thr Ala Ala Ala Ala
        435                 440                 445

Gly Cys Ala Gly Ala Gly Thr Ala Ala Thr Ala Ala Thr Thr Thr Ala
    450                 455                 460

Thr Gly Ala Ala Ala Ala Thr Thr Ala Thr Gly Ala Thr Thr Ala Thr
465                 470                 475                 480

Gly Thr Thr Thr Thr Ala Gly Gly Cys Gly Ala Gly Cys Ala Ala Gly
                485                 490                 495

Ala Ala Cys Cys Thr Gly Cys Thr Thr Ala Cys Ala Cys Gly Cys Ala
            500                 505                 510

Ala Ala Gly Thr Thr Thr Gly Cys Thr Gly Cys Thr Thr Ala Ala Cys
        515                 520                 525

Ala Thr Thr Thr Gly Thr Cys Thr Thr Thr Thr Ala Gly Ala Ala Cys
    530                 535                 540

Ala Ala Ala Thr Thr Thr Ala Thr Thr Thr Ala Gly Ala Ala Ala Thr
545                 550                 555                 560

Ala Gly Ala Ala Ala Ala Ala Ala Gly Ala Ala Thr Ala Ala Gly Ala
                565                 570                 575

Ala Ala Thr Thr Ala Thr Ala Ala Thr Thr Thr Thr Thr Thr Gly Thr
            580                 585                 590

Thr Thr Thr Ala Cys Ala Ala Ala Gly Ala Cys Gly Ala Ala Cys Ala
```

```
        595                 600                 605

Thr Thr Thr Gly Gly Thr Gly Gly Gly Ala Cys Thr Thr Gly Thr Thr
    610                 615                 620

Gly Ala Ala Thr Cys Thr Thr Thr Ala Gly Ala Gly Ala Thr Thr Gly
625                 630                 635                 640

Cys Ala Ala Ala Ala Gly Ala Ala Gly Ala Ala Ala Thr Thr Ala Ala
                645                 650                 655

Thr Gly Thr Thr Thr Thr Gly Gly Cys Ala Ala Ala Cys Ala Gly Cys
            660                 665                 670

Ala Ala Ala Gly Gly Cys Ala Ala Ala Ala Thr Ala Thr Thr Thr Thr
        675                 680                 685

Cys Thr Ala Cys Cys Thr Thr Thr Thr Thr Thr Ala Ala Ala Gly Cys
    690                 695                 700

Thr Cys Ala Ala Gly Ala Gly Cys Cys Ala Ala Ala Cys Ala Ala Ala
705                 710                 715                 720

Ala Gly Thr Thr Thr Thr Cys Ala Ala Gly Cys Ala Thr Thr Ala Ala
                725                 730                 735

Gly Thr Ala Gly Cys Gly Thr Cys Thr Cys Thr Gly Ala Cys Gly Ala
            740                 745                 750

Gly Cys Thr Thr Ala Gly Cys Ala Gly Ala Gly Ala Gly Cys Thr Thr
        755                 760                 765

Ala Gly Cys Ala Ala Gly Ala Thr Thr Ala Ala Ala Ala Ala Cys Ala
    770                 775                 780

Cys Thr Cys Thr Ala Ala Ala Cys Ala Ala Thr Gly Ala Thr Gly Gly
785                 790                 795                 800

Ala Ala Thr Thr Thr Thr Thr Thr Ala Cys Ala Cys Ala Gly Cys Ala
                805                 810                 815

Thr Cys Ala Gly Ala Gly Ala Ala Thr Gly Cys Ala Cys Gly Cys Cys
            820                 825                 830

Thr Ala Gly Ala Ala Gly Thr Ala Ala Thr Ala Ala Ala Ala Thr Ala
        835                 840                 845

Thr Gly Ala Thr Thr Thr Ala Gly Ala Gly Thr Thr Thr Thr Thr Ala
    850                 855                 860

Ala Ala Ala Gly Ala Cys Gly Cys Ala Thr Thr Thr Gly Ala Ala Cys
865                 870                 875                 880

Thr Thr Gly Thr Thr Ala Ala Ala Gly Cys Ala Ala Ala Ala Ala Thr
                885                 890                 895

Thr Gly Gly Cys Gly Cys Thr Gly Ala Thr Ala Cys Cys Ala Ala Ala
            900                 905                 910

Gly Ala Gly Cys Cys Thr Thr Thr Ala Ala Cys Cys Ala Gly Ala Ala
        915                 920                 925

Gly Cys Thr Thr Thr Ala Ala Thr Gly Ala Gly Cys Ala Ala Gly Thr
    930                 935                 940

Cys Ala Ala Ala Gly Gly Gly Cys Thr Thr Gly Gly Cys Ala Gly Cys
945                 950                 955                 960

Ala Gly Cys Gly Gly Cys Ala Ala Gly Gly Gly Ala Gly Ala Thr Ala
                965                 970                 975

Ala Ala Ala Gly Cys Ala Ala Thr Thr Ala Thr Thr Ala Thr Gly Ala
            980                 985                 990

Thr Thr Ala Thr Thr Thr Ala Ala  Ala Ala Gly Gly Cys  Gly Thr Thr
        995                 1000                1005

Cys Ala  Ala Gly Ala Ala Thr  Cys Thr Gly Thr Thr  Gly Cys Thr
    1010                1015                1020
```

Ala Ala Thr Gly Cys Gly Thr Gly Cys Ala Ala Thr Cys Thr Cys
1025 1030 1035

Ala Ala Gly Cys Thr Thr Ala Ala Cys Ala Ala Ala Thr Ala Thr
1040 1045 1050

Thr Ala Cys Ala Gly Ala Thr Thr Ala Ala Ala Thr Ala Thr Gly
1055 1060 1065

Ala Ala Gly Thr Thr Thr Ala Ala Thr Gly Ala Gly Cys Thr Thr
1070 1075 1080

Gly Ala Ala Gly Cys Thr Thr Thr Ala Ala Gly Cys Thr Ala Thr
1085 1090 1095

Gly Ala Gly Cys Ala Ala Ala Gly Ala Cys Thr Thr Cys Ala Ala
1100 1105 1110

Ala Ala Ala Gly Ala Cys Ala Ala Thr Thr Thr Gly Cys Thr Thr
1115 1120 1125

Cys Thr Thr Gly Ala Thr Gly Thr Thr Thr Ala Thr Thr Thr Thr
1130 1135 1140

Ala Ala Ala Thr Ala Thr Thr Thr Ala Gly Ala Gly Cys Thr Ala
1145 1150 1155

Ala Thr Thr Ala Ala Ala Ala Ala Thr Gly Ala Ala Ala Ala Thr
1160 1165 1170

Cys Thr Ala Ala Gly Cys Gly Ala Cys Ala Ala Gly Gly Cys Ala
1175 1180 1185

Ala Ala Ala Gly Ala Ala Ala Ala Thr Thr Thr Ala Ala Ala Ala
1190 1195 1200

Gly Ala Ala Cys Ala Ala Thr Thr Ala Ala Gly Thr Thr Thr Gly
1205 1210 1215

Gly Thr Thr Ala Thr Thr Thr Ala Ala
1220 1225

<210> SEQ ID NO 51
<211> LENGTH: 258
<212> TYPE: PRT
<213> ORGANISM: Phage from Borrelia burgdorferi

<400> SEQUENCE: 51

Met Asn Thr Asn Asn Tyr Phe Asn Leu Asn Asn Phe Asn Met Asp Phe
1 5 10 15

Met Leu Lys Leu Phe Gln Asp Tyr Gln Asn Val Leu Asn Glu Asn Lys
20 25 30

Ile Leu Lys Asn Ser Leu Lys Ile Ser Ser Lys Pro Thr Lys Lys Ala
35 40 45

Ser Lys Pro Thr Pro Lys Phe Tyr Leu Thr Pro Lys Ala Ile Lys Ile
50 55 60

Ile Glu Lys Cys Val Lys Ile Leu Lys Lys Ile Asp Pro Ile Ser Gly
65 70 75 80

Trp Phe Leu His Leu Leu Ala Ile Ser Gly Cys Arg Gly Ala Glu Ile
85 90 95

Gln Lys Val Lys Met Gln Asp Ile Thr Pro Leu Leu Asn Lys Thr Gly
100 105 110

Glu Thr Phe Tyr Asn Ile Lys Val Asn Ile Ala Lys Lys Arg Asn Val
115 120 125

Thr Cys Ile Arg Glu Ile Val Ile Lys Ser Glu Glu Phe Glu Ala Ile
130 135 140

Gln Lys Ala His Glu Asn Tyr Phe Asn Glu Lys Asn Leu Asp Ser Arg

```
145                 150                 155                 160

Arg Thr Tyr Leu Phe Gln Lys Thr Lys His Lys Phe Lys Asp Asn Gln
                165                 170                 175

Ile Asp Ile Ile Asn Ile Ser Arg Lys Phe Lys Asn Leu Leu Lys Lys
            180                 185                 190

Ser Gly Phe Arg Ala Asn Lys Ser Leu His Leu Phe Arg Asn Leu Phe
        195                 200                 205

Ile Ser Tyr Leu Lys Ser Asn Gly Tyr Asn Ser Phe Gln Ile Lys Glu
    210                 215                 220

Leu Met Lys Tyr His Ser Thr Ser Glu Ile Asp Asn Ile Tyr Gly Leu
225                 230                 235                 240

Ser Ala Ala Asn Lys Ile His Ala Tyr Lys Cys Met Lys Asn Asn Leu
                245                 250                 255

Lys Leu


<210> SEQ ID NO 52
<211> LENGTH: 67
<212> TYPE: PRT
<213> ORGANISM: Phage from Borrelia burgdorferi

<400> SEQUENCE: 52

Met Asp Thr Ile Lys Leu Thr Glu Leu Leu Ile Asn Leu Asn Glu Ile
1               5                   10                  15

Lys Leu Ile Ala Val Met Ile Phe Val Thr Val Leu Val Leu Gly Val
            20                  25                  30

Leu Ile Leu Leu Lys Pro Leu Leu Lys Asp Ile Leu Thr Ile Val Ile
        35                  40                  45

Gly Lys Ile Phe Lys Asn Gly Asn Gly Asn Gly Lys Asn His Ile Lys
    50                  55                  60

Lys Arg Asp
65


<210> SEQ ID NO 53
<211> LENGTH: 66
<212> TYPE: PRT
<213> ORGANISM: Phage from Borrelia burgdorferi

<400> SEQUENCE: 53

Met Asp Thr Ile Lys Leu Thr Glu Leu Leu Ile Asn Leu Asn Glu Ile
1               5                   10                  15

Lys Leu Ile Ala Val Met Ile Phe Val Thr Val Leu Val Leu Gly Val
            20                  25                  30

Leu Ile Leu Leu Lys Pro Leu Leu Lys Asp Ile Leu Thr Ile Val Ile
        35                  40                  45

Gly Lys Ile Phe Lys Asn Gly Asn Gly Asn Gly Lys Asn His Ile Lys
    50                  55                  60

Lys Arg
65


<210> SEQ ID NO 54
<211> LENGTH: 66
<212> TYPE: PRT
<213> ORGANISM: Phage from Borrelia burgdorferi

<400> SEQUENCE: 54

Met Asp Thr Ile Lys Leu Thr Glu Leu Leu Ile Asn Leu Asn Glu Ile
1               5                   10                  15
```

```
Lys Leu Ile Ala Val Met Ile Phe Val Thr Val Leu Val Leu Gly Val
            20                  25                  30

Leu Ile Leu Leu Lys Pro Leu Leu Lys Asp Ile Leu Thr Ile Val Ile
        35                  40                  45

Gly Lys Ile Phe Lys Asn Gly Asn Gly Asn Gly Lys Asn His Ile Lys
    50                  55                  60

Lys Arg
65


<210> SEQ ID NO 55
<211> LENGTH: 66
<212> TYPE: PRT
<213> ORGANISM: Phage from Borrelia burgdorferi

<400> SEQUENCE: 55

Met Asp Thr Ile Lys Leu Thr Glu Leu Leu Ile Asn Leu Asn Glu Ile
1               5                   10                  15

Lys Leu Ile Ala Val Met Ile Phe Val Thr Val Leu Val Leu Gly Val
            20                  25                  30

Leu Ile Leu Leu Lys Pro Leu Leu Lys Asp Ile Leu Thr Ile Val Ile
        35                  40                  45

Gly Lys Ile Phe Lys Asn Gly Asn Gly Asn Gly Lys Asn His Ile Lys
    50                  55                  60

Lys Arg
65


<210> SEQ ID NO 56
<211> LENGTH: 67
<212> TYPE: PRT
<213> ORGANISM: Phage from Borrelia burgdorferi

<400> SEQUENCE: 56

Met Asp Thr Ile Lys Leu Thr Glu Leu Leu Ile Asn Leu Asn Glu Ile
1               5                   10                  15

Lys Leu Ile Ala Val Met Ile Phe Val Thr Val Leu Val Leu Gly Val
            20                  25                  30

Leu Ile Leu Leu Lys Pro Leu Leu Lys Asp Ile Leu Thr Ile Val Ile
        35                  40                  45

Gly Lys Ile Phe Lys Asn Gly Asn Gly Asn Gly Lys Asn His Ile Lys
    50                  55                  60

Lys Arg Asp
65


<210> SEQ ID NO 57
<211> LENGTH: 67
<212> TYPE: PRT
<213> ORGANISM: Phage from Borrelia burgdorferi

<400> SEQUENCE: 57

Met Asp Thr Ile Lys Leu Thr Glu Leu Leu Ile Asn Leu Asn Glu Ile
1               5                   10                  15

Lys Leu Ile Ala Val Met Ile Phe Val Thr Val Leu Val Leu Gly Val
            20                  25                  30

Leu Ile Leu Leu Lys Pro Leu Leu Lys Asp Ile Leu Thr Ile Val Ile
        35                  40                  45

Gly Lys Ile Phe Lys Asn Gly Asn Gly Asn Gly Lys Asn His Ile Lys
    50                  55                  60

Lys Arg Asp
```

65

<210> SEQ ID NO 58
<211> LENGTH: 67
<212> TYPE: PRT
<213> ORGANISM: Phage from Borrelia burgdorferi

<400> SEQUENCE: 58

Met Asp Thr Ile Lys Leu Thr Glu Leu Leu Ile Asn Leu Asn Glu Ile
1 5 10 15

Lys Leu Ile Ala Val Met Ile Phe Val Thr Val Leu Val Leu Gly Val
20 25 30

Leu Ile Leu Leu Lys Pro Leu Leu Lys Asp Ile Leu Thr Ile Val Ile
35 40 45

Gly Lys Ile Phe Lys Asn Gly Asn Gly Asn Gly Lys Asn His Ile Lys
50 55 60

Lys Arg Asp
65

<210> SEQ ID NO 59
<211> LENGTH: 67
<212> TYPE: PRT
<213> ORGANISM: Phage from Borrelia burgdorferi

<400> SEQUENCE: 59

Met Asp Thr Ile Lys Leu Thr Glu Leu Leu Ile Asn Leu Asn Glu Ile
1 5 10 15

Lys Leu Ile Ala Val Met Ile Phe Val Thr Val Leu Val Leu Gly Val
20 25 30

Leu Ile Leu Leu Lys Pro Leu Leu Lys Asp Ile Leu Thr Ile Val Ile
35 40 45

Gly Lys Ile Phe Lys Asn Gly Asn Gly Asn Gly Lys Asn His Ile Lys
50 55 60

Lys Arg Asp
65

<210> SEQ ID NO 60
<211> LENGTH: 59
<212> TYPE: PRT
<213> ORGANISM: Phage from Borrelia burgdorferi

<400> SEQUENCE: 60

Met Asp Thr Ile Leu Ile Phe Leu Ser Thr Ile Asp Asn Thr Lys Leu
1 5 10 15

Ile Ile Leu Gly Gly Phe Ile Val Leu Val Ile Met Pro Met Ile Leu
20 25 30

Ala Ile Lys Pro Gln Phe Arg Glu Asn Leu Ile Leu Leu Ile Gln Lys
35 40 45

Leu Leu Lys Asn Ile Asn Lys Lys Glu Lys Lys
50 55

<210> SEQ ID NO 61
<211> LENGTH: 115
<212> TYPE: PRT
<213> ORGANISM: Phage from Borrelia burgdorferi

<400> SEQUENCE: 61

Met Lys Leu Ser Lys Asp Asn Val Glu Leu Gly Leu Thr Ser Leu Ser
1 5 10 15

```
Thr Leu Ile Asp Ile Phe Ser Lys Phe Glu Asp Glu Phe Asp Glu Ile
            20                  25                  30

Ala His Lys Gly Phe Phe Leu Val Tyr Glu Leu Tyr Ser His Tyr Lys
        35                  40                  45

Leu Ile Tyr Thr Ala Asn Met Glu Arg Leu Glu Ser Ala Leu Thr Pro
    50                  55                  60

Ala Ile Asn Lys Ala Leu Ala Pro Leu Asn Glu Lys Ile Asn Gln Cys
65                  70                  75                  80

Ile Asp Leu Val Asn Ser Asp Glu Lys Asn Leu Lys Ile Ser Asn Asp
                85                  90                  95

Leu Lys Phe Asn Gln Glu Gly Lys Pro Ile Tyr Lys Glu Arg Thr Asn
            100                 105                 110

Asn Ala Lys
        115


<210> SEQ ID NO 62
<211> LENGTH: 115
<212> TYPE: PRT
<213> ORGANISM: Phage from Borrelia burgdorferi

<400> SEQUENCE: 62

Met Lys Leu Ser Lys Asp Asn Val Glu Leu Gly Leu Thr Ser Leu Ser
1               5                   10                  15

Thr Leu Ile Asp Ile Phe Ser Lys Phe Glu Asp Glu Phe Asp Glu Ile
            20                  25                  30

Ala His Lys Gly Phe Phe Leu Val Tyr Glu Leu Tyr Ser His Tyr Lys
        35                  40                  45

Leu Ile Tyr Thr Ala Asn Met Glu Arg Leu Glu Ser Ala Leu Thr Pro
    50                  55                  60

Ala Ile Asn Lys Ala Leu Ala Pro Leu Asn Glu Lys Ile Asn Gln Cys
65                  70                  75                  80

Ile Asp Leu Val Asn Ser Asp Glu Lys Asn Leu Lys Ile Ser Asn Asp
                85                  90                  95

Leu Lys Phe Asn Gln Glu Gly Lys Pro Ile Tyr Lys Glu Arg Thr Asn
            100                 105                 110

Asn Ala Lys
        115


<210> SEQ ID NO 63
<211> LENGTH: 115
<212> TYPE: PRT
<213> ORGANISM: Phage from Borrelia burgdorferi

<400> SEQUENCE: 63

Met Lys Leu Ser Lys Asp Asn Val Glu Leu Gly Leu Thr Ser Leu Ser
1               5                   10                  15

Thr Leu Ile Asp Ile Phe Ser Lys Phe Glu Asp Glu Phe Asp Glu Ile
            20                  25                  30

Ala His Lys Gly Phe Phe Leu Val Tyr Glu Leu Tyr Ser His Tyr Lys
        35                  40                  45

Leu Ile Tyr Thr Ala Asn Met Glu Arg Leu Glu Ser Ala Leu Thr Pro
    50                  55                  60

Ala Ile Asn Lys Ala Leu Ala Pro Leu Asn Glu Lys Ile Asn Gln Cys
65                  70                  75                  80

Ile Asp Leu Val Asn Ser Asp Glu Lys Asn Leu Lys Ile Ser Asn Asp
                85                  90                  95
```

Leu Lys Phe Asn Gln Glu Gly Lys Pro Ile Tyr Lys Glu Arg Thr Asn
100 105 110

Asn Ala Lys
115

<210> SEQ ID NO 64
<211> LENGTH: 115
<212> TYPE: PRT
<213> ORGANISM: Phage from Borrelia burgdorferi

<400> SEQUENCE: 64

Met Lys Leu Ser Lys Asp Asn Val Glu Leu Gly Leu Thr Ser Leu Ser
1 5 10 15

Thr Leu Ile Asp Ile Phe Ser Lys Phe Glu Asp Glu Phe Asp Glu Ile
20 25 30

Ala His Lys Gly Phe Phe Leu Val Tyr Asp Leu Tyr Ser His Tyr Lys
35 40 45

Leu Ile Tyr Thr Ala Asn Met Glu Arg Leu Glu Ser Ala Leu Thr Pro
50 55 60

Ala Ile Asn Ala Ala Leu Ala Pro Leu Asn Glu Lys Ile Asn Gln Cys
65 70 75 80

Ile Asp Leu Val Asn Ser Asp Glu Lys Asn Leu Lys Ile Ser Asn Asp
85 90 95

Leu Lys Phe Asn Gln Glu Gly Lys Pro Ile Tyr Lys Glu Arg Ile Asn
100 105 110

Asn Ala Lys
115

<210> SEQ ID NO 65
<211> LENGTH: 118
<212> TYPE: PRT
<213> ORGANISM: Phage from Borrelia burgdorferi

<400> SEQUENCE: 65

Met Lys Leu Ser Lys Asp Asn Val Glu Leu Gly Leu Thr Ser Leu Ser
1 5 10 15

Thr Leu Ile Asp Ile Phe Ser Lys Phe Glu Asp Glu Phe Asp Glu Ile
20 25 30

Ala His Lys Gly Phe Phe Leu Val Tyr Glu Leu Tyr Ser His Tyr Lys
35 40 45

Leu Ile Tyr Thr Ala Asn Met Glu Arg Leu Glu Ser Ala Leu Thr Pro
50 55 60

Ala Ile Asn Ala Ala Leu Ala Pro Leu Asn Ala Lys Ile Asn Thr Val
65 70 75 80

Ile Asp Leu Val Asn Ser Asn Asp Lys Asn Leu Lys Ile Ser Asn Asp
85 90 95

Leu Lys Phe Asn Lys Asp Gly Lys Pro Ile Tyr Lys Glu Arg Ala Asn
100 105 110

Asn Ala Lys Glu His Tyr
115

<210> SEQ ID NO 66
<211> LENGTH: 115
<212> TYPE: PRT
<213> ORGANISM: Phage from Borrelia burgdorferi

<400> SEQUENCE: 66

Met Lys Leu Ser Lys Asp Asn Val Glu Leu Gly Leu Thr Ser Leu Ser

-continued

```
1               5                   10                  15

Thr Leu Ile Asp Ile Phe Ser Lys Phe Glu Asp Glu Phe Asp Glu Ile
            20                  25                  30

Ala His Lys Gly Phe Phe Leu Val Tyr Glu Leu Tyr Ser His Tyr Lys
        35                  40                  45

Leu Ile Tyr Thr Ala Asn Met Glu Arg Leu Glu Ser Ala Leu Thr Pro
    50                  55                  60

Ala Ile Asn Ala Ala Leu Ala Pro Leu Asn Glu Lys Ile Asn Gln Cys
65                  70                  75                  80

Ile Asp Leu Val Asn Ser Asp Glu Lys Asn Leu Lys Ile Ser Asn Asp
                85                  90                  95

Leu Lys Phe Asn Gln Glu Gly Lys Pro Ile Tyr Lys Glu Arg Thr Asn
            100                 105                 110

Asn Ala Lys
        115
```

<210> SEQ ID NO 67
<211> LENGTH: 115
<212> TYPE: PRT
<213> ORGANISM: Phage from Borrelia burgdorferi

<400> SEQUENCE: 67

```
Met Lys Leu Ser Lys Asp Asn Val Glu Leu Gly Leu Thr Ser Leu Ser
1               5                   10                  15

Thr Leu Ile Asp Ile Phe Ser Lys Phe Glu Asp Glu Phe Asp Glu Ile
            20                  25                  30

Ala His Lys Gly Phe Phe Leu Val Tyr Glu Leu Tyr Ser His Tyr Lys
        35                  40                  45

Leu Ile Tyr Thr Ala Asn Met Glu Arg Leu Glu Ser Ala Leu Thr Pro
    50                  55                  60

Ala Ile Asn Ala Ala Leu Ala Pro Leu Asn Glu Lys Ile Asn Gln Cys
65                  70                  75                  80

Ile Asp Leu Val Asn Ser Asp Glu Lys Asn Leu Lys Ile Ser Asn Asp
                85                  90                  95

Leu Lys Phe Asn Gln Glu Gly Lys Pro Ile Tyr Lys Glu Arg Thr Asn
            100                 105                 110

Asn Ala Lys
        115
```

<210> SEQ ID NO 68
<211> LENGTH: 115
<212> TYPE: PRT
<213> ORGANISM: Phage from Borrelia burgdorferi

<400> SEQUENCE: 68

```
Met Lys Leu Ser Lys Asp Asn Val Glu Leu Gly Leu Thr Ser Leu Ser
1               5                   10                  15

Thr Leu Ile Asp Ile Phe Ser Lys Phe Glu Asp Glu Phe Asp Glu Ile
            20                  25                  30

Ala His Lys Gly Phe Phe Leu Val Tyr Glu Leu Tyr Ser His Tyr Lys
        35                  40                  45

Leu Ile Tyr Thr Ala Asn Met Glu Arg Leu Glu Ser Ala Leu Thr Pro
    50                  55                  60

Ala Ile Asn Lys Ala Leu Ala Pro Leu Asn Glu Lys Ile Asn Gln Cys
65                  70                  75                  80

Ile Asp Leu Val Asn Ser Asp Glu Lys Asn Leu Lys Ile Ser Asn Asp
```

-continued

```
            85                  90                  95

Leu Lys Phe Asn Gln Glu Gly Lys Pro Ile Tyr Lys Glu Arg Thr Asn
            100                 105                 110

Asn Ala Lys
        115


<210> SEQ ID NO 69
<211> LENGTH: 141
<212> TYPE: PRT
<213> ORGANISM: Phage from Borrelia burgdorferi

<400> SEQUENCE: 69

Met Asn Asn Lys Met Asn Ile Asn Ser Gly Ile Asp Ala Leu Asn Asn
1               5                   10                  15

Leu Tyr Asp Phe Leu Lys Ser Ser Asp Ser Pro Thr Glu Val Lys Val
            20                  25                  30

Glu Lys Gly Ile Tyr Leu Gly Leu Asn Leu Tyr Asn Leu Ile Met Ser
        35                  40                  45

Ile Tyr Lys Asp Lys Ile Thr Thr Leu Glu Lys Glu Glu Ser Leu Lys
    50                  55                  60

Ile Leu Asn Glu Ile Lys Asn Val Asn Asn Lys Ile Thr Gln Leu Ile
65                  70                  75                  80

Ser Ser Ile Asn Asp Glu Arg Asp Ala Ser Ile Ile Glu His Leu Arg
                85                  90                  95

Glu Glu Arg Asn Glu Leu Met Ser Ile Lys Thr Gln Ala Leu Gln Glu
            100                 105                 110

Gln Ile Lys Glu Phe Pro Glu Asn Thr Ser Thr Ala Asn Ser Lys Ala
        115                 120                 125

Gln Asn Leu Lys Glu Asn Lys Gly Asp Lys Ile Ala Asn
    130                 135                 140


<210> SEQ ID NO 70
<211> LENGTH: 17
<212> TYPE: DNA
<213> ORGANISM: Synthetic probe

<400> SEQUENCE: 70

gtgaacttat atcaaac                                                  17


<210> SEQ ID NO 71
<211> LENGTH: 17
<212> TYPE: DNA
<213> ORGANISM: Synthetic probe

<400> SEQUENCE: 71

ataatcttct tttcatt                                                  17


<210> SEQ ID NO 72
<211> LENGTH: 20
<212> TYPE: DNA
<213> ORGANISM: Synthetic probe

<400> SEQUENCE: 72

acagtgctgg ttttaggagt                                               20


<210> SEQ ID NO 73
<211> LENGTH: 22
<212> TYPE: DNA
<213> ORGANISM: Synthetic probe
```

<400> SEQUENCE: 73
tgccattacc attaccattc tt 22

<210> SEQ ID NO 74
<211> LENGTH: 23
<212> TYPE: DNA
<213> ORGANISM: Synthetic probe

<400> SEQUENCE: 74
ttgatgaaat tgcacataaa gga 23

<210> SEQ ID NO 75
<211> LENGTH: 20
<212> TYPE: DNA
<213> ORGANISM: Synthetic probe

<400> SEQUENCE: 75
gctggggtta atgcactctc 20

<210> SEQ ID NO 76
<211> LENGTH: 21
<212> TYPE: DNA
<213> ORGANISM: Synthetic probe

<400> SEQUENCE: 76
aacagtgctg gttttaggag t 21

<210> SEQ ID NO 77
<211> LENGTH: 24
<212> TYPE: DNA
<213> ORGANISM: Synthetic probe

<400> SEQUENCE: 77
agataggttt tccttcctga ttga 24

<210> SEQ ID NO 78
<211> LENGTH: 555
<212> TYPE: DNA
<213> ORGANISM: Phage from Borrelia burgdorferi

<400> SEQUENCE: 78
atggatacta ttaaattaac cgaacttctt atcaatttaa acgaaattaa acttatagcg 60
gtaatgattt ttgtaacagt gctggtttta ggagtattaa ttcttctcaa gcctttacta 120
aaagacatat tgactattgt aataggcaag atttttaaga atggtaatgg taatggcaaa 180
aatcacatta aaaaaagaga ttaacttatg aaattatcca aagataatgt tgagcttgga 240
cttacgtctt tatcaaccct tattgatata ttttctaaat ttgaagatga atttgatgaa 300
attgcacata aaggattctt tttggtttat gagctgtatt ctcattataa attaatctat 360
acagcaaata tggaaagact tgagagtgca ttaaccccag caataaataa agcactcgct 420
ccattaaatg aaaaaatcaa tcaatgcatt gacttagtta attctgatga aaaaaatctc 480
aaaatatcta atgatctgaa attcaatcag gaaggaaaac ctatctataa ggaaagaaca 540
aataatgcaa aataa 555

<210> SEQ ID NO 79
<211> LENGTH: 21
<212> TYPE: DNA
<213> ORGANISM: Synthetic probe

<400> SEQUENCE: 79
gagtggatag caagcactga t 21

<210> SEQ ID NO 80
<211> LENGTH: 22
<212> TYPE: DNA
<213> ORGANISM: Synthetic probe

<400> SEQUENCE: 80
atcatcaact cgctccataa ca 22

<210> SEQ ID NO 81
<211> LENGTH: 26
<212> TYPE: DNA
<213> ORGANISM: Synthetic probe

<400> SEQUENCE: 81
tgctgggtct aaatatgcta tcgggc 26

<210> SEQ ID NO 82
<211> LENGTH: 20
<212> TYPE: DNA
<213> ORGANISM: Synthetic probe

<400> SEQUENCE: 82
agactaagat gcgggcaaga 20

<210> SEQ ID NO 83
<211> LENGTH: 20
<212> TYPE: DNA
<213> ORGANISM: synthetic probe

<400> SEQUENCE: 83
ttgcatcaag agcgtcatca 20

<210> SEQ ID NO 84
<211> LENGTH: 1359
<212> TYPE: DNA
<213> ORGANISM: B.miyamotoi

<400> SEQUENCE: 84
atggatatat acaagagcag tttgtttgtt aaatacagaa aaaaatataa acataaatat 60
gggattgata tacaagatta cattaagcct aaaagtttag atgttaactt taaagaattt 120
gagcaaacac atttaacacc aaaacaatta gcagttataa atagtattga agaacataag 180
caaactaaga ttattctttg tggagggatt gccagtggta aaacattctt agcatgttat 240
ctattcttaa aaatactgct tactggtaga catttataca agcaagatac caataatttt 300
attttgggca attcacaaaa atctttagaa cttaatgtat tggggcaatt tgataaaatt 360
gctagtatgc ttaatatact atttgtaccc aagtattcta atacttctta ttttgaagta 420
gattccttaa gagttaattt atatggtgga gataaggcaa gtgactttga acgcttcaga 480
ggctctaatt ctgctatcat ctatataaat gaagcaacta ctcttcataa agaaacatta 540
atagaatgtc ttaaaagact cagagtaggc aagcaaagta tcatctttga taccaatcct 600
gatcatcctg agcattactt taaaactgat tatattgata atactgatat ttatgctaca 660
tataacttta caacatatga taacgcatta ataccettag actttattaa gacacaagaa 720
caactatata aagaccaacc aacatataaa gcaagagtgc tcttaggaga atgggttgca 780
tctaatgagg ctatatttac taatgttaat cttataagta aagaaaaata tgaatttaaa 840

```
tccccaatag cctacctaga tcctgcttat agtattggtt gtgataacag tgcactttgt    900

gtattagagc gactagataa caagtattat gcatttatat ttcaagacaa acttccagca    960

agtgacccaa gagtattaaa tacaattatg actatactag aaaacttaaa tgtgcataca   1020

ctttatattg aagataggga taatactact gggaaaggta gtattactaa agtgtttatt   1080

aatcttagag cacatatgaa tcatcattat agaattgctc ctattaaacc cataagtaat   1140

aaatttacta gaattgctac tttaataggt cctattaatt catctaattt aagtattcta   1200

gattttagta gtaaatctgc tattgctgat atatacaaat ataaaggtga tgataagact   1260

aatgatgatt caattgatag cctgtcagct ctttatatgt tacttactct gaataagagt   1320

tctttaaaag cacattttac taaaataagg ttcatataa                          1359


<210> SEQ ID NO 85
<211> LENGTH: 452
<212> TYPE: PRT
<213> ORGANISM: B. miyamotoi

<400> SEQUENCE: 85

Met Asp Ile Tyr Lys Ser Ser Leu Phe Val Lys Tyr Arg Lys Lys Tyr
1               5                   10                  15

Lys His Lys Tyr Gly Ile Asp Ile Gln Asp Tyr Ile Lys Pro Lys Ser
            20                  25                  30

Leu Asp Val Asn Phe Lys Glu Phe Glu Gln Thr His Leu Thr Pro Lys
        35                  40                  45

Gln Leu Ala Val Ile Asn Ser Ile Glu Glu His Lys Gln Thr Lys Ile
    50                  55                  60

Ile Leu Cys Gly Gly Ile Ala Ser Gly Lys Thr Phe Leu Ala Cys Tyr
65                  70                  75                  80

Leu Phe Leu Lys Ile Leu Leu Thr Gly Arg His Leu Tyr Lys Gln Asp
                85                  90                  95

Thr Asn Asn Phe Ile Leu Gly Asn Ser Gln Lys Ser Leu Glu Leu Asn
            100                 105                 110

Val Leu Gly Gln Phe Asp Lys Ile Ala Ser Met Leu Asn Ile Leu Phe
        115                 120                 125

Val Pro Lys Tyr Ser Asn Thr Ser Tyr Phe Glu Val Asp Ser Leu Arg
    130                 135                 140

Val Asn Leu Tyr Gly Gly Asp Lys Ala Ser Asp Phe Glu Arg Phe Arg
145                 150                 155                 160

Gly Ser Asn Ser Ala Ile Ile Tyr Ile Asn Glu Ala Thr Thr Leu His
                165                 170                 175

Lys Glu Thr Leu Ile Glu Cys Leu Lys Arg Leu Arg Val Gly Lys Gln
            180                 185                 190

Ser Ile Ile Phe Asp Thr Asn Pro Asp His Pro Glu His Tyr Phe Lys
        195                 200                 205

Thr Asp Tyr Ile Asp Asn Thr Asp Ile Tyr Ala Thr Tyr Asn Phe Thr
    210                 215                 220

Thr Tyr Asp Asn Ala Leu Ile Pro Leu Asp Phe Ile Lys Thr Gln Glu
225                 230                 235                 240

Gln Leu Tyr Lys Asp Gln Pro Thr Tyr Lys Ala Arg Val Leu Leu Gly
                245                 250                 255

Glu Trp Val Ala Ser Asn Glu Ala Ile Phe Thr Asn Val Asn Leu Ile
            260                 265                 270

Ser Lys Glu Lys Tyr Glu Phe Lys Ser Pro Ile Ala Tyr Leu Asp Pro
        275                 280                 285
```

-continued

```
Ala Tyr Ser Ile Gly Cys Asp Asn Ser Ala Leu Cys Val Leu Glu Arg
    290                 295                 300

Leu Asp Asn Lys Tyr Tyr Ala Phe Ile Phe Gln Asp Lys Leu Pro Ala
305                 310                 315                 320

Ser Asp Pro Arg Val Leu Asn Thr Ile Met Thr Ile Leu Glu Asn Leu
                325                 330                 335

Asn Val His Thr Leu Tyr Ile Glu Asp Arg Asp Asn Thr Thr Gly Lys
            340                 345                 350

Gly Ser Ile Thr Lys Val Phe Ile Asn Leu Arg Ala His Met Asn His
        355                 360                 365

His Tyr Arg Ile Ala Pro Ile Lys Pro Ile Ser Asn Lys Phe Thr Arg
    370                 375                 380

Ile Ala Thr Leu Ile Gly Pro Ile Asn Ser Ser Asn Leu Ser Ile Leu
385                 390                 395                 400

Asp Phe Ser Ser Lys Ser Ala Ile Ala Asp Ile Tyr Lys Tyr Lys Gly
                405                 410                 415

Asp Asp Lys Thr Asn Asp Asp Ser Ile Asp Ser Leu Ser Ala Leu Tyr
            420                 425                 430

Met Leu Leu Thr Leu Asn Lys Ser Ser Leu Lys Ala His Phe Thr Lys
        435                 440                 445

Ile Arg Phe Ile
    450
```

<210> SEQ ID NO 86
<211> LENGTH: 810
<212> TYPE: DNA
<213> ORGANISM: B. hermsii

<400> SEQUENCE: 86

```
atggatatat ataaactacc tctttttaag gaaatgcaaa aagaatacaa gcgtgaattt      60

ggtattgata tagcagattt aattaaactg aaagcagctg ttattgattt tagagggttt     120

gaaaagacat atttaactaa gaaacaatgt gaggttttaa aattaattga gaataataat     180

cgaagtaaaa ttatcctgtc aggtggtatt gccagtggta aaacattctt ggcttgctat     240

ttatatctaa agatgctcat taagaataga catttttata agcaggatac caataatttt     300

atattaggta attcccaaaa atcattagag attaatgttt tagggcagtt tgaaaagatt     360

gctagcatgc taagagtacc ctttacgcca aagttttcta atacatcata ttttgaaata     420

gactccttaa gagtcaatct atatggtgga gataaggcaa gtgattttga aaggtttaga     480

ggaagcaatt ccgctcttat ttatgtaaat gaagcaacta cactgcataa ggaaacgcta     540

atagagtgct taaagagact tagagtaggt atggaaacta ttatatttga tacaaatcca     600

gacagtccag aacatttctt taaaactgat tatattgata acaagaaaac ttattctaca     660

tataacttta caacatatga taatgaacta atatcaaaag aatttattaa aacccaagaa     720

gagatttaca gggacatgcc aacatataag gcgagggtac tcttggggag aatgggttgc     780

gtcatacgat tcgatattta ccaatattaa                                       810
```

<210> SEQ ID NO 87
<211> LENGTH: 269
<212> TYPE: PRT
<213> ORGANISM: B. hermsii

<400> SEQUENCE: 87

```
Met Asp Ile Tyr Lys Leu Pro Leu Phe Lys Glu Met Gln Lys Glu Tyr
```

-continued

```
1               5                   10                  15

Lys Arg Glu Phe Gly Ile Asp Ile Ala Asp Leu Ile Lys Leu Lys Ala
            20                  25                  30

Ala Val Ile Asp Phe Arg Gly Phe Glu Lys Thr Tyr Leu Thr Lys Lys
        35                  40                  45

Gln Cys Glu Val Leu Lys Leu Ile Glu Asn Asn Asn Arg Ser Lys Ile
    50                  55                  60

Ile Leu Ser Gly Gly Ile Ala Ser Gly Lys Thr Phe Leu Ala Cys Tyr
65                  70                  75                  80

Leu Tyr Leu Lys Met Leu Ile Lys Asn Arg His Phe Tyr Lys Gln Asp
                85                  90                  95

Thr Asn Asn Phe Ile Leu Gly Asn Ser Gln Lys Ser Leu Glu Ile Asn
            100                 105                 110

Val Leu Gly Gln Phe Glu Lys Ile Ala Ser Met Leu Arg Val Pro Phe
        115                 120                 125

Thr Pro Lys Phe Ser Asn Thr Ser Tyr Phe Glu Ile Asp Ser Leu Arg
    130                 135                 140

Val Asn Leu Tyr Gly Gly Asp Lys Ala Ser Asp Phe Glu Arg Phe Arg
145                 150                 155                 160

Gly Ser Asn Ser Ala Leu Ile Tyr Val Asn Glu Ala Thr Thr Leu His
                165                 170                 175

Lys Glu Thr Leu Ile Glu Cys Leu Lys Arg Leu Arg Val Gly Met Glu
            180                 185                 190

Thr Ile Ile Phe Asp Thr Asn Pro Asp Ser Pro Glu His Phe Phe Lys
        195                 200                 205

Thr Asp Tyr Ile Asp Asn Lys Lys Thr Tyr Ser Thr Tyr Asn Phe Thr
    210                 215                 220

Thr Tyr Asp Asn Glu Leu Ile Ser Lys Glu Phe Ile Lys Thr Gln Glu
225                 230                 235                 240

Glu Ile Tyr Arg Asp Met Pro Thr Tyr Lys Ala Arg Val Leu Leu Gly
                245                 250                 255

Arg Met Gly Cys Val Ile Arg Phe Asp Ile Tyr Gln Tyr
            260                 265
```

<210> SEQ ID NO 88
<211> LENGTH: 26
<212> TYPE: DNA
<213> ORGANISM: Synthetic probe

<400> SEQUENCE: 88
agtgcacttt gtgtgcttga aatggt 26

<210> SEQ ID NO 89
<211> LENGTH: 22
<212> TYPE: DNA
<213> ORGANISM: Synthetic probe

<400> SEQUENCE: 89
agcctaccta gatcctgctt at 22

<210> SEQ ID NO 90
<211> LENGTH: 20
<212> TYPE: DNA
<213> ORGANISM: Synthetic probe

<400> SEQUENCE: 90
gggtcacttg ctggtagttt 20

<210> SEQ ID NO 91
<211> LENGTH: 23
<212> TYPE: DNA
<213> ORGANISM: Synthetic probe

<400> SEQUENCE: 91
acgcttcaga ggctctaatt ctg 23

<210> SEQ ID NO 92
<211> LENGTH: 19
<212> TYPE: DNA
<213> ORGANISM: Synthetic probe

<400> SEQUENCE: 92
gtggagataa ggcaagtga 19

<210> SEQ ID NO 93
<211> LENGTH: 22
<212> TYPE: DNA
<213> ORGANISM: Synthetic probe

<400> SEQUENCE: 93
ctttatgaag agtagttgct tc 22

<210> SEQ ID NO 94
<211> LENGTH: 29
<212> TYPE: DNA
<213> ORGANISM: synthetic probe

<400> SEQUENCE: 94
aggcaccaat agcatattta gatcctgca 29

<210> SEQ ID NO 95
<211> LENGTH: 20
<212> TYPE: DNA
<213> ORGANISM: synthetic probe

<400> SEQUENCE: 95
ggagaatggg ttgcgtcata 20

<210> SEQ ID NO 96
<211> LENGTH: 23
<212> TYPE: DNA
<213> ORGANISM: synthetic probe

<400> SEQUENCE: 96
gcgcagtatt atcacctcca ata 23

<210> SEQ ID NO 97
<211> LENGTH: 201
<212> TYPE: DNA
<213> ORGANISM: Borrelia parkeri

<400> SEQUENCE: 97
ctttatctgt gtctttacct tgttttttat cttactagct aaaatagtta gtatatcttt 60
gattgctggc ttgaagatca gtccaagact taagataaag gcaccaataa taactaactt 120
cacttcattg atgttaatca gttgaagtaa aaaatttaat acattattct caacttcatt 180
caactttatg tctcctctca t 201

<210> SEQ ID NO 98

-continued

<211> LENGTH: 213
<212> TYPE: DNA
<213> ORGANISM: Borrelia turicatae

<400> SEQUENCE: 98
atgaaaggag acataaagtt gaatgaactt gatagtaatt tattaaaatt tttacttcaa 60
ctaattaaca tcaatgaaat gaagttagtt attattggtg cctttatctt aagtcttggt 120
ctgattttca agccagcaat caaagatata ctaactattt tagtaagtaa gataaaaaca 180
cgggttaaag acacagataa aggggaggat tta 213

<210> SEQ ID NO 99
<211> LENGTH: 192
<212> TYPE: DNA
<213> ORGANISM: Borrelia hermsii

<400> SEQUENCE: 99 atccccccttt tctttgtctc tgtcatgtat ttttatctta cttaataaga tacttagtat 60
atctttgatt actggtttga aaatcaaacc caaacttaat ataaaaatac taataatgat 120
taactttact tcattgatgt taattagttg aagtaaaaaa tctaatatgt tattaatgct 180
taattcattc aa 192

<210> SEQ ID NO 100
<211> LENGTH: 210
<212> TYPE: DNA
<213> ORGANISM: Borrelia coriaceae

<400> SEQUENCE: 100
atgcgcggcg ataacctgaa cgaagtgaac aacaacctgc tggattttct gctgcagctg 60
attagcgtga acgaagtgaa actgattatt attggcattt ttattctggg cattggcctg 120
atttttaaac cgaccattaa agatatgctg aacattattg cgaacaaaat taaaaccaac 180
gataaagata aaaacgataa agaaaacaaa 210

<210> SEQ ID NO 101
<211> LENGTH: 321
<212> TYPE: DNA
<213> ORGANISM: Borrelia hermsii

<400> SEQUENCE: 101
atgatacttg atcgtaattc tttagatact gctttaaatg caatcgtaac attatttgac 60
acactatcta attttgaaga tgggtcgttt aatgaaaatg ctcataaaac attcatgcta 120
ctaaacgaca tttacacaga atatcagatt atctatacac aaaatatgga aaggttagag 180
aatgccttaa ctccgcaaat aagagaaaca cttgaaccta tccaaactaa aatcaaaaaa 240
tttatagaaa aggttaatag caatccagat aatatgcaat taccattaga aatctcatca 300
attgaaaagg aggtcaaatg a 321

<210> SEQ ID NO 102
<211> LENGTH: 1212
<212> TYPE: DNA
<213> ORGANISM: Borrelia turicatae

<400> SEQUENCE: 102
atgatttcaa atagcaatat caacgcaaga gagttatata agtattcaat attttttaga 60
aactatattt caaatgtagc agaggacact cttaagaatg gaattacctt aaatagtatt 120
gatactgctt ttaatgttaa tgatgcttta gaagccttaa aaatagagtt aaaagaagca 180

-continued ttattgcagt gtttaattag ttaccgtttt aatggtgttg gatacatttt agttaaaact 240
gctgacttac ttgaagattt acatttaagc gtgaacctag aacttcctat tgggtttatg 300
tatcttgact ataacaatgt tcgtgatgag ggcctgact ttaattatat aacatacatt 360
ttcaaagtaa atacagatga gaagatatct tatagagagt tgaagattca taagaataga 420
gtaatcatac actctaatta tgattatata cttaaagctt acagtccatg ttatacgcaa 480
agctttttgc ttaatatata tctttttgaa caaatatata aagaaataga gaggagaata 540
gagcaacata actttttatt ttacaaggat gaatcattag taacattaca agatgcctta 600
agtgatgcta cgacttcatt agagatttta actaagggcg ttaatgataa gccacgtata 660
ttctctaatc tatttaaaag aaatgtagat gaaaatcata taagcacatt taagagtgta 720
aatagagatt tagagcgaga gcttacgcgg cttaaatcta acttaaataa taatggtatt 780
ttttacagtg gaacacctga tgcgtcactg gaggttatta agtatgactt aacctattta 840
aaggaagcat tagccttagt aaaggcaaag ataggtgctg atacaaaaga gccattaact 900
agaagtttta atgagcaaac taaggggctt ggaaatgatg ggaaagggga taggtctaat 960
tattatgact ttttaaaaag tgttcaagaa caaattgaag ttactattaa tagtaaactt 1020
gttaagtatt tcaatcttaa gatgcatttt aattcacttt atgtgttaag tgaagaagaa 1080
aaaatagagc gagatatgag attacttgaa atgtatgaca agtatgtagc tttaatgcta 1140
aatcctgcct taagtaaagt tgataaggca aatttacaag acagattatt tatgaaaata 1200
aaaggagatt aa 1212

<210> SEQ ID NO 103
<211> LENGTH: 759
<212> TYPE: DNA
<213> ORGANISM: Borrelia turicatae

<400> SEQUENCE: 103
atgaaagaga cacatttaat taactgcaat cttaacttaa aaattaaaga attagagctg 60
caaaatgaac gcttaagtga agaattaact ctacttaaaa gcaatagcaa aactaaaaat 120
actaaaaaat tatcccctcc tgtaagattt tatctaaatg acaggacaat taaactagta 180
aaacgttcta tagagagact taaagaacaa gacccaatct ctggatggtt tgtacattta 240
ctctcaatta ctggttgtag ggtgttgaa atgcaaaatg taaaacttac tgatatatat 300
aaagagacaa gcagtaatgg tgaagtattt tattctattc gtgttaatgt agctaaaaag 360
cgtagcaata tctgtataag agaagtagtt attagtaagc ttgaatttga ttctattatg 420
agggcacatc aagaatattt caactctaga gataaagaca gtaggcgtac ttatctattt 480
caaaaaagta aacttaaatt ccgtgacaac aaaattaaca taactgaaat ttcaaaacag 540
tttaaggaat tactaattaa gggaggattt aaacatcgca aatctctaca tatactccgt 600
aatatattta tagcatcact taaagctaaa ggatataatt catttgaaat taaagagctt 660
atgaaatact catctacttc ggagattgat aatgtttatg gactctcaag tgcaagtaaa 720
atacaggctt acaaagatat caaaactagc ttgaaataa 759

<210> SEQ ID NO 104
<211> LENGTH: 70
<212> TYPE: PRT
<213> ORGANISM: Borrelia parkeri

<400> SEQUENCE: 104

-continued

Met Asn Glu Val Glu Asn Asn Val Leu Asn Phe Leu Leu Gln Leu Ile
1               5                   10                  15

Asn Ile Asn Glu Val Lys Leu Val Ile Ile Gly Ala Phe Ile Leu Ser
            20                  25                  30

Leu Gly Leu Ile Phe Lys Pro Ala Ile Lys Asp Ile Leu Thr Ile Leu
        35                  40                  45

Ala Ser Lys Ile Lys Asn Lys Val Lys Thr Gln Ile Lys Glu Arg Thr
    50                  55                  60

Tyr Glu Ile Lys His Cys
65                  70

<210> SEQ ID NO 105
<211> LENGTH: 71
<212> TYPE: PRT
<213> ORGANISM: Borrelia turicatae

<400> SEQUENCE: 105

Met Lys Gly Asp Ile Lys Leu Asn Glu Leu Asp Ser Asn Leu Leu Lys
1               5                   10                  15

Phe Leu Leu Gln Leu Ile Asn Ile Asn Glu Met Lys Leu Val Ile Ile
            20                  25                  30

Gly Ala Phe Ile Leu Ser Leu Gly Leu Ile Phe Lys Pro Ala Ile Lys
        35                  40                  45

Asp Ile Leu Thr Ile Leu Val Ser Lys Ile Lys Thr Arg Val Lys Asp
    50                  55                  60

Thr Asp Lys Gly Glu Asp Leu
65                  70

<210> SEQ ID NO 106
<211> LENGTH: 65
<212> TYPE: PRT
<213> ORGANISM: Borrelia hermsii

<400> SEQUENCE: 106

Met Asn Glu Leu Ser Ile Asn Asn Ile Leu Asp Phe Leu Leu Gln Leu
1               5                   10                  15

Ile Asn Ile Asn Glu Val Lys Leu Ile Ile Ile Ser Ile Phe Ile Leu
            20                  25                  30

Ser Leu Gly Leu Ile Phe Lys Pro Val Ile Lys Asp Ile Leu Ser Ile
        35                  40                  45

Leu Leu Ser Lys Ile Lys Ile His Asp Arg Asp Lys Glu Lys Gly Asp
    50                  55                  60

Leu
65

<210> SEQ ID NO 107
<211> LENGTH: 70
<212> TYPE: PRT
<213> ORGANISM: Borrelia coriaceae

<400> SEQUENCE: 107

Met Arg Gly Asp Asn Leu Asn Glu Val Asn Asn Asn Leu Leu Asp Phe
1               5                   10                  15

Leu Leu Gln Leu Ile Ser Val Asn Glu Val Lys Leu Ile Ile Ile Gly
            20                  25                  30

Ile Phe Ile Leu Gly Ile Gly Leu Ile Phe Lys Pro Thr Ile Lys Asp
        35                  40                  45

Met Leu Asn Ile Ile Ala Asn Lys Ile Lys Thr Asn Asp Lys Asp Lys

```
    50                  55                  60

Asn Asp Lys Glu Asn Lys
65                  70


<210> SEQ ID NO 108
<211> LENGTH: 106
<212> TYPE: PRT
<213> ORGANISM: Borrelia hermsii

<400> SEQUENCE: 108

Met Ile Leu Asp Arg Asn Ser Leu Asp Thr Ala Leu Asn Ala Ile Val
1               5                   10                  15

Thr Leu Phe Asp Thr Leu Ser Asn Phe Glu Asp Gly Ser Phe Asn Glu
            20                  25                  30

Asn Ala His Lys Thr Phe Met Leu Leu Asn Asp Ile Tyr Thr Glu Tyr
        35                  40                  45

Gln Ile Ile Tyr Thr Gln Asn Met Glu Arg Leu Glu Asn Ala Leu Thr
    50                  55                  60

Pro Gln Ile Arg Glu Thr Leu Glu Pro Ile Gln Thr Lys Ile Lys Lys
65                  70                  75                  80

Phe Ile Glu Lys Val Asn Ser Asn Pro Asp Asn Met Gln Leu Pro Leu
                85                  90                  95

Glu Ile Ser Ser Ile Glu Lys Glu Val Lys
            100                 105


<210> SEQ ID NO 109
<211> LENGTH: 403
<212> TYPE: PRT
<213> ORGANISM: Borrelia turicatae

<400> SEQUENCE: 109

Met Ile Ser Asn Ser Asn Ile Asn Ala Arg Glu Leu Tyr Lys Tyr Ser
1               5                   10                  15

Ile Phe Phe Arg Asn Tyr Ile Ser Asn Val Ala Glu Asp Thr Leu Lys
            20                  25                  30

Asn Gly Ile Thr Leu Asn Ser Ile Asp Thr Ala Phe Asn Val Asn Asp
        35                  40                  45

Ala Leu Glu Ala Leu Lys Ile Glu Leu Lys Glu Ala Leu Leu Gln Cys
    50                  55                  60

Leu Ile Ser Tyr Arg Phe Asn Gly Val Gly Tyr Ile Leu Val Lys Thr
65                  70                  75                  80

Ala Asp Leu Leu Glu Asp Leu His Leu Ser Val Asn Leu Glu Leu Pro
                85                  90                  95

Ile Gly Phe Met Tyr Leu Asp Tyr Asn Asn Val Arg Asp Glu Gly Pro
            100                 105                 110

Asp Phe Asn Tyr Ile Thr Tyr Ile Phe Lys Val Asn Thr Asp Glu Lys
        115                 120                 125

Ile Ser Tyr Arg Glu Leu Lys Ile His Lys Asn Arg Val Ile Ile His
    130                 135                 140

Ser Asn Tyr Asp Tyr Ile Leu Lys Ala Tyr Ser Pro Cys Tyr Thr Gln
145                 150                 155                 160

Ser Phe Leu Leu Asn Ile Tyr Leu Phe Glu Gln Ile Tyr Lys Glu Ile
                165                 170                 175

Glu Arg Arg Ile Glu Gln His Asn Phe Leu Phe Tyr Lys Asp Glu Ser
            180                 185                 190

Leu Val Thr Leu Gln Asp Ala Leu Ser Asp Ala Thr Thr Ser Leu Glu
```

```
        195                 200                 205

Ile Leu Thr Lys Gly Val Asn Asp Lys Pro Arg Ile Phe Ser Asn Leu
    210                 215                 220

Phe Lys Arg Asn Val Asp Glu Asn His Ile Ser Thr Phe Lys Ser Val
225                 230                 235                 240

Asn Arg Asp Leu Glu Arg Glu Leu Thr Arg Leu Lys Ser Asn Leu Asn
                245                 250                 255

Asn Asn Gly Ile Phe Tyr Ser Gly Thr Pro Asp Ala Ser Leu Glu Val
            260                 265                 270

Ile Lys Tyr Asp Leu Thr Tyr Leu Lys Glu Ala Leu Ala Leu Val Lys
        275                 280                 285

Ala Lys Ile Gly Ala Asp Thr Lys Glu Pro Leu Thr Arg Ser Phe Asn
    290                 295                 300

Glu Gln Thr Lys Gly Leu Gly Asn Asp Gly Lys Gly Asp Arg Ser Asn
305                 310                 315                 320

Tyr Tyr Asp Phe Leu Lys Ser Val Gln Glu Gln Ile Glu Val Thr Ile
                325                 330                 335

Asn Ser Lys Leu Val Lys Tyr Phe Asn Leu Lys Met His Phe Asn Ser
            340                 345                 350

Leu Tyr Val Leu Ser Glu Glu Glu Lys Ile Glu Arg Asp Met Arg Leu
        355                 360                 365

Leu Glu Met Tyr Asp Lys Tyr Val Ala Leu Met Leu Asn Pro Ala Leu
    370                 375                 380

Ser Lys Val Asp Lys Ala Asn Leu Gln Asp Arg Leu Phe Met Lys Ile
385                 390                 395                 400

Lys Gly Asp


<210> SEQ ID NO 110
<211> LENGTH: 252
<212> TYPE: PRT
<213> ORGANISM: Borrelia turicatae

<400> SEQUENCE: 110

Met Lys Glu Thr His Leu Ile Asn Cys Asn Leu Asn Leu Lys Ile Lys
1               5                   10                  15

Glu Leu Glu Leu Gln Asn Glu Arg Leu Ser Glu Glu Leu Thr Leu Leu
            20                  25                  30

Lys Ser Asn Ser Lys Thr Lys Asn Thr Lys Lys Leu Ser Pro Pro Val
        35                  40                  45

Arg Phe Tyr Leu Asn Asp Arg Thr Ile Lys Leu Val Lys Arg Ser Ile
    50                  55                  60

Glu Arg Leu Lys Glu Gln Asp Pro Ile Ser Gly Trp Phe Val His Leu
65                  70                  75                  80

Leu Ser Ile Thr Gly Cys Arg Gly Val Glu Met Gln Asn Val Lys Leu
                85                  90                  95

Thr Asp Ile Tyr Lys Glu Thr Ser Ser Asn Gly Glu Val Phe Tyr Ser
            100                 105                 110

Ile Arg Val Asn Val Ala Lys Lys Arg Ser Asn Ile Cys Ile Arg Glu
        115                 120                 125

Val Val Ile Ser Lys Leu Glu Phe Asp Ser Ile Met Arg Ala His Gln
    130                 135                 140

Glu Tyr Phe Asn Ser Arg Asp Lys Asp Ser Arg Arg Thr Tyr Leu Phe
145                 150                 155                 160

Gln Lys Ser Lys Leu Lys Phe Arg Asp Asn Lys Ile Asn Ile Thr Glu
```

```
                165                 170                 175

Ile Ser Lys Gln Phe Lys Glu Leu Leu Ile Lys Gly Gly Phe Lys His
            180                 185                 190

Arg Lys Ser Leu His Ile Leu Arg Asn Ile Phe Ile Ala Ser Leu Lys
        195                 200                 205

Ala Lys Gly Tyr Asn Ser Phe Glu Ile Lys Glu Leu Met Lys Tyr Ser
    210                 215                 220

Ser Thr Ser Glu Ile Asp Asn Val Tyr Gly Leu Ser Ser Ala Ser Lys
225                 230                 235                 240

Ile Gln Ala Tyr Lys Asp Ile Lys Thr Ser Leu Lys
                245                 250


<210> SEQ ID NO 111
<211> LENGTH: 29
<212> TYPE: DNA
<213> ORGANISM: Borrelia hermsii

<400> SEQUENCE: 111

aggcaccaat agcatattta gatcctgca                                         29


<210> SEQ ID NO 112
<211> LENGTH: 20
<212> TYPE: DNA
<213> ORGANISM: Borrelia hermsii

<400> SEQUENCE: 112

ggagaatggg ttgcgtcata                                                   20


<210> SEQ ID NO 113
<211> LENGTH: 23
<212> TYPE: DNA
<213> ORGANISM: Borrelia hermsii

<400> SEQUENCE: 113

gcgcagtatt atcacctcca ata                                               23


<210> SEQ ID NO 114
<211> LENGTH: 26
<212> TYPE: DNA
<213> ORGANISM: Borrelia miyamotoi

<400> SEQUENCE: 114

agtgcacttt gtgtgcttga aatggt                                            26


<210> SEQ ID NO 115
<211> LENGTH: 22
<212> TYPE: DNA
<213> ORGANISM: Borrelia miyamotoi

<400> SEQUENCE: 115

agcctaccta gatcctgctt at                                                22


<210> SEQ ID NO 116
<211> LENGTH: 20
<212> TYPE: DNA
<213> ORGANISM: Borrelia miyamotoi

<400> SEQUENCE: 116

gggtcacttg ctggtagttt                                                   20


<210> SEQ ID NO 117
```

-continued

```
<211> LENGTH: 23
<212> TYPE: DNA
<213> ORGANISM: Borrelia miyamotoi

<400> SEQUENCE: 117

acgcttcaga ggctctaatt ctg                                              23


<210> SEQ ID NO 118
<211> LENGTH: 19
<212> TYPE: DNA
<213> ORGANISM: Borrelia miyamotoi

<400> SEQUENCE: 118

gtggagataa ggcaagtga                                                   19


<210> SEQ ID NO 119
<211> LENGTH: 22
<212> TYPE: DNA
<213> ORGANISM: Borrelia miyamotoi

<400> SEQUENCE: 119

ctttatgaag agtagttgct tc                                               22
```

PHAGE-BASED DETECTION OF BORRELIOSIS AND MEANS THEREFOR

FIELD OF THE INVENTION

This invention relates to methods of detecting *Borrelia burgdorferi* sensu lato or for detecting *Borrelia* associated with Relapsing Fever (RF), kits for carrying out such methods, and methods of treating *Borrelia burgdorferi* sensu lato or RF infections in a subject. Uses of phage specific for *Borrelia* are also provided.

BACKGROUND

*Borrelia burgdorferi* sensu lato (s.l.) is a group of bacterial species of the *Borrelia* genus of the spirochete phylum, and that are known to be the causative agent in Lyme Disease (LD). Among them, three main species that are commonly found in Lyme patients in Europe are *B. burgdorferi* sensu stricto (s.s.), *B. afzelii*, and *B. garinii*. While *B. burgdorferi* s.s. causes LD both in the USA and in Europe. The other less commonly encountered LD species include *Borrelia spielmanii, Borrelia valaisiana, Borrelia bissettii, Borrelia lusitaniae, Borrelia finlandensis, Borrelia bavariensis, Borrelia japonica, Borrelia sinica, Borrelia spielmanii, Borrelia tanukii, Borrelia turdi, Borrelia* Yangtze, *Borrelia mayonii, Borrelia carolinensis, Borrelia andersonii, Borrelia lonestari*, and *Borrelia Americana.*

Bacteria that cause LD are spread to humans through the bite of bacterially infected ticks (and less frequently through other insects). It is the most commonly reported tick-born disease in the United States, and Centres for Disease Control and Prevention (CDC) records approximately 30 000 confirmed cases of LD annually. However, the number of suspected *Borrelia* infection is around 300 000 every year according to CDC. In Europe, the number of LD cases has increased steadily over the last two decades, with an estimation of about 85 000 cases every year. In England and Wales, it is estimated that around 3,000 new cases of LD are diagnosed each year.

Clinical diagnosis of LD is often problematic because the symptoms of LD are easily confused with other diseases. The manifestations of infection can range from a distinctive rash, tiredness, muscle pain, headaches, to severe arthritic, neurologic and cardiac conditions. Consequently, lab-based determination of *Borrelia* infection plays a vital role in LD diagnosis. Current lab-based diagnostic methods focus on indirectly determining the presence or absence of the bacteria in the body of the patient based on the human immune response to that bacterium. The current method of direct detection of *Borrelia* presence in patient suffers from low sensitivity, and therefore is regarded as of no diagnostic value.

A first problem associated with all known methodologies is as a result of the fact that the bacteria are only easily accessible from blood samples during the early stages of infection. In later stages of infection, the bacteria tend to migrate to the nervous system, where they can remain sequestered and so difficult to locate and identify with conventional diagnostic tools. Consequently, identification of infection in the later stages by attempting to detect the presence of the bacteria often has to involve the analysis of cerebrospinal fluid or the like, rather than the simpler analysis of blood samples.

The current "gold standard" technique for identifying presence of the bacteria involves growing a suspended bacterial culture from a sample from an individual suspected of contracting Lyme disease, and later characterising the bacteria in that culture. Often the characterisation is based on microscopy evaluation of morphological features of the bacteria. However, growing cultures takes up to 7 weeks before a sufficiently large and developed cultured population has been obtained from which to confirm the presence of the bacteria. Even then, such tests may not enable differentiation between Lyme disease and other tick-borne bacterial infections. For example, the bacteria associated with Relapsing Fever (RF) are morphologically similar to the bacteria that cause LD. LD and RF also have overlapping clinical symptoms. Consequently, a patient may be diagnosed as suffering from LD by this method, when in fact they suffer from RF; this being a problem as treatment methodologies may differ for each disease.

A second diagnostic methodology involves antibody based procedures. Antibodies (i.e. diagnostic antibodies) specific for the infected host's own antibodies that are raised as part of the immune response within the host to the infection (i.e. immune response antibodies) are used to detect the presence or absence of the infection. Unfortunately, however, such antibody based methodologies have only a short window of opportunity to accurately identify the presence of the infection. During the early stage of LD (2-3 weeks post infection), the antibody response in the host as part of their own immune reaction to infection is not normally sufficiently developed to be clearly detected by the diagnostic antibodies. In later stage LD, the production of immune response antibodies is suppressed by the bacteria, and so again the antibody signal may be too weak to be detected with a reasonable degree of accuracy. Consequently, antibody-based diagnostic methods are estimated to falsely identify 54% of patients as un-infected.

The third known diagnostic method involves the PCR-based detection of the bacteria. Due to the often extremely low concentration of the relevant bacteria in a patient's sample, such methods have a poor level of sensitivity. It has been calculated that only one third of patients suffering from LD in the USA showed a positive PCR result when their Cerebrospinal fluid samples were tested. Half of patients in the early stage of LD showed a negative PCR-derived result for the presence of the bacteria in blood samples.

As an example of current difficulties with diagnosing and treating LD, the veterinary profession report that tests used by them and based on the use of diagnostic antibodies commonly provides large number of false positive results for *Borrelia burgdorferi* sensu lato infection in horses. As a result, it is generally accepted that a large number of horses are needlessly treated with antibiotics such as oxytetracyline.

Consequently, there is a need for alternative methods of detecting the presence of *Borrelia burgdorferi* s.l., the causative agent of LD. Because of the similar difficulties faced with diagnosing relapsing fever (RF) which is also caused by *Borrelia* species and is often wrongly diagnosed as LD and vice versa, there is also a need for alternative methods of detecting the presence of *Borrelia* which are the causative agents of Relapsing Fever (herein referred to as Relapsing Fever *Borrelia* (RF *Borrelia*) such as *Borrelia miyamotoi* and *Borrelia hermsii.*

SUMMARY OF THE INVENTION

Bacteriophages (or phages) are viruses that can infect and multiply in a bacterium. Commonly they consist of a core of nucleic acid enclosed within a protein coat (i.e. the capsid). Phage that infect *Borrelia burgdorferi* s.l. and RF *Borrelia* are very poorly understood. The lack of research effort/output concerning *Borrelia* phages is mainly due to the following two hurdles. Firstly, growing *Borrelia* strains in vitro needs a complicated medium to mimic their in vivo conditions. This coupled with the demand for highly skilled, 'purpose-trained' scientists, who need to possess a good level of specialist knowledge concerning both *Borrelia* and phages, means that the academic output concerning *Borrelia* phages has been inhibited. Secondly, the commonly used phage characterisation methods, such as plaque assays, can't be simply translated into a *Borrelia* phage study because *Borrelia* have not previously been observed to grow on a solid agar surface to form a confluent cell growth on which phages could be observed. The inventors consider that they are the first to consistently grow viable lawns of *Borrelia*, on which a study of *Borrelia* phage can be conducted.

For an agent to be suitable for use in detecting the presence or absence of a bacterial infection, the agent should be capable of specifically identifying the bacteria associated with the infection. Advantageously, that agent should also be able to detect the bacterial infection in the least invasive manner possible. Phage have to-date not been suggested as useful in identifying the presence or absence of *B burgdorferi* s.l. infection. Even if they had, due to the limited understanding of phage that are known to infect *B. burgdorferi* s.l, there has been insufficient information to determine if phage could be used in such a diagnostic method. The art has continued to develop all relevant diagnostics by directing methodologies to the direct identification of the bacteria, or identification of immune response antibodies directly raised against the bacteria.

However, after extensive experimentation, it has surprisingly been found by the inventors that phage can be found that are specific to their *B. burgdorferi* s.l. or Relapsing Fever *Borrelia* host. As a result, successful methodologies have been provided for identifying infection of such bacteria and based on identifying the presence or absence of such phage.

Relapsing Fever *Borrelia* are any *Borrelia* species which are the causative agents of Relapsing Fever, for example, *Borrelia miyamotoi, Borrelia hermsii, Borrelia recurrentis, Borrelia crocidurae, Borrelia duttoni, Borrelia hispanica, Borrelia parkeri* and *Borrelia turicatae* or any combination thereof.

Therefore, in a first aspect of the present invention, there is provided a method of determining the presence or the absence of *B. burgdorferi* s.l. or RF *Borrelia* in a sample, the method comprising the steps of:— a) detecting the presence or absence of a phage specific for *B. burgdorferi* s.l or RF *Borrelia* in the sample; and
b) determining the presence of *B. burgdorferi* s.l. or RF *Borrelia* in the sample on the basis of the detection of the phage, or the absence of *B. burgdorferi* s.l. or RF *Borrelia* in the sample on the basis of the lack of detection of the phage.

The inventors have surprisingly found that *B burgdorferi* s.l. and RF *Borrelia* even those in sequestered states, dispense large numbers of phage. Consequently, for example, even when the bacteria are sequestered and so difficult to detect with little or no bacteria to be found in the blood, a blood sample from an infected subject does contain large numbers of phage or phage fragments originating from the bacteria. Consequently, a particularly advantageous aspect of the present invention is that the methods of the present invention can be practiced on a non-neuronal sample such as blood sample (e.g. whole blood, serum, plasma), urine sample, faecal sample, skin sample, lymph sample, or combinations thereof and still provide useful conclusions on the presence of absence of bacterial infection irrespective of the stage of infection; something that is not possible with known diagnostic methodologies.

Phage Specific for *Borrelia burgdorferi* Sensu Lato or RF *Borrelia*

The inventors have found that phylogenetic analysis of for example the terminase genes of the phage revealed a tight correlation between the terminase gene sequences and the identity of *Borrelia* species (FIG. 1). An independent subgroup of *Borrelia* species causing LD was well-separated from other *Borrelia* strains with statistically significant boot strap values. This demonstrated that the terminase genes were good molecular markers in identifying Lyme *Borrelia* strains. This is also the case for RF *Borrelia* as shown in FIG. 1. For example, with the tests provided herein, it is possible to distinguish between *Borrelia* which cause Lyme disease (*B. burgdorferi* s.l.) and RF *Borrelia.*

The same analysis has been carried out for other phage genes. For example, holins and endolysins. Phylogentic analyses based on holins (FIG. 2) endolysins (FIG. 3), integrase (FIG. 4) and portal proteins (FIG. 5) also show the potential of these genes in detecting *Borrelia* species.

Specificity can therefore be defined as a method which distinguishes between the phage of *B. burgdorferi* s.l. and the phage from other *Borrelia* species. For example, a nucleotide primer or antibody which binds preferentially to the phage of *B. burgdorferi* sensu lato; or does not cross-react with a nucleotide sequence or amino acid sequence from another *Borrelia* species. The method also may distinguish between the phage of RF *Borrelia* and the phage from other species.

Phage

A bacteriophage, also commonly called a phage, is a virus which infects and replicates within a bacterium. The phages described herein can be pro-phages, temperate/lysogenic phages, phage-like particles (such as plasmids) or lytic phages.

A prophage/temperate/lysogenic phage is a bacteriophage particle made of either double or single strand DNA or RNA. Phage genomes can be inserted and integrated into the circular bacterial DNA chromosome or existing as an extra-chromosomal plasmid. This is a latent form of a phage, in which the viral genes are present in the bacterium without causing disruption of the bacterial cell and sometimes may provide competitive advantage to the overall fitness of the bacterial host.

A lytic or virulent phage contains viral DNA/RNA which exists separately from the host bacterial DNA and replicates separately from the host bacterial DNA. Lytic phage are released upon destruction of the infected cell and its membrane.

Sample

The sample may be derived from a number of origins. The sample may therefore comprise or consist of plasma, serum, whole blood, cerebrospinal fluid, urine, faecal matter, skin, brain tissue, glial cells, lymph, sweat or amniotic fluid, or any combination thereof.

A sample may therefore be one that is taken from the subject at any time after infection and consistently provide the correct determination of the presence of the infection. Most surprisingly, the sample may be obtained shortly after infection (i.e. early stage infection), or after the infection has been well developed and that bacteria have become sequestered (i.e. late stage infection). This demonstrates a technical advantage associated with the present invention over known methodologies. Early stage infection would generally be considered to be less than 2 or 3 weeks from infection. Late stage infection would generally be considered to occur when the infected subject begins to suffer from neurological disorders (i.e. brain fog), which can be from 6 months after infection.

The subject from which the sample may be obtained is any animal that suffers from LD or RF. For example, the subject may be human, equine, canine, feline, ovine, caprine, ticks, lice, or any combination thereof. The subject may therefore be human, insect or animal.

Detection of Phage

By detection is meant determining if an interaction between the phage and a detection molecule specific for *Borrelia burgdorferi* sensu lato or Relapsing Fever *Borrelia*, for example a primer or antibody specific for a phage nucleic acid or protein respectively, is present or absent. These methods may be carried out ex vivo or in vitro. Detection may also be in vivo, for example via a dye probe.

The detection molecule which specifically binds the phage specific for the Lyme or RF *Borrelia* may be tagged or labelled. For example, detection may include the use of an agent which is capable of detection (a label) using for example spectrophotometry, flow cytometry, or microscopy. Exemplary labels include radioactive isotopes (such as 3H, 14C, 15N, 35S, 90V, 99Tc, 111Ln, 125I, or 131I), fluorophores (such as fluorescein, fluorescein isothiocyanate, rhodamine or the like), chromophores, ligands, chemiluminescent agents, bioluminescent agents (such as luciferase, green fluorescent protein (GFP) or yellow fluorescent protein), enzymes that can produce a detectable reaction product (such as horseradish peroxidise, luciferase, alkaline phosphatase, beta-galactosidase) and combinations thereof.

Phages can also be labelled with any DNA dye, such as SYBR Green, SYBR Gold, EB. The next generation sequencing technologies, such as short-read sequencing technologies (e.g. 454, Illumina, SOLiD and Ion Torrent) and long-read sequencing technology (e.g. PacBio sequencing) can also be used in identifying phage via whole genome sequencing.

Detection of Phage Nucleic Acid

Detection of the phage may comprise detection of the phage gene or gene fragment.

The phage gene may be defined by a nucleic acid sequence for the region of a phage genome that is specific to a *B burgdorferi* s.l. host in the case of Lyme disease diagnosis (i.e. the nucleic acid sequence is, or is part of, a phage gene that is found in only the target host, e.g. *B. burgdorferi* s.l., or in a phage specific for such a host, or part thereof). Alternatively, the phage gene may be defined by a nucleic acid sequence for the region of a phage genome that is specific to a RF *Borrelia* host in the case of RF diagnosis (i.e. the nucleic acid sequence is, or is part of, a phage gene that is found in only the target host, e.g. RF *Borrelia* or in a phage specific for such a host, or part thereof).

The applicant has found that a suitable phage gene is the gene that encodes the holin, endolysin, integrase, capsid, portal or terminase protein, or combinations thereof.

The following describes nucleic acid sequences specific to *B. burgdorferi* s.l. phage.

For example, the phage gene may be the *B. burgdorferi* s.l. terminase gene, when this is the case the gene may be a nucleic acid according to the sequence of SEQ ID NO.s 1-10 or a gene capable of encoding a protein according to the sequence of SEQ ID NO.s 36-45. Optionally, the terminase gene may be a nucleic acid with a greater than or equal to 70-100% sequence homology with SEQ ID NO.s 1-10 or a gene capable of encoding a protein with a greater than 70-100% sequence homology with SEQ ID NO.s 36-45. For example, greater than or equal to 70, 75, 80, 85, 90 or 95, 96, 97, 98, 99 or 99.5% sequence homology with SEQ ID NO.s 1-10 or 46-45. With regards to homologous genes and proteins, preferably these retain the function of the terminase.

SEQ ID NO. 1

```
5'GTGAACTTATATCAAACAAAACTTTTTACAACACTACAAAAGGAATAC
AAAAATAAATATGGAGTTGATATATCACAATTTGTAAAGCTAACAAATTC
TTCAATTAATTTTGATAAGTTTGAAGAAGAACAGTTAACTTTAAAACAAA
AAAATGTGATAAAAAGCATTAAAAAGAATAATGAAAAGAAGATTATACTC
AGCGGAGGCATAGCTAGTGGCAAAACGTATCTTGCATGTTATCTTTTTCT
AAAAAGTTTAATTGAAATTAAAAAGTTATACTCTAGTGATACTAATAATT
TCATTATAGGGAATTCACAACGTTCAGTTGAAGTTAATGTTTTGGGGCAA
TTTGAAAAGCTATGTAAACTTCTTAAAATTCCTTATATTCCAAGACATAC
AAATAATTCATATATTCTGATTGATTCACTACGTATTAATCTATATGGAG
GAGATAAGGCAAGTGATTTTGAAAGATTTAGGGGAAGTAATTCGGCACTT
ATTTTTGTTAATGAGGCTACAACTTTACACAAGCAAACTTTAGAGGAAGT
CTTAAAAAGACTAAGATGCGGGCAAGAAACTATTATTTTTGATACTAATC
CTGATCATCCAGAACACTATTTTAAAACCGATTATATTGATAATATAGCG
ACCTTTAAGACATATAAGTTTACAACTTATGATAATGTGCTACTTAGTAA
AGGATTTGTCGAAACACAAGAAAAGCTATATAAAGATATACCATCATATA
AAGCAAGAGTTTTGTTAGGTGAGTGGATAGCAAGCACTGATTCAATTTTT
ACACAAATAAATATTACTGATGATTATGTATTTACTAGCCCGATAGCATA
TTTAGACCCAGCATTTAGTGTTGGCGGGGATAACACTGCATTATGTGTTA
TGGAGCGAGTTGATGATAAGTATTATGCTTTTGTATTTCAAGACCAAAGA
CCAGCTAATGATCCTTATATTATGAATATGGTAAAGACTGTTATAGAAAA
TTTCAATGTGCATACACTGTATTTAGAGGATAGAGATAATACAAAAGGTG
CTGGTGGATTGACCCGTGAATACATCTTGCTAAGAAGTAATATAAGCCAA
TATTTTAGAATTGTTCCAGTTAAGCCAAAGTCTAATAAATTTAGCAGAAT
AACAACGTTAATTACGCCGTTTACTTACAAAAAACTTTATATTACAAAGT
ACAGTAGTTCTTCCGTATTTAATGATATTTATTCGTATAAGGGGGATAAT
AAAACCCATGATGACGCTCTTGATGCAATATCTGCAGCATATTTGATGTT
GTCTTTAGGATATAGAGAGCGAAGTGTTCACTTTGGCAATCAAAGATTTT
TGTAA3'.
```

Alternatively or additionally, the phage gene may be the holin (SEQ ID NO.s 17-25), endolysin (SEQ ID NO.s 26-34), integrase (SEQ ID NO.16), capsid and/or portal (SEQ ID NO. 11-15) gene(s). Alternatively, the phage gene may be a gene capable of encoding a holin protein according to the sequence of SEQ ID NO.s 52-60 or an endolysin protein (SEQ ID NO.s 61-69) or an integrase protein (SEQ ID NO 51) or a capsid and/or portal protein (SEQ ID NO.s 46-50). Optionally, the gene detected may be a nucleic acid with a greater than 70-100% sequence homology with any of SEQ ID NO.s 11-34) or a gene capable of encoding a protein with a greater than 70-100% sequence homology with SEQ ID NO.s 36-69. For example, greater than or equal to 70, 75, 80, 85, 90 or 95, 96, 97, 98, 99 or 99.5% sequence homology with SEQ ID NO.s 11-34 or 36-69. With regards to homologous genes and proteins, preferably these retain the function of the holin, portal, endolysin, integrase or capsid protein.

Instead of percentage sequence homology, a homologue of the phage gene may alternatively be defined as one with addition, substitution and/or deletion of 1, 2, 3, 4, 5, 6, 7, 8, 9, 10, 11, 12, 13, 14, 15, 16, 17, 18, 19, 20, 21, 22, 23, 24, 25, 30, 40 or 50 contiguous or non-contiguous nucleotides, preferably whilst retaining function of the protein encoded by the gene, the addition, substitution and deletion being relative to the unmodified sequence of SEQ ID NO.s 1-34.

Detection may also involve detection of a fragment of any of the holin, endolysin, integrase, portal, capsid or terminase protein, or combinations thereof. For example, detection of a 50-1300 base pair fragment. For example, 50, 100, 150, 200, 250, 300, 350, 400, 450, 500, 550, 600, 650, 700, 750, 800, 850, 900, 950, 1000, 1050, 1100, 1150, 1200, 1250 or 1300 contiguous base pairs or any range of base pairs based on these values. Optionally, the gene fragment to be detected may be a nucleic acid with equal to or greater than 70-100% sequence homology with any fragment of SEQ ID NO.s 1-34. For example, equal to or greater than 70, 75, 80, 85, 90 or 95, 96, 97, 98, 99 or 99.5% sequence homology with any fragment of SEQ ID NO.s 1-34, preferably whilst retaining function of the protein encoded by the gene.

For example, a fragment of the terminase gene detected may be: GAGTGGATAGCAAGCACTGATTCAATTTTTACACAAATAAATATTACTGATGATT ATGTATTTACTAGCCCGATAGCATATTTAGACCCAGCATTTAGTGTTGGCGGGG ATAACACTGCATTATGTGTTATGGAGCGAGTTGATGAT (SEQ ID NO. 35) or any sequence with equal to or greater than 70-100% sequence homology with SEQ ID NO. 35). For example, equal to or greater than 70, 75, 80, 85, 90 or 95, 96, 97, 98, 99 or 99.5% sequence homology with SEQ ID NO. 35.

The following describes nucleic acid sequences specific to RF *Borrelia* phage.

The phage gene may be the RF *Borrelia* terminase gene, when this is the case the gene may be a nucleic acid according to the sequence of SEQ ID NO.s 84 or 86 or a gene capable of encoding a protein according to the sequence of SEQ ID NO.s 85 or 87. Optionally, the terminase gene may be a nucleic acid with equal to or greater than 70-100% sequence homology with SEQ ID NO.s 84 or 86; or a gene capable of encoding a protein with equal to or greater than 70-100% sequence homology with SEQ ID NO.s 85 or 87. For example, equal to or greater than 70, 75, 80, 85, 90 or 95, 96, 97, 98, 99 or 99.5% sequence homology with SEQ ID NO.s 84 or 86, preferably whilst retaining function of the terminase protein encoded by the gene.

Alternatively or additionally, the phage gene may be the holin (SEQ ID NO.s 97-100), endolysin (SEQ ID NO. 101), integrase (SEQ ID NO.103), capsid and/or portal (SEQ ID NO.s 102) gene(s). Alternatively, the phage gene may be a gene capable of encoding a holin protein according to the sequence of SEQ ID NO.s 104-107 or an endolysin protein (SEQ ID NO. 108) or an integrase protein (SEQ ID NO. 110) or a capsid and/or portal protein (SEQ ID NO. 109). Optionally, the gene detected may be a nucleic acid with a greater than 70-100% sequence homology with any of SEQ ID NO.s 97-103) or a gene capable of encoding a protein with a greater than 70-100% sequence homology with SEQ ID NO.s 104-110. For example, greater than or equal to 70, 75, 80, 85, 90 or 95, 96, 97, 98, 99 or 99.5% sequence homology with SEQ ID NO.s 97-103 or 104-110. With regards to homologous genes and proteins, preferably these retain the function of the holin, portal, endolysin, integrase or capsid protein.

Instead of percentage sequence homology, a homologue of the phage gene may alternatively be defined as one with addition, substitution and/or deletion of 1, 2, 3, 4, 5, 6, 7, 8, 9, 10, 11, 12, 13, 14, 15, 16, 17, 18, 19, 20, 21, 22, 23, 24, 25, 30, 40 or 50 contiguous or non-contiguous nucleotides, preferably whilst retaining function of the protein encoded by the gene, the addition, substitution and deletion being relative to the unmodified sequence of SEQ ID NO.s 84, 86 or 97-103.

Detection may also involve detection of a fragment of any of the holin, endolysin, integrase, portal, capsid or terminase protein, or combinations thereof. For example, detection of a 50-1300 base pair fragment. For example, 50, 100, 150, 200, 250, 300, 350, 400, 450, 500, 550, 600, 650, 700, 750, 800, 850, 900, 950, 1000, 1050, 1100, 1150, 1200, 1250 or 1300 contiguous base pairs or any range of base pairs based on these values. Optionally, the gene fragment to be detected may be a nucleic acid with equal to or greater than 70-100% sequence homology with any fragment of SEQ ID NO.s 84, 86 or 97-103. For example, equal to or greater than 70, 75, 80, 85, 90 or 95, 96, 97, 98, 99 or 99.5% sequence homology with any fragment of SEQ ID NO.s 84, 86 or 97-103, preferably whilst retaining function of the protein encoded by the gene.

The following description applies to the detection of the entire phage gene or a gene fragment for a phage specific for *B. burgdorferi* s.l. or RF *Borrelia.*

Isolation of the Nucleic Acid from a Sample

In order to assist molecular biological tools to practice the step of detecting, step a) may be preceded by the step of isolating nucleic acid from the sample, and step a is practiced on the isolated nucleic acid. Any method available to the skilled person that is capable of isolating nucleic acid from the sample would be appropriate for use in the present application. Not wishing to be restricted further, but in the interest of clarity, isolation of the nucleic acid from the sample may be performed using phenol chloroform extraction and isopropanol precipitation, or using membrane based nucleic acid isolation kits (such as QIAGEN® kits; QIAAmp DNA stool mini Kit®).

The inventors have devised an efficient method for isolation of nucleic acid from a sample containing *Borrelia*. Therefore, also provided is a method of extracting phage DNA from *Borrelia*, the method comprising: a) incubating the *Borrelia* in ammonium hydroxide; and b) adding phenol-chloroform to the *Borrelia* and ammonium hydroxide mixture.

The method may further comprise centrifugation to remove bacterial debris. The resulting supernatant following removal of the bacterial debris may be mixed with sodium acetate. Isopropanol may then be added to the supernatant and sodim acetate mixture. A further step of centrifugation may then be carried out to precipitate the phage DNA The same volume of phenol-chloroform may be used as the volume of ammonium hydroxide.

Part a) may be carried out at a temperature of 50-150° C. For example, 70-130° C., 80-120° C. or 90-110° C.

The ammonium hydroxide concentration may be 0.5-1M. For example, 0.6M, 0.7M, 0.8M, 0.9M.

Further exemplary details are provided in the examples section under the heading "PCR and sequencing".

Detection of the Nucleic Acid

Any method known to the skilled person and capable of detecting the presence or absence of a gene (optionally in an isolated nucleic acid) may be suitable for use in step a) of the presently claimed invention. As the phage gene may be present in relatively low copy number, in order to make detection easier, in one embodiment of the present invention the method of detecting involves subjecting the isolated nucleic acid to amplification of the phage gene, e.g. by real time polymerase chain reaction (q PC R).

Alternatively or additionally detection of the phage gene may be confirmed by nucleic acid sequence analysis, by detection of labelled nucleotides inserted in the amplified product, or by detection of hybridisation of probe that is specific to the phage gene (hybridisation being detected, for example, by use of labelled probes).

Apart from Taqman-based qPCR platform, other methods of nucleic acid detection that can be used include SYBR green-based real time PCR assay, digital PCR which involves splitting the same qPCR mix into a large number of individual wells. The endpoint PCR products are determined using Poisson statistical analysis according to the presence (scored as '1') and absence (scored as '0') of fluorescent signal in each well. Other possible methods include Loop mediated isothermal amplification (LAMP), an isothermal nucleic acid amplification technique that does not require a thermal cycler. LAMP could be employed to target terminase, holin, endolysin, integrase, capsid, and portal proteins; and DNA hybridisation based methods such as Fluorescence in situ hybridisation (FISH), which works by performing a DNA/DNA hybridisation using fluorescently labelled short DNA strands (the phage genes) as probes to hybridise to its complementary parts on genomic DNA.

Detection may include the use of an agent which is capable of detection (a label) using for example spectrophotometry, flow cytometry, or microscopy. Exemplary labels include radioactive isotopes (such as 3H, 14C, 15N, 35S, 90V, 99Tc, 111Ln, 125I, or 131I), fluorophores (such as fluorescein, fluorescein isothiocyanate, rhodamine or the like), chromophores, ligands, chemiluminescent agents, bioluminescent agents (such as luciferase, green fluorescent protein (GFP) or yellow fluorescent protein), enzymes that can produce a detectable reaction product (such as horseradish peroxidise, luciferase, alkaline phosphatase, betagalactosidase) and combinations thereof.

The following relates to primers specific for B. *Burgdorferi* s.l. phage.

The step of amplification may involve the use of a forward primer selected from the group consisting of nucleic acids comprising or consisting of SEQ ID NO 70:

```
5'GTGAACTTATATCAAAC3'
```

Alternatively, or additionally, the step of amplification involves the use of a reverse primer selected from the group consisting of nucleic acids comprising or consisting of SEQ ID NO. 71:

```
5'ATAATCTTCTTTTCATT3'
```

Alternatively or additionally, the step of amplification may involve the use of any one or more of the primers of SEQ ID NO.s 73-77 and/or 79-83.

Where identification of the phage gene is achieved by the use of hybridisation probes, suitable probes could be any capable of specifically binding to the phage gene, or portion thereof. For example, appropriate probes may be any one or more of the aforementioned primers comprising or consisting of SEQ ID NO.s 70-77 and/or 79-83, or nucleic acids comprising or consisting of SEQ ID NO.s 1-34 or fragment thereof, any homologue thereof, or specifically binding portions thereof, or any combination thereof.

The following relates to primers specific for RF *Borrelia* phage.

The step of amplification may involve the use of any of primers comprising or consisting of SEQ ID NO.s 88-96, any homologue thereof, or specifically binding portions thereof, or any combination thereof.

Where identification of the phage gene is achieved by the use of hybridisation probes, suitable probes could be any capable of specifically binding to the phage gene, or portion thereof. For example, appropriate probes may be any one or more of the aforementioned primers comprising or consisting of SEQ ID NO.s 88-96, or nucleic acids comprising or consisting of SEQ ID NO.s 84, 86 and/or 97-103 or fragment thereof, any homologue or thereof, or specifically binding portions thereof, or any combination thereof.

Detection may also comprise detection of a phage RNA or RNA fragment. For example, an RNA fragment of 50, 100, 150, 200, 250, 300, 350, 400, 450, 500, 550, 600, 650, 700, 750, 800, 850, 900, 950, 1000, 1050, 1100, 1150, 1200, 1250 or 1300 base pairs or any range of base pairs based on these values.

For example, presence of the phage gene may also be detected by detection of the corresponding mRNA. This can be achieved by performing a reverse transcriptase real time PCR by performing a real time PCR against cDNA synthesised from total RNA. For example, by hybridisation of primers to mRNA. The methodology used in PCR methods, for example RT-PCR, will be well known to those skilled in the art.

Apart from PCR, there are probe-based methods such as Northern blotting, in situ hybridisation. There are also RNA sequencing method that can be used in detecting phage RNA via sequencing the total RNA.

Some methods may require the isolation of RNA from a sample. Such isolation techniques are known in the art and may utilise commercially available RNA isolation kits from manufacturers such as Qiagen or Maxwell viral total nucleic acid purification kit from Promega or the isolation methods described above with regards to gene sequence detection.

Detection of Phage Proteins

Detection may also comprise detection of a phage protein or protein fragment.

Other ways of detecting the *Borrelia* phage include detection of the phage specific proteins.

In the case of LD, the phage protein is one specific to a *B burgdorferi* s.l. host (i.e. the amino acid sequence is found in only the target host, e.g. *B. burgdorferi* s.l., or in a phage specific for such a host, or part thereof).

Suitable proteins for LD detection include holin (SEQ ID NO.s 52-60), endolysin (SEQ ID NO. 61-69), integrase (SEQ ID NO. 51), portal (SEQ ID NO. 46-50), capsid and/or terminase (SEQ ID NO.s 36-45).

Optionally, the amino acid sequence detected may have equal to or greater than 70-100% sequence homology with SEQ ID NO.s 36-69 or may be encoded by a gene having equal to or greater than 70-100% sequence homology with SEQ ID NO.s 1-34. For example, equal to or greater than 70, 75, 80, 85, 90 or 95, 96, 97, 98, 99 or 99.5% sequence homology with SEQ ID NO.s 36-69 or 1-34. With regards to homologous genes and proteins, preferably these retain the function of the holin, portal, endolysin, integrase or capsid protein.

In the case of RF, the phage protein is one specific to a RF *Borrelia* host (i.e. the amino acid sequence is found in only the target host, e.g. RF *Borrelia* or in a phage specific for such a host, or part thereof).

Suitable proteins for RF detection include terminase (SEQ ID NO.s 85 or 87), holin (SEQ ID NO.s 104-107), endolysin (SEQ ID NO. 108), portal protein (SEQ ID NO. 109) and/or integrase (SEQ ID NO. 110).

Optionally, the amino acid sequence detected may have equal to or greater than 70-100% sequence homology with SEQ ID NO.s 85, 87 or 104-110 or may be encoded by a gene having equal to or greater than 70-100% sequence homology with SEQ ID NO.s 84, 86 or 97-103. For example, equal to or greater than 70, 75, 80, 85, 90 or 95, 96, 97, 98, 99 or 99.5% sequence homology with SEQ ID NO.s 84-87 or 97-110. With regards to homologous genes and proteins, preferably these retain the function of the holin, portal, endolysin, integrase or capsid protein.

Instead of percentage sequence homology, a homologue may be defined as a protein with addition, substitution and/or deletion of 1, 2, 3, 4, 5, 6, 7, 8, 9, 10, 11, 12, 13, 14, 15, 16, 17, 18, 19, 20, 21, 22, 23, 24, 25, 30, 40 or 50 contiguous or non-contiguous amino acids, preferably whilst retaining function of the protein, the addition, substitution and deletion being relative to the unmodified sequence of SEQ ID NO.s 85, 87 or 104-100.

Detection may also involve detection of a fragment of any of the holin, endolysin, integrase, portal, capsid or terminase proteins, or combinations thereof. For example, detection of an epitope on any of these proteins by an antibody specific for *Borrelia burgdorferi* sensu lato. The epitope may be a linear epitope. For example, a fragment may comprise a stretch of amino acid residues of at least 5 to 10 contiguous amino acids, 10 to 15 contiguous amino acids, 15 to 20 contiguous amino acids, or 20 to 30 or more contiguous amino acids. Or the epitope may be a non-contiguous epitope specific to the phage protein. For example, a non-contiguous epitope comprising 5, 10, 15 or 20 amino acids.

Optionally, the protein fragment to be detected may be an amino acid with equal to or greater than 70-100% sequence homology with any fragment of SEQ ID NO.s 36-69, 85, 87 or 104-110). For example, equal to or greater than 70, 75, 80, 85, 90 or 95, 96, 97, 98, 99 or 99.5% sequence homology with any fragment of SEQ ID NO.s 36-69, 85, 87 or 104-110 whilst retaining the function of the protein.

Protein specific detection can be carried out by any method known in the art. For example, Immunohistochemistry (IHC) can be used to detect protein expression. Western blotting and ELISA are also methods useful for detecting protein expression and secretion. Antibodies or other proteins or molecules capable of selective binding to the phage proteins can be used for detection. Protein can also be detected by MALDI-TOF mass spectrometry. Protein sequencing, for example by mass spectrometry or Edman degradation, can also be used for detection. Linear fragments of 10, 20, 30, 40, 50, 60, 70, 80, 90, 100, 110, 120, 130, 140, 150, 160, 170, 180, 190, 200, 300, 400, 500 amino acids or any range of these numbers may be sequenced.

Phage protein can be detected using a primary antibody with binding specificity for the phage protein. The primary antibody can be labelled with a detectable moiety or can be conjugated to a hapten (such as biotin or the like) wherein the hapten is detectable by a detectably labelled cognate hapten binding molecule, for example streptavidin horseradish peroxidase. Alternatively, a secondary antibody can be used which specifically binds the first primary antibody and instead this secondary antibody may be detectable as described above for the primary antibody.

The binding specificity of phage antibodies (antibodies with binding specificity to a phage protein) can be established using, for example, Western blotting.

The term antibody refers to an immunoglobulin molecule or combinations thereof that specifically binds to or is immunologically reactive with a particular antigen and includes polyclonal, monoclonal, genetically engineered and otherwise modified forms of antibodies, not limited to chimeric antibodies, humanised antibodies, heteroconjugate antibodies (for example bispecific antibodies, diabodies, triabodies, and tetrabodies), single chain Fv antibodies (scFv), or polypeptides that contain at least a portion of immunoglobulin that is sufficient to confer specific antigen binding to the polypeptide. Antibody fragments include proteolytic antibody fragments such as F(ab')2 fragments, Fab' fragments, Fab'-SH fragments, Fab fragments, FV, rIgG, recombinant antibody fragments such as sFv fragments, dsFv fragments, bispecific sFv fragments, bispecific dsFv fragments, complementarity determining region (CDR) fragments, camelid antibodies and antibodies produced by cartilaginous and bony fishes and isolated binding domains thereof. A Fab fragment is a monvalent fragment consisting of the VL, VH, CL and CH1 domains; a F(ab')2 fragment is a bivalent fragment comprising two Fab fragments linked by a disulphide bridge at the hinge region, an Fd fragment consists of the VH and CH1 domains; an FV fragment consists of the VL and VH domains of a single arm of an antibody; and a dAb fragment consists of a VH domain. A single chain antibody (scFv) is an antibody in which a VL and VH region are paired to form a monovalent molecule via a synthetic linker that enables them to be made as a single protein chain. Diabodies are bivalent, bispecific antibodies in which the VH and VL domains are expressed on a single polypeptide chain, but using a linker that is too short to allow for pairing between the two domains on the same chain, thereby forcing the domains to pair with complementary domains of another chain and creating two antigen binding sites. A chimeric antibody is an antibody that contains one or more regions from one antibody and one or more regions from one or more other antibodies. An antibody may have one or more binding sites. If there is more than one binding site, the binding sites may be identical to one another or may be different. For instance, a naturally occurring immunoglobulin has two identical binding sites, a single chain antibody or Fab fragment has one binding site, while a bispecific or bifunctional antibody has two different binding sites.

Alternatively, other proteins which are capable of selective binding may also be used for detection.

For example, the phage protein may be detected using aptamers (for example a single stranded nucleic acid molecule (such as, DNA or RNA) that assumes a specific, sequence dependent shape and binds to the phage protein with high affinity and specificity), mirror image aptamers (SPIEGELMER™), engineered nonimmunuoglobulin binding proteins, for example nonimmunoglobulin binding proteins based on scaffolds including fibronectin (ADNECTINS™), CTLA-1 (EVIBODIES™), lipocalins (ANTICALINS™), protein A domain (AFFIBODIES™) or the like.

Homology

With regards to nucleic acid sequences, homology may be defined as to a nucleotide sequence which encodes a protein with a similar function. With regards to protein sequences, homology may be defined as to a protein with a similar function. For example, a protein with the same function from another *Borrelia burgdorferi* sensu lato or RF *Borrelia* species.

Percentage homology can be defined as the percentage of identical residues and the percentage of residues conserved with similar physiochemical properties. The degree of homology between sequences may be determined using any suitable method known in the art (See e.g., Smith and Waterman, Adv. Appl. Math., 2:482 [1981]; Needleman and Wunsch, J. Mol. Biol, 48:443 [1970]; Pearson and Lipman, Proc. Natl. Acad. Sci. USA 85:2444 [1988]; programs such as GAP, BESTFIT, FASTA, and TFASTA in the Wisconsin Genetics Software Package (Genetics Computer Group, Madison, Wis.); and Devereux et al., Nucl. Acid Res., 12:387-395 [1984]).

The above percentages of homology may equally apply to percentage sequence identity only. For example, the percentage of nucleic acid residues which are identical between the terminase nucleic acid sequence and another terminase sequence, which may for example, be from a different *Borrelia* species.

Instead of percentage sequence homology, a homologue of the phage gene may be defined as one with addition, substitution or deletion of 1, 2, 3, 4, 5, 6, 7, 8, 9, 10, 11, 12, 13, 14, 15, 16, 17, 18, 19, 20, 21, 22, 23, 24, 25, 30, 40 or 50 contiguous or non-contiguous nucleotides, preferably whilst retaining function of the protein encoded by the gene, the addition, substitution and deletion being relative to the unmodified sequence.

Sequences

In a further aspect of the present invention there is provided the phage genes, primers, nucleic acids and hybridising probes; and amino acid sequences as defined above.

For reference, a table of the various gene sequences isolated from various *B. burgdorferi* s.l. in the sequence listing is provided below along with the corresponding proteins.

| SEQ ID NO. | Description | Corresponding protein SEQ ID NO. |
|---|---|---|
| 1-10 | Terminase gene sequences | 36-45 |
| 11-15 | Portal gene sequences | 46-50 |
| 16 | Integrase gene sequence | 51 |
| 17-25 | Holin gene sequences | 52-60 |
| 26-34 | Endolysin gene sequences | 61-69 |
| 35 | Terminase 147bp fragment | |

The SEQ ID NO.s of the primers used for gene sequence detection are also provided:

| SEQ ID NO. | Description |
|---|---|
| 70 and 71 | Terminase Forward and Reverse Primers (these are primers for end-point, conventional, gel-based PCR) |
| 72 and 73 | Holin Forward and Reverse Primers |
| 74 and 75 | Endolysin Forward and Reverse Primers |
| 76 and 77 | Forward and Reverse Primers to amplify SEQ ID NO. 78 |
| 78 | Gene sequence of combined Holin and Endolysin |
| 79 | Forward primer for Terminase 147bp fragment |
| 80 | Reverse primer for Terminase 147bp fragment |
| 81 | Probe for Terminase 147bp fragment |
| 82 | forward primer for SEQ ID NO. 1 (terminase); 721bp fragment |
| 83 | reverse primer for SEQ ID NO. 1 (terminase); 721bp fragment |

Provided below is a table of the various gene sequences isolated from various *Borrelia* species in the sequence listing which are causative agents of RF:

| SEQ ID NO. | Description | Corresponding protein SEQ ID NO. |
|---|---|---|
| 84 | *Borrelia miyamotoi* terminase | 85 |
| 86 | *Borrelia hermsii* terminase | 87 |
| 97 | *Borrelia parkeri* holin | 104 |
| 98 | *Borrelia turicatae* holin | 105 |
| 99 | *Borrelia hermsii* holin | 106 |
| 100 | *Borrelia coriaceae* holin | 107 |
| 101 | *Borrelia hermsii* endolysin | 108 |
| 102 | *Borrelia turicatae* portal | 109 |
| 103 | *Borrelia turicatae* integrase | 110 |

The SEQ ID NO.s of the primers used for gene sequence detection are also provided:

| SEQ ID NO. | Description |
|---|---|
| 88 | *B. miyamotoi* terminase probe (120bp amplicon) |
| 89 and 90 | *B. miyamotoi* terminase forward and reverse primers (120bp amplicon) |
| 91 | *B. miyamotoi* terminase probe (87bp amplicon) |
| 92 and 93 | *B. miyamotoi* terminase forward and reverse primers (87bp amplicon) |
| 94 | *B. hermsii* terminase probe |
| 95 and 96 | *B. hermsii* forward and reverse primers (124bp amplicon) |

Homologues and fragments of these nucleic acid and protein sequences are also provided in accordance with the description above for the detection method.

Also provided are use of the above sequences, homologues and fragments as diagnostic markers for LD or RF.

Species Detection

The *Borrelia burgdorferi* sensu lato may be any that are the causative agent for LD.

For example any of *Borrelia afzelii, Borrelia spielmanii, Borrelia valaisiana, Borrelia Borrelia finlandensis, Borrelia bugdorferi* sensu strictu, *Borrelia bissettii, Borrelia bavariensis, Borrelia japonica, Borrelia lusitaniae, Borrelia sinica, Borrelia spielmanii, Borrelia tanukii, Borrelia turdi, Borrelia valaisiana, Borrelia* Yangtze, *Borrelia mayonii, Borrelia carolinensis, Borrelia andersonii, Borrelia lonestari*, and *Borrelia Americana* or any combination thereof. For example, it may be *Borrelia afzelii, Borrelia bugdorferi* sensu strict, *Borrelia garinii*, or any combination thereof. For example, it may be *Borrelia bugdorferi* sensu strictu, or any combination of *Borrelia bugdorferi* sensu strictu with any of the above.

The RF *Borrelia* may be any that are the causative agent for RF. For example, any of *Borrelia miyamotoi, Borrelia hermsii, Borrelia recurrentis, Borrelia crocidurae, Borrelia duttoni, Borrelia hispanica, Borrelia parkeri* and *Borrelia turicatae* or any combination thereof.

The inventors were surprised that when analysing *Borrelia burgdorferi* sensu lato species specific phage genes further, these genes not only showed specificity to *Borrelia burgdorferi* sensu lato, but also specifically to species within that group. The RF *Borrelia* specific phage genes were also found to be specific to particular species.

None of the known methods can distinguish between different species of *Borrelia*. This can be an important advantage as knowing what species of *Borrelia* is present can educate the treatment regimen and thereby optimise the success of treatment (as some species of *Borrelia* respond better to specific antibiotics than do others).

Consequently, the method may determine the presence or the absence of a species of *Borrelia burgdorferi* sensu lato or RF *Borrelia* in the sample, the method comprising the steps of:— a) detecting the presence or absence of the *Borrelia burgdorferi* sensu lato or RF *Borrelia* species specific phage gene in the sample;
b) determining the presence of the species of the *Borrelia burgdorferi* sensu lato or RF *Borrelia* in the sample on the basis of the detection of the species specific phage gene, or the absence of the species of *Borrelia burgdorferi* sensu lato or RF *Borrelia* in the sample on the basis of the lack of detection of the species specific phage gene.

In order to assist molecular biological tools to practice the step of detecting, step a) may be preceded by the step of isolating nucleic acid from the sample, and step a) is practiced on the isolated nucleic acid. Any method available to the skilled person that is capable of isolating nucleic acid from the sample would be appropriate for use in the present application. Not wishing to be restricted further, but in the interest of clarity, isolation of the nucleic acid from the sample may be performed using phenol chloroform extraction and isopropanol precipitation, or using membrane based nucleic acid isolation kits (such as QIAGEN® kits; QIAAmp DNA stool mini Kit®).

For example, when the bacteria is *Borrelia bugdorferi* sensu strictu the *Borrelia bugdorferi* sensu strictu specific phage gene may be any of those discussed above. For example, the gene may be a terminase gene (i.e. the phage gene), which can be that according to SEQ ID NO 1. Optionally the gene is a nucleic acid with equal to or greater than 70-99.5% sequence homology to any one of SEQ ID No. 1. The forward primer used to amplify the *Borrelia bugdorferi* sensu strictu specific terminase gene is a nucleic acid comprising or consisting of SEQ ID NO 70. The reverse primers may be a nucleic acid comprising or consisting of SEQ ID NO 71. Where identification of this gene is achieved by the use of hybridisation probes, suitable probes would be any of the aforementioned primers, nucleic acids comprising or consisting of SEQ ID NO 1-10 or 35, any homologue thereof, or specifically binding portions thereof, or any combination thereof.

For example, when the bacteria is *Borrelia miyamotoi*, the specific phage gene may be any of those discussed above. For example, the gene may be a terminase gene (i.e. the phage gene), which can be that according to SEQ ID NO 84. Optionally the gene is a nucleic acid with equal to or greater than 95, 96, 97, 98, 99 or 99.5% sequence homology to SEQ ID No. 84. The forward primer used to amplify the *Borrelia miyamotoi* specific terminase gene is a nucleic acid comprising or consisting of SEQ ID NO 89 or 92. The reverse primers may be a nucleic acid comprising or consisting of SEQ ID NO 90 or 93. Where identification of this gene is achieved by the use of hybridisation probes, suitable probes would be nucleic acids comprising or consisting of SEQ ID NO 84, or any primer comprising or consisting of SEQ ID NO.s 88-93; any homologue thereof, or specifically binding portions thereof, or any combination thereof.

Kit

In a further aspect of the present invention there is a kit for determining the presence or the absence of *Borrelia burgdorferi* sensu lato and or RF *Borrelia* in a sample, the kit may comprise one or more of the aforementioned primers for specifically hybridising with nucleic acid sequence of a *Borrelia* specific phage gene. The selection of the primer, or preferably primer pairs (i.e. forward and reversed primers) would be guided by the target *Borrelia burgdorferi* sensu lato or RF *Borrelia* species. The kit may further comprise hybridisation probes which may be the aforementioned primers, or any of the aforementioned probes. Again, the choice of probes would be selected on the basis of the target species to be identified by the kit. The choice of hybridisation probes for a kit for determining the presence of *Borrelia burgdorferi* sensu lato, or indeed a kit for identifying a specific species of such bacteria can be extrapolated from the details of appropriate hybridisation probes discussed above. As an alternative to nucleic acid probes, antibodies which bind to phage specific proteins may be included in a kit. Such antibodies are discussed above.

Monitoring the Progression of Infection

The method may be applied to monitoring the progression of an infection from *Borrelia burgdorferi* sensu lato or RF *Borrelia*; or a species of such bacteria based on the teachings of the earlier aspects of the present invention.

The terms used in this aspect of the present invention are the same as, and so refer back to, the terms used in earlier aspects of the present invention.

In a further aspect of the present invention there is provided a method of monitoring the progression of infection from *Borrelia burgdorferi* sensu lato or RF *Borrelia*. The method comprising steps of:— a) determining the amount of phage in a first sample obtained from the subject;
b) detecting the amount of phage in a second sample obtained from the subject at a second time point;
c) comparing the amount of phage in the first sample identified in step a) with that identified for the second sample in step b).

The method may include the step of isolating a first population of nucleic acid from a first sample obtained from the subject at a first time period, prior to step a). The method may include the step of isolating a second population of nucleic acid from a second sample obtained from the subject at a second time point, prior to step b).

Treatment

Detection of the presence of *Borrelia burgdorferi* sensu lato in a sample from a subject confirms a diagnosis that the subject has LD. Treatment for *Borrelia burgdorferi* sensu lato infection is the treatment of Lyme disease.

Detection of the presence of an RF *Borrelia* in a sample from a subject confirms a diagnosis that the subject has RF.

Any of the methods described may include the step of administering an antibiotic or more than one antibiotic. Such a method may be capable of determining the ability for the antibiotic to treat *Borrelia burgdorferi* sensu lato or RF infection, or species specific *Borrelia burgdorferi* sensu lato or RF infection.

The following relates to treatment of LD:

The recommended treatment for infection is a combined therapy comprising one, two, or sometimes three, antibiotics used at the same time. This may be in the form of sequential treatments or synchronously combined long-term antibiotic treatment. Antibiotics such as tetracyclines can be used for treatment alone or in combination with hydroxychloroquine. This may involve simultaneous administration of the antibiotics.

The main antibiotics recommended for use are: 1) pencillins; 2) cephalosporins; 3) macrolides; 4) fluroquinolones and/or 5) cyclines.

Any of the above antibiotics may be combined or used sequentially.

As an example, cephalosporins can be used alone or in combination with minocycline. This treatment may involve alternating between the two antibiotics. Doxycycline and/or minocycline can be combined with azithromycin and/or hydroxychloroquine. Other combinations based on the above classes of antibiotics or other antibiotics are possible.

The terms used in this aspect of the present invention are the same, and so refer back to the same terms used in earlier aspects of the present invention.

The following relates to treatment of RF:

For relapsing fever (RF), treatment uses the same classes of antibiotic as for LD. Treatment for infection may be a combined therapy comprising one, two, or sometimes three, antibiotics used at the same time. This may be in the form of sequential treatments or synchronously combined long-term antibiotic treatment. Any of the above antibiotics may be combined or used sequentially.

For example, oral treatment may include a daily single dose of any of an antibiotic from any of the above classes 1-5. For example, oral treatment may consist of a daily single dose of tetracycline 500 mg, doxycycline 200 mg, or, when tetracyclines are contraindicated, erythromycin 500 mg. Treatment duration may be up to 7-10 days or more owing to reported relapses of 20% or greater after single-sequence. In adults, intravenous therapy with doxycycline, erythromycin, tetracycline, or procaine penicillin G may be used when oral therapy is not tolerated.

Procaine penicillin G may be administered at a single dose of 600,000 IU in adult patients with LBRF or 600,000 IU daily in patients with RF.

For example, in a further aspect of the present invention there is provided a method of treating an infection resulting from *Borrelia burgdorferi* sensu lato or RF *Borrelia*, or species of *Borrelia burgdorferi* sensu lato or RF *Borrelia*, the method comprising steps of:— a) identifying *Borrelia burgdorferi* sensu lato or RF *Borrelia* infection, or the species of *Borrelia burgdorferi* sensu lato or RF *Borrelia* infection, using the method according to the first aspect of the present invention;
b) selecting at least one antibiotic that is suitable for treating *Borrelia burgdorferi* sensu lato or RF *Borrelia* infection, or the determined species of *Borrelia burgdorferi* sensu lato or RF *Borrelia;*
c) administering the selected antibiotic(s) to the subject identified in step a as being infected by *Borrelia burgdorferi* sensu lato or RF *Borrelia.*

In a further aspect of the present invention there is provided a method of treating an infection of *Borrelia burgdorferi* sensu lato or RF *Borrelia*, or species of *Borrelia burgdorferi* sensu lato or RF *Borrelia*, the method comprising steps of:— a) selecting at least one antibiotic that is suitable for treating *Borrelia burgdorferi* sensu lato or RF *Borrelia* infection, or the determined species of *Borrelia burgdorferi* sensu lato or RF *Borrelia;*
b) administering the selected antibiotic(s) to a subject that had been identified as having *Borrelia burgdorferi* sensu lato or RF *Borrelia* infection, or the species of *Borrelia burgdorferi* sensu lato or RF *Borrelia* infection, by the method according to the first aspect of the present invention.

Alternatively, the method may be applied for research purposes, for example, research into the physiological effects of *Borrelia burgdorferi* sensu lato or RF *Borrelia*. The method may also be applied in clinical situations when it is important to determine if a subject has been infected with the *Borrelia burgdorferi* sensu lato or RF *Borrelia*. Consequently, in one embodiment in the present invention, the method is a method of diagnosing infection of *Borrelia burgdorferi* sensu lato or RF *Borrelia* or species of *Borrelia burgdorferi* sensu lato or RF *Borrelia* in the subject, the method comprising the steps:— a) detecting the presence or absence of phage or species specific phage in the sample;
b) determining that the subject is infected with *Borrelia burgdorferi* sensu lato or RF *Borrelia*, or a species thereof by detecting the phage or species specific phage in the sample, or determining that the subject is not infected with *Borrelia burgdorferi* sensu lato or RF *Borrelia* or a species thereof, by the lack of detection of the phage, or a species thereof, in the sample.

The terms used in this aspect of the invention are the same as, and so refer back to, the same terms used in earlier aspects of the present invention. For example, samples used in each of the methods of the present invention may be obtained shortly after infection (i.e. early stage infection), or after the infection has been well developed and that bacteria have become sequestered (i.e. late stage infection).

The step of detection for all methods of the invention may be a quantification step, i.e. the amount of phage gene, RNA or protein is calculated. The methods for all methods of the invention may involve the step of taking the sample from a subject. Wherein all the methods of the invention may involve the selection of subjects for treatment for LD when a sample from the subject is determined to be positive for the presence of *Borrelia burgdorferi* sensu lato; or may involve the selection of subjects for treatment for RF when a sample from the subject is determined to be positive for the presence or RF *Borrelia.*

The present invention will now be described, by way of example, with reference to the accompanying figures, in which:—

Figure 1:
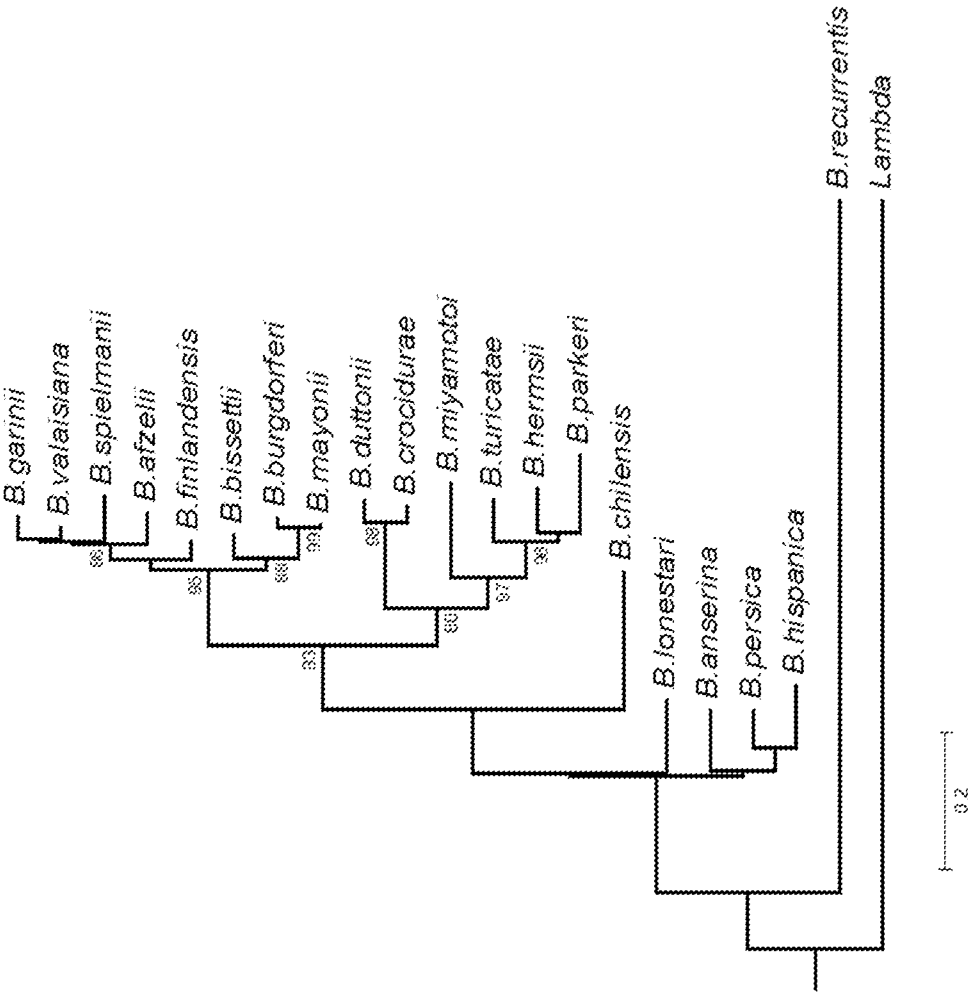
FIG. 1 shows phylogenetic analysis based on the terminase protein showing that the Lyme *Borrelia* species are closely related to each other but naturally separated from other *Borrelia* strains. Scale bar represents 0.2 amino acid changes per site.
Figure 2:
FIG. 2 shows phylogenetic analysis based on the holin protein showing that the Lyme *Borrelia* species are closely related to each other but naturally separated from other *Borrelia* strains. Scale bar represents 0.2 amino acid changes per site.
Figure 3:
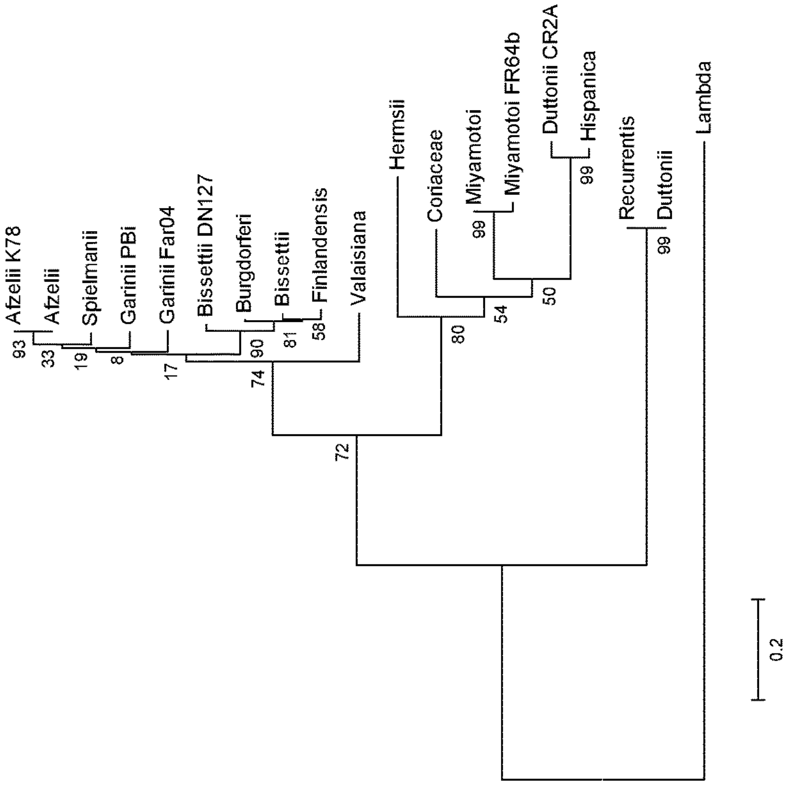

FIG. 3 shows phylogenetic analysis based on the endolysin protein showing that the Lyme *Borrelia* species are closely related to each other but naturally separated from other *Borrelia* strains. The top 10 (from B. *Afzelii* to B. *Valaisiana*) are Lyme *Borrelia* strains, The next 8 (from *B. hermsii* to *B. duttonii*) are Relapsing fever *Borrelia* strains. Scale bar represents 0.2 amino acid changes per site.

Figure 4:
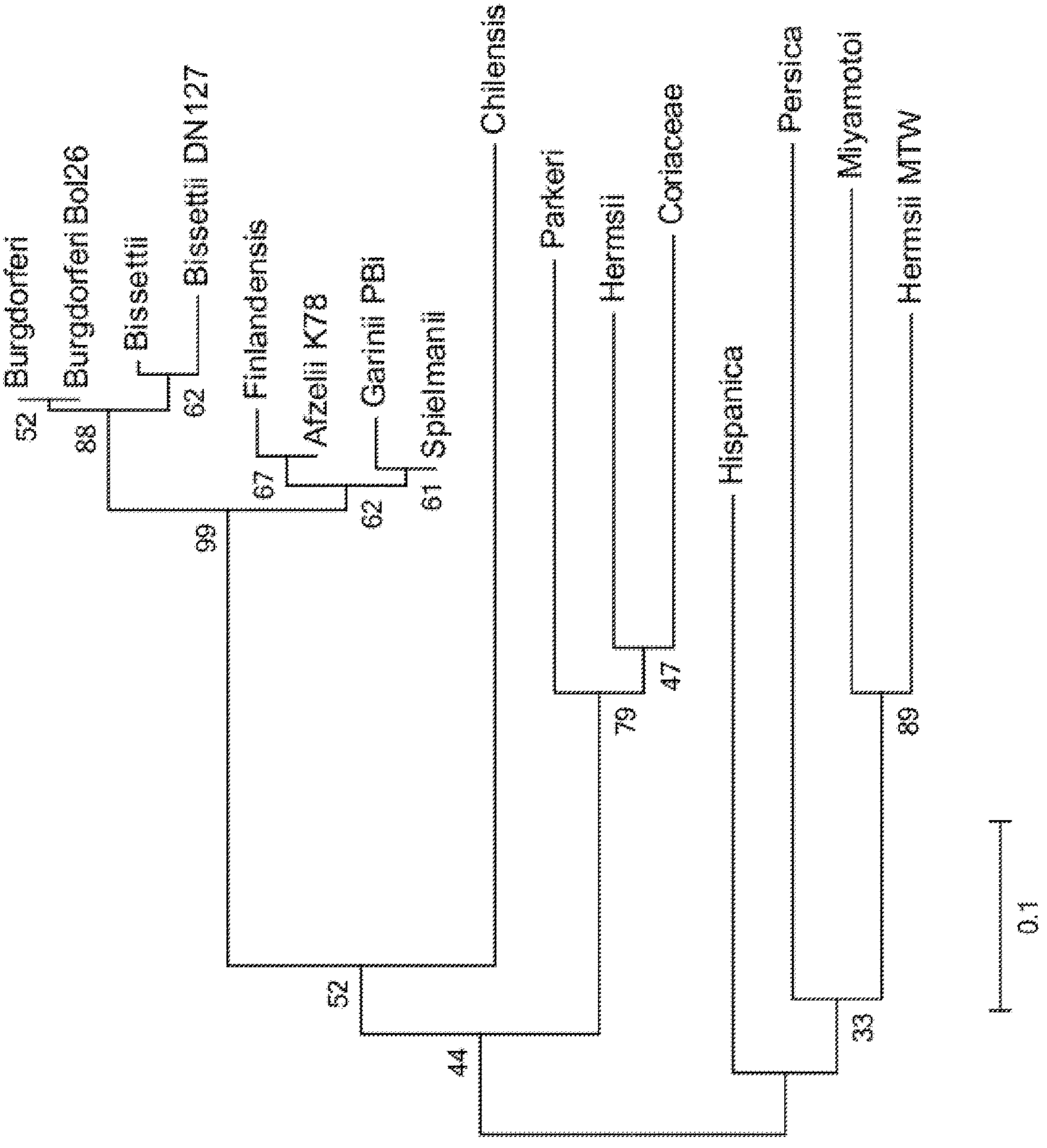

FIG. 4 shows phylogenetic analysis based on the portal protein showing that the Lyme *Borrelia* species are closely related to each other but naturally separated from other *Borrelia* strains. Scale bar represents 0.2 amino acid changes per site.

Figure 5:
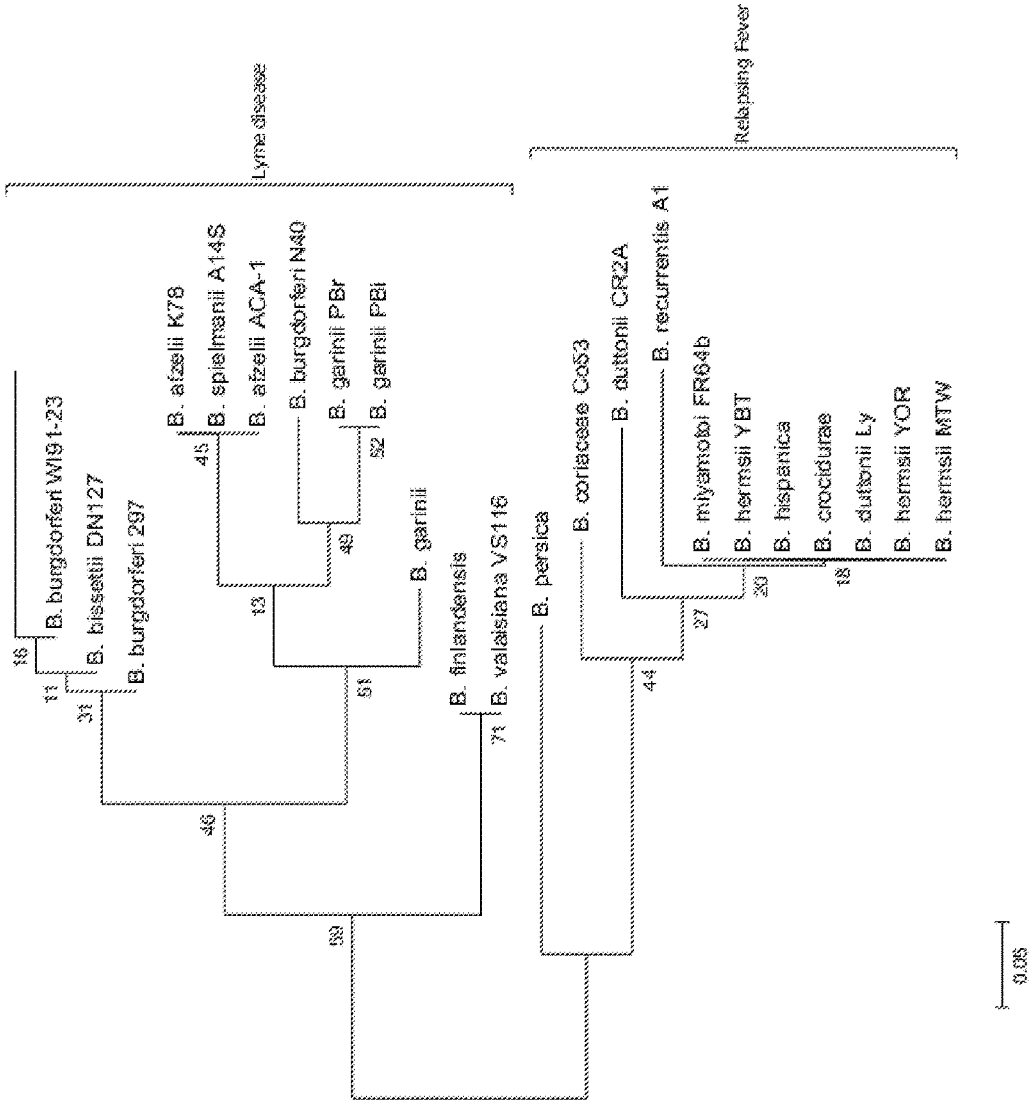

FIG. 5 shows phylogenetic analysis shows phylogenetic analysis based on the integrase protein showing that the Lyme *Borrelia* species are closely related to each other but naturally separated from other *Borrelia* strains. Scale bar represents 0.2 amino acid changes per site.

Figure 6:
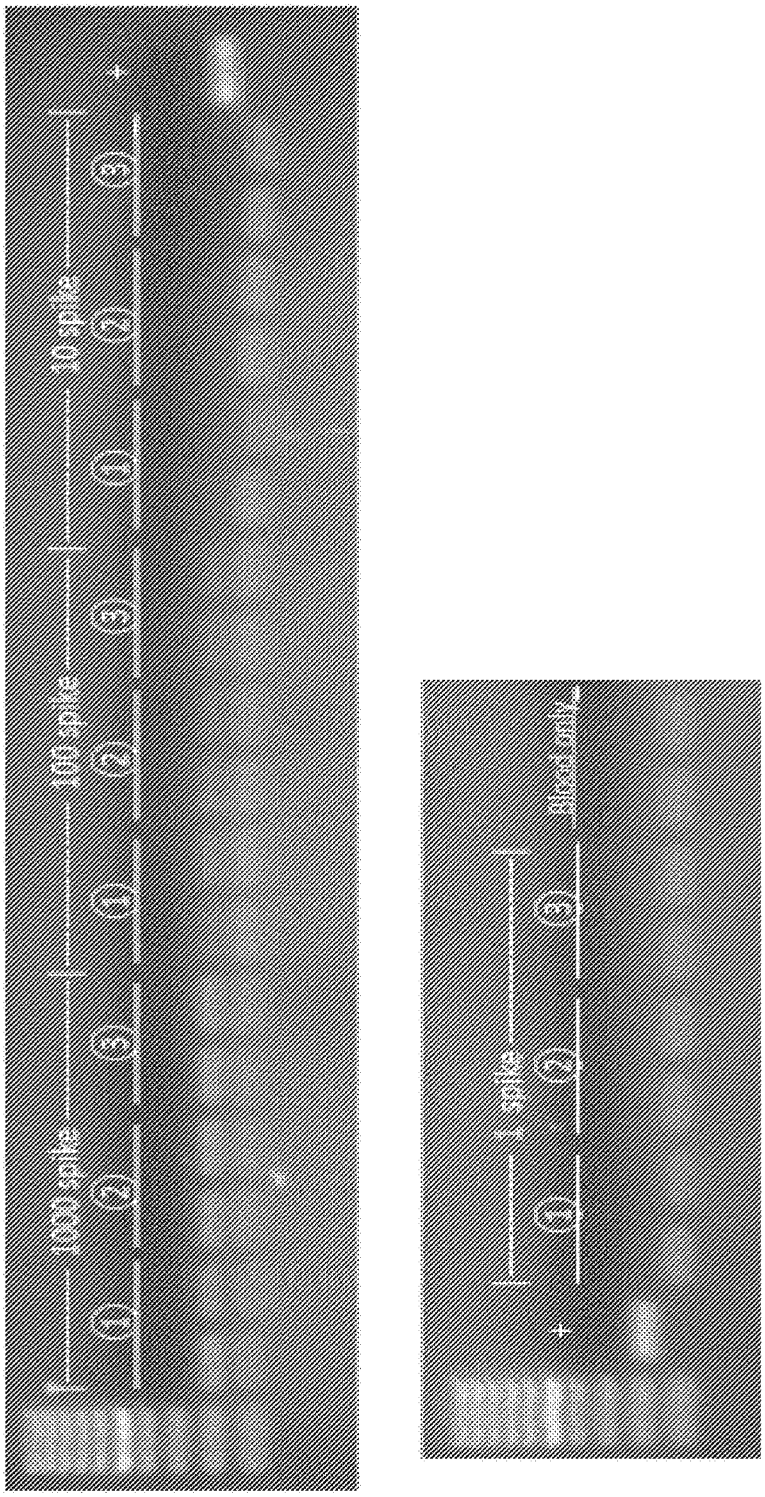

FIG. 6 shows the detection limit of the phage-based method of the present invention, based on analysis of bacterial spiked human blood.

Figure 7:
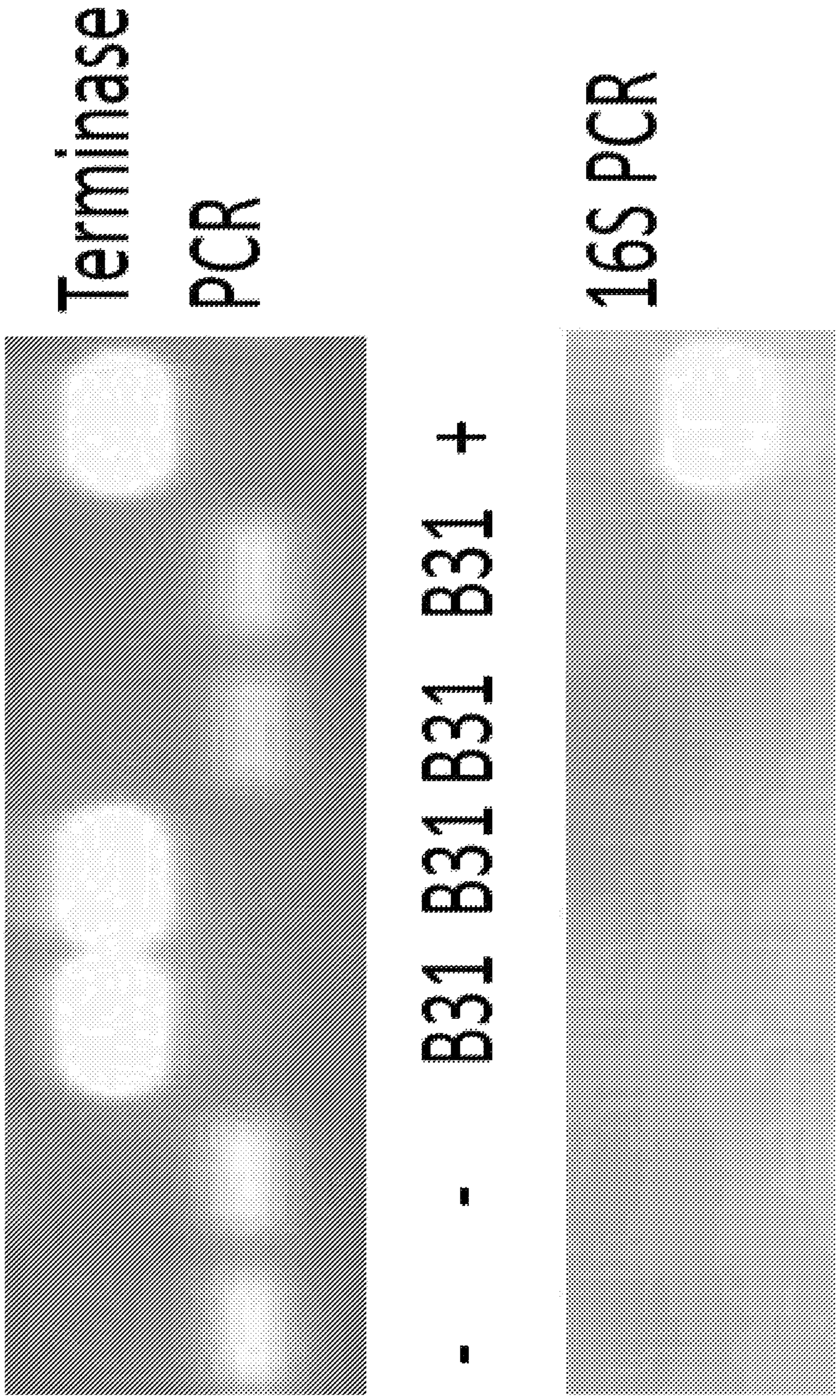

FIG. 7 shows the detection limit of the phage-based method of the present invention in comparison to the standard bacterial 16S-based method.

Figure 8:
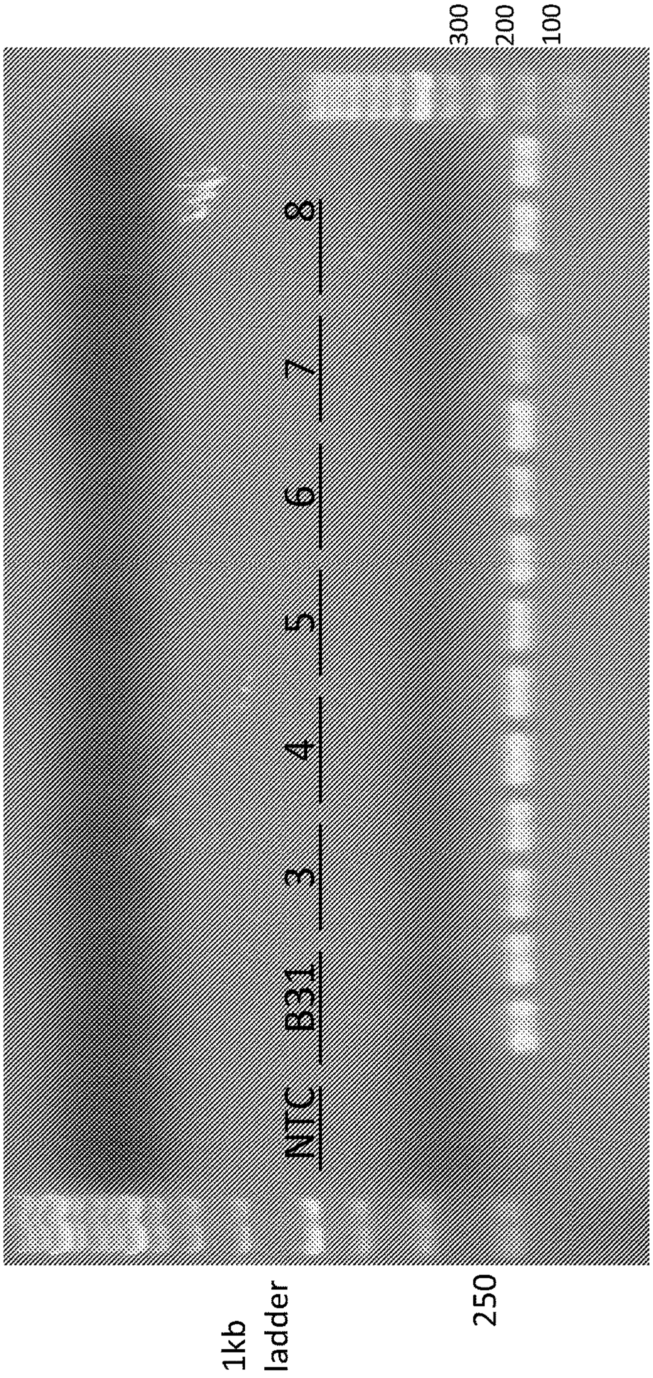

FIG. 8 shows the specificity of the phage-based method according to the present invention for four species of *Borrelia burgdorferi* sensu lato.

Figure 9:
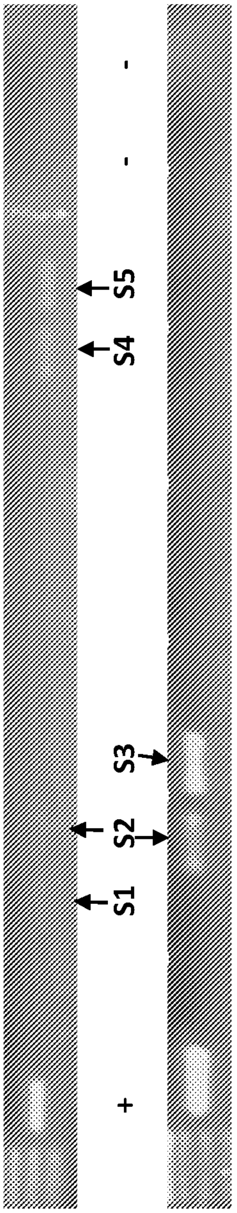

FIG. 9 shows a series of five tenfold dilutions ($10^6$ down to $10^2$ copies) of plasmid DNA carrying the terminase gene fragment. 10 technical repeats were performed for each dilution. As shown, positive amplifications were observed from four diluted plasmid DNA samples down to $10^2$ copies.

Figure 10:
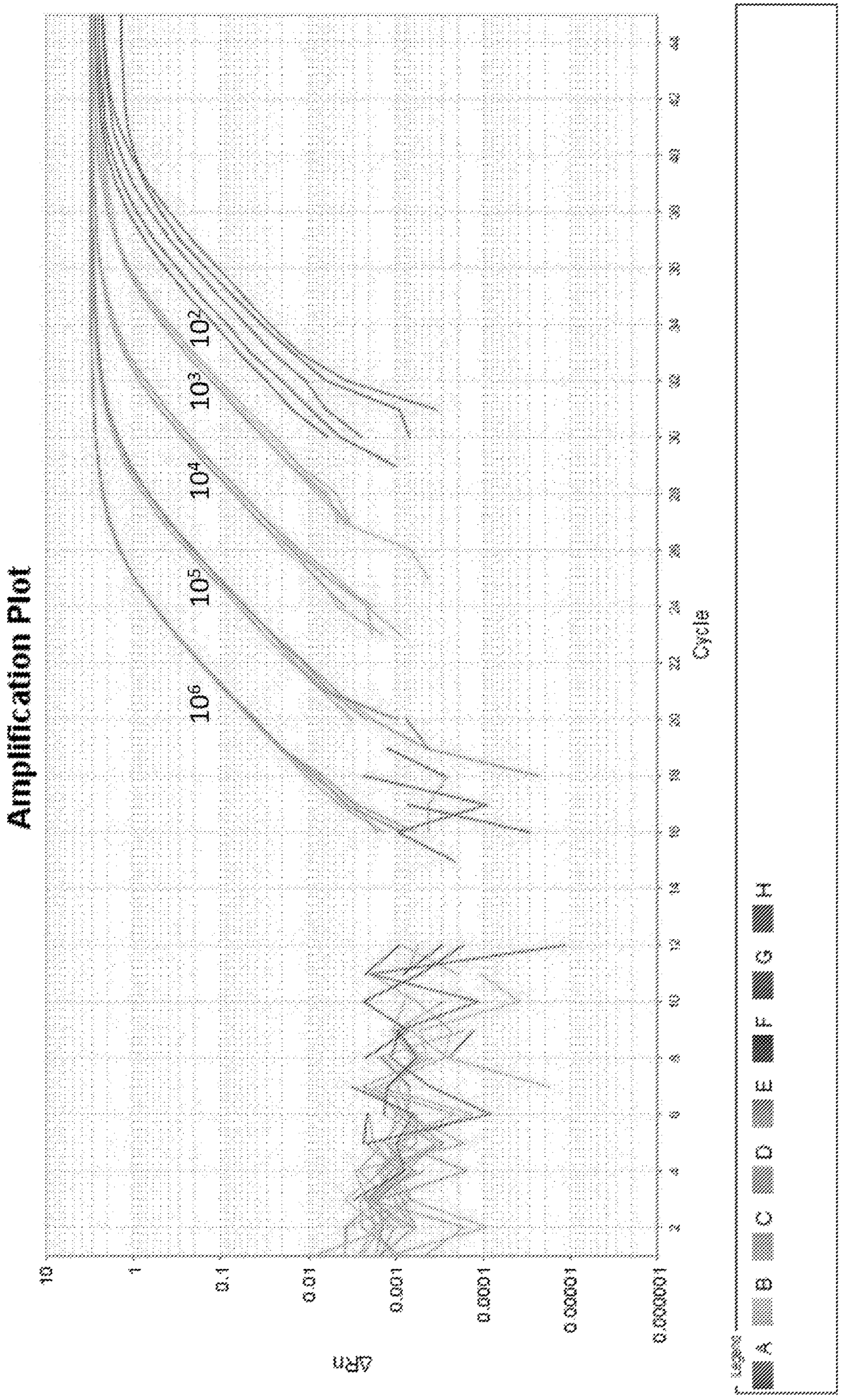

FIG. 10 shows a linear relationship between the concentration of plasmid DNA template and Ct values across with a strong correlation coefficient ($R2=0.99$). In addition, the amplification efficiency of BbFAM was 100%.

Figure 11:
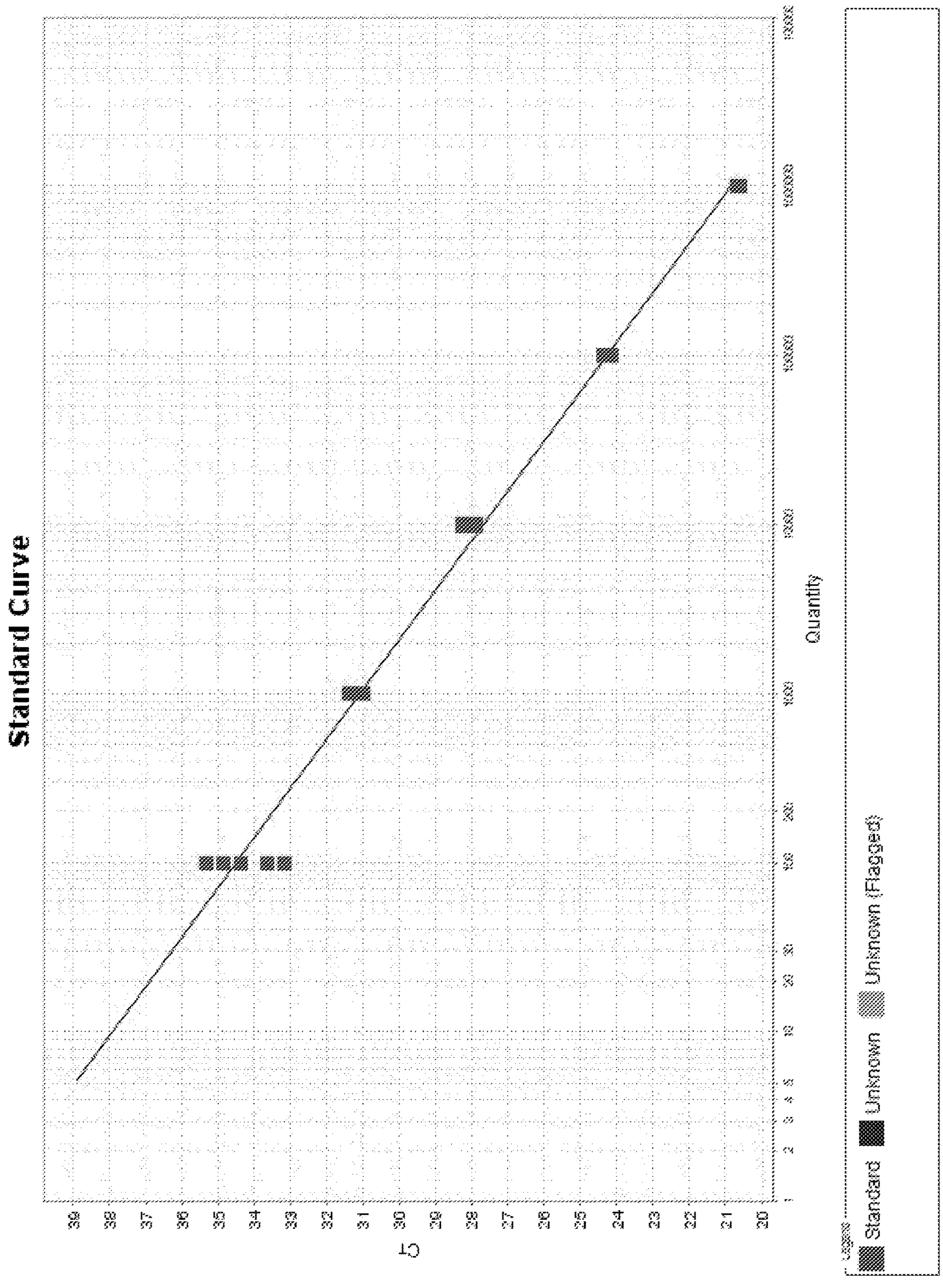

FIG. 11 shows the performance of the phage-based assay against 222 serum samples of different background (Lyme positive, Lyme negative, Lyme borderline, healthy volunteers).

The present invention will now be described with reference to the following examples, which are by way of illustration alone. The following examples are not intended to completely define or otherwise limit the scope of the invention.

EXAMPLES

Lyme Disease

*Borrelia burgdorferi* Sensu Lato Isolates

Lab cultures of *Borrelia burgdorferi* sensu lato (s.l.) strains were provided by professor Sven Bergström (Umeå University, Sweden). Two *Borrelia miyamotoi* strains were provided by the CDC (Centers for Disease Control and Prevention, USA). The lab strains were maintained in BSKII medium. Routine characterisation was carried out using phase contrast microscope.

PCR and Sequencing

DNA was extracted from serum samples using a novel method of combining ammonium hydroxide and phenol chloroform. 600 µL of samples (was incubated in the presence of 1.2 ml 0.7 M ammonium hydroxide at 100° C. for 5 min, followed by 10 min at 100° C. with the tube open. After the tube was cooled to room temperature, the samples were extracted with the same volume of phenol-chloroform (1:1). After incubation time of 5 min at RT, the solution was centrifuged for 10 min at 18 000 g. The clear supernatant was transferred into a new 2 ml tube and mixed with 0.1 volume of 3 M sodium acetate. This suspension was then mixed with 0.7 volumes of room-temperature isopropanol. DNA was precipitated down by centrifuging at 21 000 g for 10 min at 4° C. After decanting the supernatant, 1.5 ml of room-temperature 70% ethanol was added followed by centrifuging at 21 000 g for 10 min at 4° C. The resulting DNA pellet was briefly air dried for 5 min, and dissolved in 50-100 µl of a suitable buffer (such as elution buffer, EB, which is 10 mM Tris-Cl, pH 8.5).

PCR primers were designed manually against conserved regions in all known *Borrelia* phage terminase gene sequences. The primers amplify a 194 bp product from 8 lab all Lyme *Borrelia burgdorferi* s.l. strains. PCRs were carried out in a LabCycler (SensoQuest GmbH, Göttingen, Germany) in a total volume of 50 µl, containing 0.25 mM dNTPs, 3 mM MgCl2, 2 µM primers, 50 ng of template DNA, 0.5 unit of Taq polymerase (Bioline), and 5 µl 10×Taq buffer (Bioline). Amplification conditions were: 94° C. for 2 min, 30 cycles of 94° C. for 45 sec, 48° C. for 45 sec, 72° C. for 1 min, with a final extension of 10 min at 72° C. PCR products were gel-purified using a Qiagen gel extraction kit, and subjected to TOPO TA cloning (Invitrogen). Sequencing was carried out by GATC Biotech. Sequencing results were edited using Chromas 2.33, searched using a nucleotide BLAST (NCBI).

*Borrelia burgdorferi* Sensu Lato Species Identification

A previous reported Multi locus sequence typing (MLST) scheme was used to distinguish different genotypes of *Borrelia*.

Phylogenetic Analysis

Phylogenetic analysis were constructed using the program Molecular Evolutionary Genetics Analysis (MEGA) package version 4.1 (Beta) (Tamura et al., 2007; Kumar et al., 2008). Alignment Explorer/CLUSTAL in MEGA 4.1 (Beta) was used to align the DNA sequences. NJ and MP analysis were conducted on a nucleotide data set; for NJ a maximum composite likelihood model was used and for MP a close-neighbour-interchange with a search level of 3 was used. Supports for clades were estimated using a bootstrap analysis implemented in MEGA using 1,000 replicates. The trees were rooted with phage Lambda (NC_001416) as an outgroup.

Nucleic Acid Hybridisation

"Hybridization" refers to the association of two nucleic acid sequences to one another by hydrogen bonding. Typically, one sequence will be fixed to a solid support and the other will be free in solution. Then, the two sequences will be placed in contact with one another under conditions that favour hydrogen bonding.

Factors that affect this bonding include: the type and volume of solvent; reaction temperature; time of hybridization; agitation; agents to block the non-specific attachment of the liquid phase sequence to the solid support (Denhardt's reagent or BLOTTO); concentration of the sequences; use of compounds to increase the rate of association of sequences (dextran sulphate or polyethylene glycol); and the stringency of the washing conditions following hybridization.

"Stringency" refers to conditions in a hybridization reaction that favour association of very similar sequences over sequences that differ. For example, the combination of temperature and salt concentration should be chosen that is approximately 120 to 200° C. below the calculated Tm of the hybrid under study. The temperature and salt conditions can often be determined empirically in preliminary experiments in which samples of genomic DNA immobilized on filters are hybridized to the sequence of interest and then washed under conditions of different stringencies. See Sambrook et al. at page 9.50.

Variables to consider when performing, for example, a Southern blot are (1) the complexity of the DNA being blotted and (2) the homology between the probe and the sequences being detected. The total amount of the fragment(s) to be studied can vary a magnitude of 10, from 0.1 to 1 mg for a plasmid or phage digest to 10-9 to 10-8 g for a single copy gene in a highly complex eukaryotic genome. For lower complexity polynucleotides, substantially shorter blotting, hybridization, and exposure times, a smaller amount of starting polynucleotides, and lower specific activity of probescan be used. For example, a single-copy yeast gene can be detected with an exposure time of only 1 hour starting with 1 mg of yeast DNA, blotting for two hours, and hybridizing for 4-8 hours with a probe of 108 cpm/mg.

For a single-copy mammalian gene a conservative approach would start with 10 mg of DNA, blot overnight, and hybridize overnight in the presence of 10% dextran sulphate using a probe of greater than 108 cpm/mg, resulting in an exposure time of 24 hours.

Several factors can affect the melting temperature (Tm) of a DNA-DNA hybrid between the probe and the fragment of interest, and consequently, the appropriate conditions for hybridization and washing. In many cases the probe is not 100% homologous to the fragment. Other commonly encountered variables include the length and total G+C content of the hybridizing sequences and the ionic strength and formamide content of the hybridization buffer. The effects of all of these factors can be approximated by a single equation: where Ci is the salt concentration (monovalent ions) and n is the length of the hybrid in base pairs (slightly modified from Meinkoth & Wahl (1984) Anal. Biochem. 138: 267-284).

In designing a hybridization experiment, some factors affecting nucleic acid hybridization can be conveniently altered. The temperature of the hybridization and washes and the salt concentration during the washes are the simplest to adjust. As the temperature of the hybridization increases (i.e. stringency), it becomes less likely for hybridization to occur between strands that are no homologous, and as a result, background decreases. If the radiolabeled probe is not completely homologous with the immobilized fragment (as is frequently the case in gene family and interspecies hybridization experiments), the hybridization temperature must be reduced, and background will increase. The temperature of the washes affects the intensity of the hybridizing band and the degree of background in a similar manner. The stringency of the washes is also increased with decreasing salt concentrations.

In general, convenient hybridization temperatures in the presence of 50% formamide are 42° C. for a probe with is 95% to 100% homologous to the target fragment, 37° C. for 90% to 95% homology, and 32° C. for 85% to 90% homology. If the homology between the probe and the target fragment are not known, the simplest approach is to start with both hybridization and wash conditions which are nonstringent. If non-specific bands or high background are observed after autoradiography, the filter can be washed at high stringency and re-exposed. If the time required for exposure makes this approach impractical, several hybridization and/or washing stringencies should be tested in parallel. Nucleic acid Probe Assays.

Example 1: Efficacy of Phage-Based Test, as Shown in Spiked Blood

A known number of cells of *Borrelia burgdorferi* s.s. B31 strain (1000, 100, 10, and 1 cell/cell) were added into 1 ml of commercial available healthy human whole blood (3 replicas). Total DNA was extracted from 100 μl of the spiked blood, respectively using the Qiagen blood and tissue kit. The extracted DNA was then used as a template for PCR amplification of the terminase gene (primers used were as shown in SEQ ID No. 70 and 71—forward and reverse).

As clearly demonstrated in the gel picture shown in FIG. 6, the PCR products were seen in the DNA from blood samples spiked with 100 cells or more of the B31 strain. This showed that 100 *Borrelia* cells will be needed to generate a positive terminase PCR test. This also demonstrated that the terminase PCR detection limit is 100 *Borrelia*/ml of blood, this concentration reflects the normal *Borrelia* concentration in Lyme patients. No terminase PCR product can be seen from the total DNA extracted from whole blood without *Borrelia* spiking (see lanes marked blood only). A false signal for the presence of detection was not found.

Comparison with Known Methodologies

The present invention, as described above, using the terminase PCR targeting *B. burgdorferi* s.l. was practiced on samples with known concentrations of *Borrelia burgdorferi* strain B31. The sensitivity of the present test was compared with bacteria-based PCR, our terminase PCR targeting *B. burgdorferi* s.l. phage-based PCR. The test of the present invention showed a markedly higher sensitivity compared to the known test, and could detect bacteria at a concentration ~1 bacterium per ml (see Table 1).

TABLE 1

| Number of *Borrelia* bacteria/ml | Current bacterial PCR based on bacterial 5S-23S | Leicester phage PCR |
|---|---|---|
| <100 | Positive | Positive |
| <10 | Weak signal | Positive |
| <1 | Negative | Positive |

Conclusion

The phage-based PCR was positive against Lyme *Borrelia* suspension with a concentration of less than 1 bacterium per ml, while the bacterial PCR was negative.

Example 2: Comparative Study of Methods of Present Invention with Conventional 16sPCR Method Four individual *Borrelia burgdorferi* B31 cultures were diluted to 10 *Borrelia*/ml, 100 μl of these diluted cultures were then subjected to DNA extraction using the Qiagen blood and tissue kit. The resulting extracted DNA was then used as a template for PCR amplification of the terminase gene (primers used were as shown in SEQ ID No. 70 and 71—forward and reverse) and as a template for PCR amplification of the 16S (a bacterial gene for ribosomal RNA, commonly as a molecular diagnostic tool for detecting presence of absence of bacteria). As can be seen in the gel picture shown in FIG. 7, two strong positive results were seen with terminase PCR, while only one weak positive with 16S PCR was identified. The leftmost two lanes are PCR negatives (ie did not include starting material derived from cultures), the rightmost lane is PCR positive (ie included a high concentration of bacterial cells).

Conclusion

This example demonstrated that the efficiency of terminase PCR is higher than 16S PCR.

Example 3: Demonstrate of Test According to Present Invention on Different *Borrelia Burgdorferi* s.l. Species Terminase PCR was carried out against a set of different *Borrelia* genotypes (different isolates).

The gel picture of FIG. 8 shows the results of this PCR: B31=*Borrelia burgdorferi B*31; the numbers are *Borrelia* strains as shown in the table below:

TABLE 2

| | Isolate names | Scientific names |
|---|---|---|
| 3 | VS185 P9 | *Borrelia burgdorferi* s.s. |
| 4 | NE218 | *Borrelia valaisiana* |

TABLE 2-continued

| | Isolate names | Scientific names |
|---|---|---|
| 5 | ACA1 | *Borrelia afzelii* |
| 6 | UK filtered | *Borrelia burgdorferi* s.s. |
| 7 | 190 P9 | *Borrelia garinii* |
| 8 | China23 | *Borrelia burgdorferi* s.s. |

This demonstrated that this terminase PCR technique of the present invention can amplify the four key strains of *Borrelia burgdorferi* s.l. group, which are *Burgdorferi, afzelii*, and *valaisiana*. This terminase PCR technique was also applied to other bacteria, such as *Clostridium difficile, Burkholderia thailandensis, E. coli, Salmonella, legionellae*, and haemophilia strains. None of these bacteria generated any PCR product with terminase primer.

Further analysis was carried out to determine the efficiency of the method to distinguish between Lyme *Borrelia* and relapsing fever *Borrelia* strains.

Primers and TaqMan probes (Table 3) were designed based on the *B. burgdorferi* terminase gene sequence (GenBank accession NC 000948.1) using PrimerQuest® Tool (IDT). To ensure the specificity of the primer/probe combinations (referred to as 'BbFAM'), BLAST analysis using sequences submitted to GenBank was performed. All hits with e-value <0.01 were Lyme *Borrelia* species dominated by *B. burgdorferi* with one hit of each of the following *Borrelia* strains: *B. mayonii, B. garinii, B. afzelii, B. bisettii*, and *B. valasiana*. In addition, 'In silico' was performed against all the available bacterial species, PCR product of the correct sizes was only observed from plasmid fractions of *Borrelia burgdorferi*. This demonstrated that the primer/probe combinations can detect the Lyme *Borrelia* strains. The TaqMan probe was labelled 5' with 6-carboxyfluorescein (FAM) fluorescent dye and a double-quencher with a ZEN™. Quencher and Iowa Black FQ to the 3' (5'FAM/ZEN/3'IBFQ). These double-quenched probes generate less background and increased signal compared to probes containing a single quencher. Both primers, the probe and PrimeTime Gene Expression Master Mix were supplied by IDT.

TABLE 3

Sequences of primers and probes for terminase real-time PCR (BbFAM)

| | Sequence (5' to 3') | Expected amplicon size (bp) | GeneBank accession no. |
|---|---|---|---|
| Probe (SEQ ID NO. 81) | TGCTGGGTCTAAATATGCTATCGGGC | 147 | NC_000948.1 |
| Primer F (SEQ ID NO. 79) | GAGTGGATAGCAAGCACTGAT | | |
| PrimerR (SEQ ID NO. 80) | ATCATCAACTCGCTCCATAACA | | |

As seen in table 4, the primer/probe were tested against DNA extracted from different genotypes of *Borrelia* strains. All Lyme *Borrelia* strains (1-6) tested generated a positive PCR with a threshold cycle (Ct) value <30. No Ct value can be detected from Relapsing fever *Borrelia* strains. Apart from 'in silico' PCR, 'wet experiment' was also carried out to confirm that no PCR products were observed when BbFAM PCR was performed against a range of different bacterial DNA including, *E. coli, Pseudomonas, Clostridium, Haemophilus, Burkholderia*, and *Salmonella*.

TABLE 4

BbFAM PCR against different Lyme *Borrelia* and Relapsing fever *Borrelia* strains.

| | Isolate Names | Scientific Names | BbFAM PCR results |
|---|---|---|---|
| 1 | VS185 P9 | *Borrelia burgdorferi* | Positive |
| 2 | NE218 | *Borrelia valasiana* | Positive |
| 3 | ACA1 | *Borrelia afzelii* | Positive |
| 4 | UK filtered | *Borrelia burgdorferi* | Positive |
| 5 | 190 P9 | *Borrelia garinii* | Positive |
| 6 | China23 | *Borrelia burgdorferi* | Positive |
| 7 | 1120 | *Borrelia duttonii* | Negative |
| 8 | Her HS1 | *Borrelia hemsii* | Negative |
| 9 | CA128 | *Borrelia bisettii* | Negative |
| 10 | HT31 | *Borrelia miyamotoi* | Negative |
| 11 | FR64b | *Borrelia miyamotoi* | Negative |

To test the robustness, efficiency and the limit of detection (LOD) of the BbFAM PCR, a series of five tenfold dilutions of a plasmid carrying terminase gene fragment were amplified with BbFAM. To construct a standard for real time PCR, a plasmid carrying the terminase gene fragment was made. This plasmid served as the positive control and helped the calculations of the copy numbers in each PCR. The terminase plasmid was constructed as described below:

PCR primers were designed using Primer Blast against terminase gene sequence (SEQ ID No 1). The primers were FTer721:AGACTAAGATGCGGGCAAGA (SEQ ID NO. 82) and RTer721:TTGCATCAAGAGCGTCATCA (SEQ ID NO. 83). A 721 bp PCR product was generated. PCRs were carried out in a LabCycler (SensoQuest GmbH, Göttingen, Germany) in a total volume of 50 μl, containing 0.25 mM dNTPs, 3 mM MgCl2, 3 μM primers, 50 ng of template DNA, 0.5 unit of Taq polymerase (Bioline), and 5 μl 10×Taq buffer (Bioline). Amplification conditions were: 94° C. for 2 min, 30 cycles of 94° C. for 30 sec, 50° C. for 30 sec, 72° C. for 1 min, with a final extension of 10 min at 72° C. PCR products were gel-purified using a Qiagen gel extraction kit, and subjected to cloning using NEB® PCR Cloning Kit according to the standard protocol. The positive clones were confirmed by PCR and sequencing. The resulting plasmid carrying terminase gene fragments were purified using Qiagen plasmid kit and used as positive controls. The concentration of DNA was measured with a Qubit Fluorometer (Invitrogen). The copy number of the plasmid DNA with the terminase gene fragment was calculated according the following formula (available online):

$$\text{Number of copies} = \frac{6.022\times10^{23}(\text{copies/mol})\times DNA\ \text{amount(ng)}}{DNA\ \text{length(bp)}\times10^{9}(\text{ng/g})\times650(\text{g/mol/bp})}$$

To work out the limit of detection (LOD) of the Taqman real time PCR, firstly 10-fold serial dilutions of the plasmid DNA carrying terminase fragment were tested to evaluate the performance of Taqman PCR. Each dilution ($10^6$-$10^2$) was tested by BbFAM PCR with five replicates (Table 5).

Next, the plasmid DNA was diluted from 1000 copies numbers to 100, 80, 60, 40, 20, 10, 5, and 1 copies/PCR. Ten replicates were used for each dilution. Probit analysis in SPSS was performed to calculate the LOD of 32 copies of plasmids with 95% probability.

The results were summarised in the following two tables:

TABLE 5

Taqman real time PCR performance on plasmid DNA carrying terminase gene fragment

| Copy number/PCR | Average Ct |
|---|---|
| $10^6$ | 20.63 |
| $10^5$ | 24.32 |
| $10^4$ | 28.03 |
| $10^3$ | 31.12 |
| $10^2$ | 34.27 |

TABLE 6

Determination of LOD of Taqman real time PCR (10 replicates for each dilution)

| Copy number/PCR | Number of replicates | Number of PCR positive replicates (% of positive) |
|---|---|---|
| 100 | 10 | 10 (100%) |
| 80 | 10 | 10 (100%) |
| 60 | 10 | 10 (100%) |
| 40 | 10 | 10 (100%) |
| 20 | 10 | 6 (60%) |
| 10 | 10 | 5 (50%) |
| 5 | 10 | 2 (20%) |
| 1 | 10 | 0 |

The LOD determined by Probit analysis with 95% probability was 30 copies of plasmid DNA.

The copy numbers of plasmid DNA template per PCR ranged from $10^6$ to $10^2$. As shown in FIG. 10, positive amplifications were observed from all the plasmid DNA samples. As shown in FIG. 11, a linear relationship between the concentration of DNA template and Ct values across with a strong correlation coefficient ($R^2$=0.99). In addition, the amplification efficiency of BbFAM was 100%. This demonstrated the high sensitivity and efficiency of the PCR.

To rule out the possibility of human DNA interference, human DNA and healthy whole blood were purchased from Sigma. Total DNA was extracted from the healthy whole blood. Both DNAs were examined using BbFAM PCR. No Ct values were observed from any PCRs, while positive PCR targeting human housekeeping genes RNase P produced positives. This confirmed that the human DNA had no effect on BbFAM PCR.

Conclusion

This experiment demonstrated that this terminase PCR is specific for *Borrelia burgdorferi* sensu lato and that using real time sequencing, the test has a very low limit of detection (LOD).

PCR primers for holin, endolysin and for amplifying the region which contains both these genes (SEQ ID NO. 72-77; the region containing both genes=SEQ ID NO. 78) have also been demonstrated to be able to amplify the correct regions of Lyme *Borrelia.*

Example 4: Comparative Study of Methods of Present Invention with Conventional 16sPCR Method Practiced in Serum Sample Five Lyme-positive serum samples (S1-S5) (as tested and confirmed by antibody and clinical presentation tests) were subjected to DNA extraction using Qiagen Blood and tissue kit. The DNAs were then analysed using both terminase (top panel) and 16S (bottom panel) PCR primers, respectively (in the case of terminase, primers used were as in SEQ ID No. 70 and 71). As seen in the gel pictures shown in FIG. 9, four PCR positive results were observed for terminase (S1, S2, S4 and S5), while only two positive can be seen for 16S (S2 and S3). This was a pilot study prior to real time PCR experiments performed with large scale clinical trials (see below).

Conclusion

This example demonstrated that terminase PCR has a much higher sensitivity than techniques based on 16s. +=control, a high concentration of bacterial cells.

Example 5: Clinical Results

The sensitivity of the BbFAM PCR was also investigated against 222 serum samples, which are all derived from clinically-confirmed Lyme patients (among those patients, 91 of patients have ELISA and or Western Blot data).

207 out of the 222 patients showed BbFAM PCR positive, representing a sensitivity of 93.2%.

91 out of 222 patients had been examined by either ELISA and/or WB.

Out of the 91 patients, 16 of them showed ELISA and/or WB positive, representing a sensitivity of 17.6%. Out of these 91 patients, 85 showed positive to BbFAM PCR, representing a sensitivity of 93.4%, which agrees well with the sensitivity calculated based on 222 patients. If you look into the correlation between BbFAM PCR results to the ELISA/WB data, you will find that the 16 ELISA and/or WB positive patients all showed BbFAM PCR positive. In addition, 6 patients from the 91 patient cohort who displayed BbFAM PCR negative also showed ELISA/WB negative. The vast majority of clinically confirmed patients in the 91 cohort only showed positive to BbFAM PCR, but negative to ELISA/WB, an indication of high sensitivity and reliability of BbFAM PCR. To compare the sensitivity of BbFAM with the current commercial Lyme PCR detection kit, GeneProof *Borrelia burgdorferi* PCR Kit was applied to 65 serum samples that were randomly selected from the 222 cohort. Only 7 out of 65 serum samples showed positive to GeneProof kit (a sensitivity of 10.8%).

SUMMARY

This is the first study to use a molecular marker to investigate the distribution and diversity of *Borrelia* phages.

A phylogentic tree constructed by the inventors on phage terminase gene shows that it is a good phylogenetic marker because the *Borrelia* phage sequences form a discrete yet genetically diverse group which is clearly separated from other spirochetes. Lyme disease infection (ie *Borrelia burgdorferi* sensu lato infection) forms a discrete well supported clade and these correlate well with bacteria.

Summary for Lyme Disease

1) Overall ability to identify LD much higher sensitivity compared to bacterial 16S method. In addition, the clinical results also demonstrate that the phage terminase-based real time PCR is significantly more sensitive than bacterial 16S-based PCR (GeneProof PCR kit).
2) Relates to multiple species of *Borrelia burgdorferi* sensu lato (Table 4: Phage terminase-based real time PCR against different Lyme *Borrelia* and Relapsing fever *Borrelia* strains)
3) Early detection possible as the phage based test can detect a low concentration of bacteria. The real time PCR has a low detection limit of 30 copies of terminase gene.

Relapsing Fever

Example 6: Differentiation of Relapsing Fever (*Borellia Hermsii*) from Lyme Disease Primers and TaqMan probes (Table 8) were designed based on the *B. hermsii* terminase gene sequence using PrimerQuest® Tool (IDT). To ensure the specificity of the primer/probe combinations (referred to as 'BhFAM'), BLAST analysis using sequences submitted to GenBank was performed. Big E-value drops were observed from 0.000004 to 0.004 between *B. hermsii* hit and the next closest blast hit of *B. turicatae* and *B. parkeri.*

'In silico PCR' was performed against all the available bacterial species, PCR product of the correct sizes was only observed from *Borrelia hermsii*. The TaqMan probe was labelled 5' with 6-carboxyfluorescein (FAM) fluorescent dye and a double-quencher with a ZEN™ Quencher and Iowa Black FQ to the 3' (5'FAM/ZEN/3'IBFQ). These double-quenched probes generate less background and increased signal compared to probes containing a single quencher. Both primers, the probe and PrimeTime Gene Expression Master Mix were supplied by IDT. by IDT.

TABLE 8

Sequences of primers and probe targeting terminase gene in *B. hermsii* (BhFAM)

| | Sequence (5' to 3') | Expected amplicon size (bp) | GeneBank accession no. |
|---|---|---|---|
| Probe | AGGCACCAATAGCATATTTAGATCCTGCA | 124 | CP014792.1 |
| Primer F | GGAGAATGGGTTGCGTCATA | | |
| Primer R | GCGCAGTATTATCACCTCCAATA | | |

As seen in table 9, the primer/probe were tested against DNA extracted from different genotypes of *Borrelia* strains. No positive can be seen from all Lyme *Borrelia* strains (1-6) and other relapsing fever *Borrelia* strains. Only *B. hermsii* generated the correct PCR product. Apart from 'in silico' PCR, 'wet experiment' was also carried out to confirm that no PCR products were observed when BhFAM PCR was performed against a range of different bacterial DNA including, *E. coli, Pseudomonas, Clostridium, Haemophilus, Burkholderia*, and *Salmonella*.

TABLE 9

BhFAM PCR against different Lyme *Borrelia* and Relapsing fever *Borrelia* strains

| | Isolate Names | Scientific Names | BbFAM PCR results |
|---|---|---|---|
| 1 | VS185 P9 | *Borrelia burgdorferi* | Negative |
| 2 | NE218 | *Borrelia valasiana* | Negative |
| 3 | ACA1 | *Borrelia afzelii* | Negative |
| 4 | UK filtered | *Borrelia burgdorferi* | Negative |
| 5 | 190 P9 | *Borrelia garinii* | Negative |
| 6 | China23 | *Borrelia burgdorferi* | Negative |
| 7 | 1120 | *Borrelia duttonii* | Negative |
| 8 | Her HS1 | *Borrelia hermsii* | Positive |
| 9 | CA128 | *Borrelia bisettii* | Negative |
| 10 | HT31 | *Borrelia miyamotoi* | Negative |
| 11 | FR64b | *Borrelia miyamotoi* | Negative |

Example 7: Differentiation of Relapsing Fever (*Borrelia miyamotoi*) from Lyme Disease Two sets of primers and TaqMan probes were designed based on two *B. miyamotoi* terminase genes using PrimerQuest® Tool (IDT) with manual inspection (referred to as 'BmFAM' and 'Bm-2FAM', respectively as shown in the Table 10). Both sets target different versions of terminase genes located on different plasmids, therefore they are complementary to each other in detecting *B. miyamotoi*. To ensure the specificity of the primer/probe combinations, BLAST analysis using sequences submitted to GenBank was performed. Big E-value drops were observed for both sets of Taqman probes. For example, BmFAB and Bm-1FAM showed E-value drops from 0.0002 to 0.79 and 0.006 to 1.6, respectively, between *miyamotoi* hits and the next closest blast hit. 'In silico PCR' (http://insilico.ehu.es/PCR/) was performed against all the available bacterial species, PCR product of the correct sizes was only observed from *Borrelia miyamotoi*. This demonstrated specificity of the primer/probe combinations in detecting *B. miyamotoi* strains. The TaqMan probe was labelled 5' with 6-carboxyfluorescein (FAM) fluorescent dye and a double-quencher with a ZEN™. Quencher and Iowa Black FQ to the 3' (5'FAM/ZEN/3'IBFQ). These double-quenched probes generate less background and increased signal compared to probes containing a single quencher. Primers, probes and PrimeTime Gene Expression Master Mix were supplied by IDT.

TABLE 10

Two sets of primer/probes (BmFAM and Bm-2FAM) targeting terminase genes in *Borrelia miyamotoi* strains

| | | Sequence (5' to 3') | Expected amplicon size (bp) | GeneBank accession no. |
|---|---|---|---|---|
| BmFAM | Probe | AGTGCACTTTGTGTGCTTGAAATGGT | 120 | CP004220.1 |
| | Primer F | AGCCTACCTAGATCCTGCTTAT | | |
| | Primer R | GGGTCACTTGCTGGTAGTTT | | |
| Bm-2FAM | Probe | ACGCTTCAGAGGCTCTAATTCTG | 87 | CP017131.1 |
| | Primer F | GTGGAGATAAGGCAAGTGA | | |
| | Primer R | CTTTATGAAGAGTAGTTGCTTC | | |

As seen in table 11, the primer/probe were tested against DNA extracted from different genotypes of *Borrelia* strains. No Ct value can be detected from all Lyme *Borrelia* strains (1-6) and relapsing fever *Borrelia* strains. PCR positive can only be observed in *B. miyamotoi* DNA. In addition, no PCR products were observed when both sets of primer/probe were performed against a range of different bacterial DNA including, *E. coli, Pseudomonas, Clostridium, Haemophilus, Burkholderia*, and *Salmonella*.

TABLE 11

BmFAM and Bm-2FAM PCR against different Lyme *Borrelia* and Relapsing fever *Borrelia* strains.

| | Isolate Names | Scientific Names | BbFAM PCR results |
|---|---|---|---|
| 1 | VS185 P9 | *Borrelia burgdorferi* | Negative |
| 2 | NE218 | *Borrelia valasiana* | Negative |
| 3 | ACA1 | *Borrelia afzelii* | Negative |
| 4 | UK filtered | *Borrelia burgdorferi* | Negative |
| 5 | 190 P9 | *Borrelia garinii* | Negative |
| 6 | China23 | *Borrelia burgdorferi* | Negative |
| 7 | 1120 | *Borrelia duttonii* | Negative |
| 8 | Her HS1 | *Borrelia hermsii* | Negative |
| 9 | CA128 | *Borrelia bisettii* | Negative |
| 10 | HT31 | *Borrelia miyamotoi* | Positive |
| 11 | FR64b | *Borrelia miyamotoi* | Positive |

As a pilot study, 43 tubs of blood/serum samples derived from healthy volunteers and Lyme patients were randomly chosen and subjected to test agasint BmFAM and BbFAM, respectively. Results were as follows: 7 (16.3%) tubes showed positive to BmFAM, while 26 (60.5%) showed positive to BbFAM. This demonstrated a potential low level of *B. miyamotoi* carriage in the population. Large scale clinical validation is on-going.

Summary for Relapsing Fever

1) The phage-based test can specifically amplify RF *Borrelia* strains, and didn't amplify LD *Borrelia* strains. This makes it possible to design a phage terminase-based duplex PCR to diagnose LD and RF at the same time.
2) The phage-based RF tests have the ability to distinguish different RF *Borrelia* strains, such as *B. miyamotoi* and *B. hermsii*. This would enable clinicians to better manage and prescribe antibiotics once the RF species was known. With a fully validated phage-based RF test, clinicians would be better informed about which *Borrelia* species are causing the symptoms.
3) As a result of these successful initial validation results, large scale clinical validation is currently under way.

What is claimed is:

1. A method of determining infection of a subject by either *Borrelia* burgodorferi sensu lato or Relapsing Fever *Borrelia* with phage specific for *Borrelia* by determining presence or the absence of the phage dispensed from and specific to *Borrelia burgdorferi* sensu lato or Relapsing Fever *Borrelia* in a blood sample derived from the subject infected or suspected of being infected by *Borrelia burgodorferi sensu lato* or Relapsing Fever *Borrelia*, the method comprising the steps of:
   - a) extracting phage nucleic acid from the blood sample by
   - i) incubating the *Borrelia* in ammonium hydroxide and
   - ii) adding phenol-chloroform to the *Borrelia* and ammonium hydroxide mixture,
   - b) detecting the presence or absence of the phage nucleic acid dispensed from and specific to *Borrelia burgdorferi* sensu lato or Relapsing Fever *Borrelia* in the blood sample obtained from a subject infected or suspected of being infected by *Borrelia burgodorferi sensu lato* or Relapsing Fever *Borrelia*; and
   - c) determining the *Borrelia burgdorferi* sensu lato or Relapsing Fever *Borrelia* infection of the subject wherein detection of the phage specific to either of *Borrelia burgdorferi* sensu lato or Relapsing Fever *Borrelia* in the sample is indicative of infection of the subject of *Borrelia* burgodorferi sensu lato or Relapsing Fever *Borrelia*, and the lack of detection of phage dispensed by *Borrelia burgdorferi* sensu lato or Relapsing Fever *Borrelia* in the sample indicates the subject is not infected by *Borrelia burgodorferi sensu lato* or Relapsing Fever *Borrelia.*

2. The method of claim 1, wherein the phage nucleic acid encodes a terminase protein.

3. The method of claim 1, wherein the phage nucleic acid comprises a nucleic acid according to the sequence of:
   - a) SEQ ID NOS: 1-10; or a nucleic acid with greater than or equal to 70-99.5% sequence homology with SEQ ID NOS: 1-10; or a fragment thereof, or wherein the phage nucleic acid is capable of encoding a protein according to any one of SEQ ID NOS: 36-45 or a fragment thereof, or
   - b) SEQ ID NOS: 84 or 86; or a nucleic acid with greater than or equal to 70-99.5% sequence homology with SEQ ID NOS: 84 or 86; or a fragment thereof, or wherein the phage nucleic acid is capable of encoding a protein according to any one of SEQ ID NOS: 85 or 87 or a fragment thereof.

4. The method of claim 1, wherein the phage nucleic acid detected comprises SEQ ID NO. 35; or a nucleic acid with greater than or equal to 70-99.5% sequence homology to SEQ ID NO. 35.

5. The method of claim 1, wherein the sample is plasma or whole blood.

6. The method of claim 1, wherein the sample is one that has been obtained in the early or late stage of *Borrelia burgdorferi* sensu lato or Relapsing Fever *Borrelia* infection.

7. The method of claim 1, wherein the *Borrelia burgdorferi* sensu lato may be any of *Borrelia afzelii, Borrelia spielmanii, Borrelia valaisiana, Borrelia garinii, Borrelia finlandensis, Borrelia bugdorferi sensu strictu, Borrelia bissettii, Borrelia bavariensis, Borrelia japonica, Borrelia lusitaniae, Borrelia sinica, Borrelia spielmanii, Borrelia tanukii, Borrelia turdi, Borrelia valaisiana, Borrelia yangtze, Borrelia mayonii, Borrelia carolinensis*, and *Borrelia andersonii, Borrelia lonestari*, and *Borrelia Americana* or any combination thereof.

8. The method of claim 1, wherein the Relapsing Fever *Borrelia* may be any of *Borrelia miyamotoi, Borrelia hermsii, Borrelia recurrentis, Borrelia crocidurae, Borrelia duttoni, Borrelia hispanica, Borrelia parkeri* and *Borrelia turicatae* or any combination thereof.

9. The method of claim 1, wherein the method may determine the presence or the absence of a species ofBorrelia *burgdorferi* sensu lato or Relapsing Fever *Borrelia* in the sample, the method comprising the steps of:
   - a) detecting the presence or absence of the *Borrelia burgdorferi* sensu lato or Relapsing Fever *Borrelia* species specific phage in the sample; and
   - b) determining the presence of the species of the *Borrelia burgdorferi* sensu lato or Relapsing Fever *Borrelia* in the sample on the basis of the detection of the species specific phage, or the absence of the species of *Borrelia burgdorferi* sensu lato or Relapsing Fever *Borrelia* in the sample on the basis of the lack of detection of the species specific phage.

10. The method of claim 1, wherein the method additionally comprises treatment of a patient for Lyme disease, the patient's sample having tested positive for *Borrelia burgdorferi* sensu lato.

11. The method of claim 1, wherein the method additionally comprises treatment of a patient for Relapsing Fever, the patient's sample having tested positive for Relapsing Fever *Borrelia*.

12. The method of claim 10 or 11, wherein treatment comprises administering at least one antibiotic.

13. The method of claim 1 wherein the method further comprises subjecting the isolated nucleic acid to amplification by real time polymerase chain reaction.

14. The method of claim 2 wherein the method further comprises a forward primer which is a nucleic acid comprising SEQ ID NO: 70 to amplify a *Borrelia* bugdorferi sensu strictu specific terminase gene.

15. The method of claim 14 wherein the method further comprises a reverse primer which is a nucleic acid comprising SEQ ID NO: 71 to amplify the *Borrelia* bugdorferi sensu strictu specific terminase gene.

16. The method of claim 2 wherein the method further comprises a primer which is a nucleic acid comprising any one of SEQ ID NOS: 88 to 93 to amplify a *Borrelia miyamotoi* specific terminase gene.

17. The method of claim 16 wherein the method further comprises a forward primer which is a nucleic acid comprising SEQ ID NO: 89 or 92 to amplify the *Borrelia miyamotoi* specific terminase gene.

18. The method of claim 17 wherein the method further comprises a reverse primer which is a nucleic acid comprising SEQ ID NO: 90 or 93 to amplify the *Borrelia miyamotoi* specific terminase gene.

* * * * *